United States Patent
Agarwal et al.

(10) Patent No.: US 11,642,384 B2
(45) Date of Patent: May 9, 2023

(54) COMPOSITIONS AND METHODS FOR THE TREATMENT OF NETHERTON SYNDROME

(71) Applicant: Krystal Biotech, Inc., Pittsburgh, PA (US)

(72) Inventors: Pooja Agarwal, Mars, PA (US); Suma Krishnan, Pittsburgh, PA (US); John C. Freedman, Pittsburgh, PA (US)

(73) Assignee: Krystal Biotech, Inc., Pittsburgh, PA (US)

( * ) Notice: Subject to any disclaimer, the term of this patent is extended or adjusted under 35 U.S.C. 154(b) by 0 days.

(21) Appl. No.: 17/871,805

(22) Filed: Jul. 22, 2022

(65) Prior Publication Data

US 2022/0409685 A1 Dec. 29, 2022

Related U.S. Application Data

(63) Continuation of application No. 16/581,150, filed on Sep. 24, 2019.

(60) Provisional application No. 62/735,582, filed on Sep. 24, 2018.

(51) Int. Cl.

| | |
|---|---|
| A61K 35/763 | (2015.01) |
| A61K 38/17 | (2006.01) |
| A61K 38/39 | (2006.01) |
| A61K 48/00 | (2006.01) |
| A61K 9/00 | (2006.01) |
| A61P 17/02 | (2006.01) |
| A61P 17/04 | (2006.01) |
| C12N 5/071 | (2010.01) |
| C12N 9/02 | (2006.01) |
| A61K 38/57 | (2006.01) |
| A61P 17/00 | (2006.01) |
| C12N 15/52 | (2006.01) |
| C12N 15/86 | (2006.01) |
| A61K 9/06 | (2006.01) |
| A61K 47/38 | (2006.01) |

(52) U.S. Cl.
CPC .......... *A61K 35/763* (2013.01); *A61K 9/0014* (2013.01); *A61K 38/1748* (2013.01); *A61K 38/39* (2013.01); *A61K 38/57* (2013.01); *A61K 48/005* (2013.01); *A61P 17/00* (2018.01); *A61P 17/02* (2018.01); *A61P 17/04* (2018.01); *C12N 5/0629* (2013.01); *C12N 9/0071* (2013.01); *C12N 15/52* (2013.01); *C12N 15/86* (2013.01); *A61K 9/06* (2013.01); *A61K 47/38* (2013.01); *C12N 2710/16643* (2013.01); *C12Y 114/11004* (2013.01)

(58) Field of Classification Search
None
See application file for complete search history.

(56) References Cited

U.S. PATENT DOCUMENTS

| | | | |
|---|---|---|---|
| 5,658,724 | A | 8/1997 | Deluca et al. |
| 5,672,344 | A | 9/1997 | Kelley et al. |
| 5,804,413 | A | 9/1998 | Deluca et al. |
| 5,998,174 | A | 12/1999 | Glorioso et al. |
| 6,106,826 | A | 8/2000 | Brandt et al. |
| 6,719,982 | B1 | 4/2004 | Coffin et al. |
| 6,835,184 | B1 | 12/2004 | Sage et al. |
| 6,846,670 | B2 | 1/2005 | Schwartz et al. |
| 6,887,490 | B1 | 5/2005 | Jahoda et al. |
| 6,939,851 | B1 | 9/2005 | Forssmann et al. |
| 7,531,167 | B2 | 5/2009 | Glorioso et al. |
| 9,314,505 | B2 | 4/2016 | Wise et al. |
| 9,877,990 | B2 | 1/2018 | Krishnan et al. |
| 10,155,016 | B2 | 12/2018 | Krishnan et al. |
| 10,174,341 | B2 | 1/2019 | Glorioso et al. |
| 10,441,614 | B2 | 10/2019 | Krishnan et al. |
| 11,185,564 | B2 | 11/2021 | Krishnan et al. |
| 2003/0082142 | A1 | 5/2003 | Coffin et al. |
| 2003/0093040 | A1 | 5/2003 | Mikszta |
| 2003/0190637 | A1 | 10/2003 | Hovnanian et al. |
| 2003/0223962 | A1 | 12/2003 | Crystal et al. |
| 2004/0253606 | A1 | 12/2004 | Aziz et al. |
| 2008/0299182 | A1 | 12/2008 | Zhang |
| 2011/0212530 | A1 | 9/2011 | Baltimore et al. |

(Continued)

FOREIGN PATENT DOCUMENTS

| | | |
|---|---|---|
| CN | 102 212 559 | 4/2014 |
| EP | 3377637 | 9/2018 |

(Continued)

OTHER PUBLICATIONS

Whitley et al. Pathogenesis and disease. In: Arvin A, Campadelli-Fiume G, Mocarski E, et al., eds. Human Herpesviruses: Biology, Therapy, and Immunoprophylaxis. Cambridge: Cambridge Univ. Press; 2007. Chapter 32. download: https://www.ncbi.nlm.nih.gov/books/NBK47449/, 19 pgs printed. (Year: 2007).*

(Continued)

*Primary Examiner* — Robert M Kelly

(74) *Attorney, Agent, or Firm* — Morrison & Foerster LLP

(57) ABSTRACT

The present disclosure provides recombinant nucleic acids comprising one or more polynucleotides encoding a Serine Protease Inhibitor Kazal-type (SPINK) polypeptide (e.g., a SPINK5 polypeptide); viruses comprising the recombinant nucleic acids; compositions and formulations comprising the recombinant nucleic acids and/or viruses; methods of their use (e.g., for the treatment of Netherton Syndrome); and articles of manufacture or kits thereof.

7 Claims, 9 Drawing Sheets

(2 of 9 Drawing Sheet(s) Filed in Color)

Specification includes a Sequence Listing.

(56) References Cited

U.S. PATENT DOCUMENTS

| | | |
|---|---|---|
| 2013/0331547 A1 | 12/2013 | Hall et al. |
| 2014/0256798 A1 | 9/2014 | Osborn et al. |
| 2014/0288155 A1 | 9/2014 | Hovnanian et al. |
| 2014/0341877 A1 | 11/2014 | Kolattukudy |
| 2014/0341881 A1 | 11/2014 | Deperthes |
| 2015/0038556 A1 | 2/2015 | Heartlein et al. |
| 2015/0352191 A1 | 12/2015 | South et al. |
| 2016/0153000 A1 | 6/2016 | Glorioso et al. |
| 2016/0324934 A1 | 11/2016 | Angel et al. |
| 2017/0096684 A1 | 4/2017 | Alton et al. |
| 2017/0290866 A1 | 10/2017 | Krishnan et al. |
| 2019/0040116 A1 | 2/2019 | Whitfill et al. |
| 2019/0078160 A1 | 3/2019 | Dressen et al. |
| 2019/0276845 A1 | 9/2019 | Glorioso et al. |
| 2020/0093874 A1 | 3/2020 | Agarwal et al. |
| 2020/0101123 A1 | 4/2020 | Krishnan et al. |
| 2020/0199618 A1 | 6/2020 | Krisky et al. |

FOREIGN PATENT DOCUMENTS

| | | |
|---|---|---|
| WO | WO 1999/064094 | 12/1999 |
| WO | WO 2000/040734 | 7/2000 |
| WO | WO 2013/121202 | 8/2013 |
| WO | WO 2015/009952 | 1/2015 |
| WO | WO 2015/117021 | 8/2015 |
| WO | WO 2017/165806 | 9/2017 |
| WO | WO 2017/165813 | 9/2017 |
| WO | WO 2017/176336 | 10/2017 |
| WO | WO 2020/068862 | 4/2020 |

OTHER PUBLICATIONS

Ain, et al (2020) "Gene Delivery to the Skin—How Far Have We Come?", Trends in Biotechnology, 39(5): 474-87. (Year: 2020).*
Perkins (2002) "Targeting apoptosis in neurological disease using the herpes simplex virus", Journal of Cellular and Molecular Medicine, 6(3): 341-56. (Year: 2002).*
Bauer (2017) "Atopic Eczema: Genetic Associations and Potential Links to Developmental Exposures", International Journal of Toxicology, 36(3): 187-98. (Year: 2017).*
Liao, et al. (2022) "SPINKs in Tumors: Potential Therapeutic Targets", Frontiers in Oncology, 12: article 833741, 15 pages. (Year: 2022).*
Ain et al., "Gene Delivery to the Skin—How Far Have We Come?" Trends Biotechnol. (2021) 39(5): 474-487.
Aldawsari et al., "Progress in Topical siRNA Delivery Approaches for Skin Disorders," Curr Pharm Des. (2015) 21(31): 4594-4605.
Andtbacka et. al., "Talimogene Laherparepvec Improves Durable Response Rate in Patients With Advanced Melanoma," J Clin Oncol. (2015) 33(25): 2780-2788.
Armstrong, M. "Krystal gets more skin in the epidermolysis bullosa game." Vantage. Mar. 5, 2019.
Armstrong, M. "Krystal gets a flying start in epidermolysis bullosa gene therapy" Vantage. Oct. 17, 2018.
Bastian et al., "Herpes simplex virus type 1 immediate-early protein ICP22 is required for VICE domain formation during productive viral infection." J Viral. Mar. 2010;84(5):2384-94. doi: 10.1128/JVI.01686-09. Epub Dec. 23, 2009.
Bauer, "Atopic Eczema: Genetic Associations and Potential Links to Developmental Exposures," Int J Toxicol. (2017) 36(3):187-198.
Bitoun et al., "LEKTI proteolytic processing in human primary keratinocytes, tissue distribution and defective expression in Netherton syndrome," Hum Mol Genet. (2003) 12(19): 2417-2430.
Bitoun et al., "Netherton syndrome: disease expression and spectrum of SPINK5 mutations in 21 families," J Invest Dermatol. (2002) 118(2): 352-361.
Braun et al., "Failure of Cyclosporine in Netherton's Syndrome," Dermatology. (1997) 195(1): 75.
Briot et al., "Kallikrein 5 induces atopic dermatitis-like lesions through PAR2-mediated thymic stromal lymphopoietin expression in Netherton syndrome," J Exp Med. (2009) 11;206(5): 1135-1147.

Burton et al., "Gene delivery using herpes simplex virus vectors." DNA Cell Biol. Dec. 2002;21(12):915-936.
Chamorro et al., "Gene Editing for the Efficient Correction of a Recurrent COL7A1 Mutation in Recessive Dystrophic Epidermolysis Bullosa Keratinocytes", Molecular Therapy—Nucleic Acids, vol. 5, 2016, pp. 1-13.
Christiano. Collagen, type VII, alpha 1 (epidermolysis bullosa, dystrophic, dominant and recessive) [*Homo sapiens*], NCBI Reference Sequence: NP_000085.1. Dep. Mar. 19, 1999.
Clinicaltrials.gov. NCT03536143: Topical Bercolagene Telserpavec (KB103) Gene Therapy to Restore Functional Collagen VII for the Treatment of Dystrophic Epidermolysis Bullosa (GEM-1). May 24, 2018.
Clinicaltrials.gov. NCT04047732: Topical KB105 Gene Therapy for the Treatment of TGM1-deficient Autosonnal Recessive Congenital Ichthyosis (ARCI). Aug. 7, 2019.
Clinicaltrials.gov. NCT04214002: The Natural History of Wounds in Patients with Dystrophic Epidermolysis Bullosa (DEB). Dec. 30, 2019.
Communication pursuant to Article 94(3) EPC for EP 16826873.8, dated Apr. 17, 2019, 7 pages.
Deraison et al., "LEKTI Fragments Specifically Inhibit KLK5, KLK7, and KLK14 and Control Desquamation through a pH-dependent Interaction," Mol Biol Cell. (2007) 18(9): 3607-3619.
Descargues et al., "Spink5-deficient mice mimic Netherton syndrome through degradation of desmoglein 1 by epidermal protease hyperactivity," Nat Genet. (2005) 37(1): 56-65.
Di et al., "Ex-vivo Gene Therapy Restores LEKTI Activity and Corrects the Architecture of Netherton Syndrome—derived Skin Grafts," Mol Ther. (2011) 19(2): 408-416.
Di et al., "Generation and Clinical Application of Gene-Modified Autologous Epidermal Sheets in Netherton Syndrome: Lessons Learned from a Phase 1 Trial," Hum Gene Ther. (2019) 30(9): 1067-1078.
Di et al., "Phase I study protocol for ex vivo lentiviral gene therapy for the inherited skin disease, Netherton syndrome," Hum Gene Ther Clin Dev. (2013) 24(4):182-190.
Egelrud et al., "hK5 and hK7, two serine proteinases abundant in human skin, are inhibited by LEKTI domain 6," Br J Dermatol. (2005) 153(6):1200-3.
Eming et al. Gene therapy and wound healing. Clin Dermatol. Jan.-Feb. 2007;25(1):79-92.
Eming et al., "Gene transfer in tissue repair: status, challenges and future directions," Exp Opin Biol Ther (2004) 4(9):1373-1386.
Examination Report No. 1 received for Australian Patent Application No. 2016401692, dated Jul. 12, 2019, 4 pages.
Fink et al., "Gene therapy for pain: Results of a Phase I clinical trial," Ann Neurol (2011) 70(2):207-212.
Fortugno et al., "Proteolytic Activation Cascade of the Netherton Syndrome—Defective Protein, LEKTI, in the Epidermis: Implications for Skin Homeostasis," J Invest Dermatol. (2011) 131(11): 2223-2232.
Fortugno et al., "The 420K LEKTI variant alters LEKTI proteolytic activation and results in protease deregulation: implications for atopic dermatitis," Hum Mol Genet. (2012) 21(19): 4187-4200.
Furio et al., "KLK5 Inactivation Reverses Cutaneous Hallmarks of Netherton Syndrome," PLoS Genet. (2015) 11(9): e1005389.
Georgiadis et al., "Lentiviral Engineered Fibroblasts Expressing Codon—Optimized COL7A1 Restore Anchoring Fibrils in RDEB", Journal of Investigative Dermatology, (2016) 136: 284-292.
Glorioso. "Herpes simplex viral vectors: late bloomers with big potential." Hum Gene Ther. (2014) 25(2): 83-91.
Goins et al. "Engineering HSV-1 Vectors for Gene Therapy," Methods Mol Biol (2014) 1144: 63-79.
Goins et al. "Generation of replication-competent and -defective HSV vectors," Cold Spring Harb Protoc. May 1, 2011;2011(5): 512; pdb.prot5615.
Gorell et al., "Gene therapy for skin diseases," Cold Spring Harb Perspect Med (2014) 4:a015149.
Goto et al., "Fibroblasts Show More Potential as Target Cells than Keratinocytes in COL7A1 Gene Therapy of Dystrophic Epidermolysis Bullosa", Journal of Investigative Dermatology, (2006) 126: 766-772.

(56) References Cited

OTHER PUBLICATIONS

Gurevich et al. 759 "Successful in vivo COL7A1 gene delivery and correction of recessive dystrophic epidermolysis bullosa (RDEB) skin using an off the shelf HSV-1 vector (KB103)." J Invest Derm. vol. 138, Iss. 5 Supp. May 2018, p. S129. Available online Apr. 19, 2018.
Hachem et al., "Serine protease activity and residual LEKTI expression determine phenotype in Netherton syndrome," J Invest Dermatol. (2006) 126(7): 1609-1621.
Hausser et al., "Severe congenital generalized exfoliative erythroderma in newborns and infants: a possible sign of Netherton syndrome," Pediatr Dermatol. (1996) 13(3):183-199.
Heikkinen et al., "Diremerization of human lysyl hydroxylase 3 (LH3) is mediated by the amino acids 541 547," Matrix Biology (2010) 30(1):27-33.
Hennig et al., "HEK293-based production platform for y-retroviral (self-inactivating) vectors: application for safe and efficient transfer of COL7A1 cDNA". Hum Gene Ther Clin Dev. Dec. 2014;25(4):218-28.
International Search Report and Written Opinion for PCT/US2019/052779, dated Jan. 14, 2020, 16 pages.
Ishida-Yamamoto et al., "LEKTI is localized in lamellar granules, separated from KLK5 and KLK7, and is secreted in the extracellular spaces of the superficial stratum granulosum," J Invest Dermatol. Feb. 2005;124(2):360-366.
Izadi et al., "Clinical approach to the patient with refractory atopic dermatitis," Ann Allergy Asthma Immunol (2018) 120: 23-33.
Jayakumar et al., "Molecular and Biochemical Properties of Lympho-Epithelial Kazal-Type-Inhibitor (LEKTI)," MOJ Proteomics Bioinform 2015, 2(4): 00053.
Jayarajan et al., "Ex vivo gene modification therapy for genetic skin diseases-recent advances in gene modification technologies and delivery," Exp Dermatol. (2021) 30(7): 887-896.
Jones et al., "Neonatal hypernatraemia in two siblings with Netherton's syndrome," British Journal of Dermatology (1986) 114: 741-743.
Judge et al., "A clinical and immunological study of Netherton's syndrome," British Journal oJ Dermatology (1994) 131: 615-621.
Jung et al., "Atopic dermatitis: Therapeutic concepts evolving from new pathophysiologic insights," J Allergy Clin Immunol. (2008) 122(6): 1074-1081.
Kohlhapp et al., Molecular Pathways: Mechanism of Action for Talimogene Laherparepvec, a New Oncolytic Virus Immunotherapy, Clinical Cancer Research (2015) 22(5):1048-1054.
Komatsu et al., "Correlation between SPINK5 Gene Mutations and Clinical Manifestations in Netherton Syndrome Patients," Journal of Investigative Dermatology (2008) 128: 1148-1159.
Kopecki et al., "Commentary: New advances in the development of therapies for treating inherited skin fragility disorders," Wound Practice and Research (2015) 23(4): 184, Dec. 5, 2015.
Krisky et al., "Development of herpes simplex virus replication-defective multigene vectors for combination gene therapy applications," Gene Ther (1998) 5(110):1517-1530.
Krystal Biotech, Inc. "Krystal Biotech Announces Settlement with PeriphaGen, Inc." Mar. 15, 2022, https://ir.krystalbio.com/node/8481/pdf. (Year: 2022).
Lachmann, R. "Herpes simplex virus-based vectors," Int J Exp Pathol. (2004) 85(4): 177-190.
Lacroix et al., "Clinical expression and new SPINK5 splicing defects in Netherton syndrome: unmasking a frequent founder synonymous mutation and unconventional intronic mutations," J Invest Dermatol. (2012) 132: 575-582.
Le et al., "Regulation of serine protease inhibitor Kazal type-5 (SPINK5) gene expression in the keratinocytes," Environ Health Prev Med. (2014) 19(4): 307-313.
Leclerc-Mercier et al., "Skin Biopsy in Netherton Syndrome: A Histological Review of a Large Series and New Findings," Am J Dermatopathol. (2016) 38(2): 83-91.
Lewin et al., "Gene therapy for autosomal dominant disorders of keratin," J Investig Dermatol Symp Proc. (2005) 10(1): 47-61.
Lu et al., "Topical Application of Viral Vectors for Epidermal Gene Transfer", J Invest Dermatol. (1997) 108(5): 803-808.
Ma et al., "Efficacy of Herpes Simplex Virus Vector Encoding V the Human Preproenkephalin Gene for Treatment of Facial Pain in Mice," J aral Facial Pain Headachce (2016) 30(1):42-50.
Magert et al., "LEKTI, a novel 15-domain type of human serine proteinase inhibitor," J Biol Chem. (1999) 274(31): 21499-21502.
Marconi et al., "HSV as a Vector in Vaccine Development and Gene Therapy." In: Madame Curie Bioscience Database [Internet]. Austin (TX): Landes Bioscience; 2000-2013. 30 pages.
Marconi et al., "Replication-defective herpes simplex virus vectors for gene transfer in vivo," Proc Natl Acad Sci USA (1996) 93:11319-11320.
Mayr et al., "Gene Therapy for the COL7A1 Gene", Chapter 23, Intech, 2013, pp. 561-589.
McGowan et al., "Keratin 17 n ull mice exhibit age- and strain-dependent alopecia," Genes & Dev (2002) 16:1412-1422.
Meyer-Hoffert et al., "Isolation ofSPINK6 in human skin: selective inhibitor of kallikrein-related peptidases," J Biol Chem.( 2010) 285(42): 32174-81.
Michael et al., Biochemical and enzymatic characterization of human kallikrein 5 (hK5), a novel serine protease potentially involved in cancer progression, J Biol Chem. (2005) 280(15): 14628-14635.
Mitsudo et al., "Inhibition of serine proteinases plasmin, trypsin, subtilisin A, cathepsin G, and elastase by LEKTI: a kinetic analysis," Biochemistry. (2003) 42(13): 3874-3881.
Miyai et al., "Keratinocyte-Specific Mesotrypsin Contributes to the Desquamation Process via Kallikrein Activation and LEKTI Degradation," Journal of Investigative Dermatology (2014) 134, 1665-1674.
Miyagawa et al., "Herpes simplex viral-vector design for efficient transfection of nonneuronal cells without cytotoxcity," Proc Natl Acad Sci USA (2015) 112(13):E1632-E1641.
Mody et al., "Herpes Simplex Virus: A Versatile Tool for Insights Into Evolution, Gene Delivery, and Tumor Immunotherapy," Virology (Auckl). (2020) 11:1178122X20913274.
Ng et al., "Fibroblast-Derived Dermal Matrix Drives Development of Aggressive Cutaneous Squamous Cell Carcinoma in Patients with Recessive Dystrophic Epidermolysis Bullosa", Cancer Research, vol. 72, No. 14, Jul. 15, 2012, pp. 3522-3534.
Non-Final Office Action received for U.S. Appl. No. 15/393,151, dated Apr. 14, 2017, 13 pages.
Non-Final Office Action received for U.S. Appl. No. 16/177,153, dated May 9, 2019, 13 pages.
Notice of Allowance received for U.S. Appl. No. 15/393,151, dated Dec. 6, 2017, 11 pages.
Notice of Allowance received for U.S. Appl. No. 16/177,153, dated Aug. 30, 2019, 10 pages.
Numata et al., "A compound synonymous mutation c.474G>A with p.Arg578X mutation in SPINK5 causes splicing disorder and mild phenotype in Netherton syndrome," Exp Dermatol. (2016) 25(7): 568-70.
Perkins, "Targeting apoptosis in neurological disease using the herpes simplex virus," J Cell Mol Med. (2002) 6(3): 341-56.
Renner et al., "Comèl-Netherton syndrome—defined as primary immunodeficiency," J Allergy Clin Immunol. (2009) 124(3): 536-543.
Roedl et al., "rAAV2-mediated restoration of LEKTI in LEKTI-deficient cells from Netherton patients," J Dermatol Sci. (2011) 61(3):194-198.
Roelandt et al., "LEKTI-1 in sickness and in health," Int J Cosmet Sci. (2009) 31(4): 247-254.
Salam A. "Krystal's KB103 splits experts' thoughts on potential for HSV-1 risk in dystrophic epidermolysis bullosa patients, but final Phase I/II efficacy assured." Nov. 7, 2018. Biopharm Insight.
Sales et al., "Matriptase initiates activation of epidermal pro-kallikrein and disease onset in a mouse model of Netherton syndrome," Nat Genet. (2010) 42(8): 676-683.
Salmon-Ehr et al., "Implication of Interleukin-4 in Wound Healing", Laboratory Investigation, vol. 80, No. 8, Aug. 2000, pp. 1337-1343.

(56) References Cited

OTHER PUBLICATIONS

Sankar et al., "A novel role for keratin 17 in coordinating oncogenic transformation and cellular adhersion in eqing sarcoma," Molecular and Cellular Biology (2013) 33(22):4448-4460.
Sarri et al., "Netherton Syndrome: A Genotype-Phenotype Review," Mol Diagn Ther. (2017) 21(2):137-152.
Schmuth et al., "Inherited ichthyoses/generalized Mendelian disorders of cornification," Eur J Hum Genet. (2013) 21(2): 123-133.
Shen et al., "Herpes simplex virus 1 (HSV-1) for cancer treatment," Cancer Gene Therapy (2006) 13: 975-992.
Siprashvili et al., "Long-term type VII collagen restoration to human epidermolysis bullosa skin tissue," Hum Gene Ther. Oct. 2010;21(10):1299-310.
Smigiel et al., "Is c.1431-12G>A A common European mutation of SPINK5? report of a patient with Netherton Syndrome," Balkan J Med Genet. (2017) 19(2):81-84.
Stow et al., Isolation and characterization of a herpes simplex virus type 1 mutant containing a deletion within the gene encoding the immediate early polypeptide Vmw110. J Gen Viral. Dec. 1986;67 (Pt 12):2571-85.
Tartaglia-Polcini et al., "SPINK5, the defective gene in netherton syndrome, encodes multiple LEKTI isoforms derived from alternative pre-mRNA processing," J Invest Dermatol. (2006) 126(2): 315-24.
Theopold et al., "A novel replication-defective HSV-1 vector for regulatable gene delivery to wounds," Journal of the American College of Surgeons (2004) 199(3):57-58.
Uitto et al., "Progress toward Treatment and Cure of Epidermolysis Bullosa: Summary of the DEBRA International Research Symposium EB2015", Journal of Investigative Dermatology, vol. 136, 2016, pp. 352-358.
Watt et al., "Lysyl Hydroxylase 3 Localizes to Epidermal Basement Membrane and Is Reduced in Patients with Recessive Dystrophic Epidermolysis Bullosa", Plos One, (2015) 10(9): e0137639.
Weiss et al., "The Role of Interleukin 10 in the Pathogenesis and Potential Treatment of Skin Diseases", Journal of the American Academy of Dermatology, vol. 50, No. 5, May 2004, pp. 657-675.
White et al., "Evaluation and optimization of the administration of a selectively replicating herpes simplex viral vector to the brain by convection-enhanced delivery," Cancer Gene Ther. May 2011;18(5):358-69. doi: 10.1038/ cgt.2011.2. Epub Mar. 4, 2011.
Wolfe et al., "Engineering Herpes Simplex Viral Vectors for Therapeutic Gene Transfer", Chapter 6, Gene and Cell Therapy, 2004, pp. 103-129.
Woodley et al., "Normal and Gene-Corrected Dystrophic Epidermolysis Bullosa Fibroblasts Alone Can Produce Type VII Collagen at the Basement Membrane Zone", The Journal of Investigative Dermatology, vol. 121, No. 5, Nov. 2003, pp. 1021-1028.
Yang et al., "Epidermal detachment, desmosomal dissociation, and destabilization of corneodesmosin in Spink5-/- mice," Genes Dev. (2004) 18(19): 2354-8.

* cited by examiner

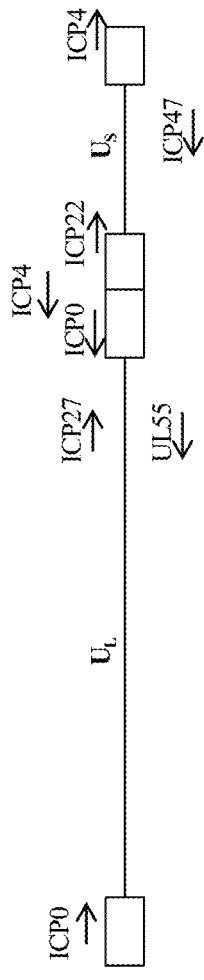
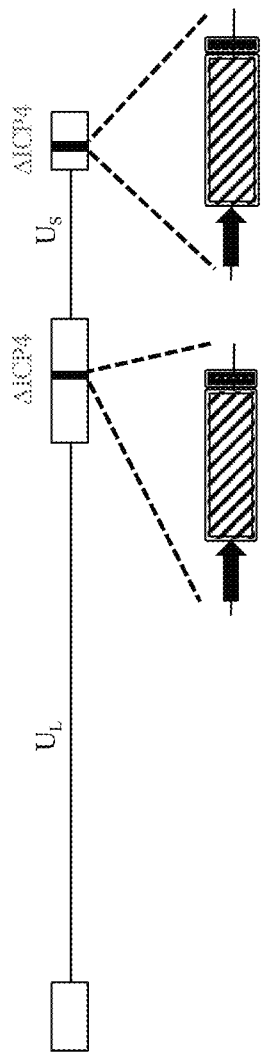
FIG. 1A
FIG. 1B

COMPOSITIONS AND METHODS FOR THE TREATMENT OF NETHERTON SYNDROME

CROSS REFERENCE TO RELATED APPLICATIONS

This application is continuation of U.S. patent application Ser. No. 16/581,150, filed Sep. 24, 2019, now pending, which claims the priority benefit of U.S. Provisional Application Ser. No. 62/735,582, filed Sep. 24, 2018, each of which is incorporated herein by reference in its entirety.

SUBMISSION OF AN ELECTRONIC SEQUENCE LISTING FILE

The content of the electronic Sequence Listing (file name: 761342000401SeqList.xml, date created: Sep. 23, 2022, size: 56,665 bytes) is herein incorporated by reference in its entirety.

FIELD OF THE INVENTION

The present disclosure relates, in part, to recombinant nucleic acids comprising one or more polynucleotides encoding a Serine Protease Inhibitor Kazal-type (SPINK) polypeptide (e.g., a human SPINK5 polypeptide), viruses comprising the same, pharmaceutical compositions, formulations, and medicaments thereof, and methods of their use (e.g., for the treatment of Netherton Syndrome).

BACKGROUND

Netherton Syndrome (NS), also referred to as Comèl-Netherton Syndrome, is a debilitating autosomal recessive skin disorder that causes defective keratinization, severe skin barrier defects, and recurrent infections. Patients present shortly after birth with generalized rashes that develop into severe ichthyosis (Comèl, 1949. *Dermatologica.* 98(3): 133-6). Infants with more severe NS symptoms are associated with failure to thrive, hypernatremic dehydration secondary to excess fluid loss, delayed growth, short stature, and recurrent infections (Jones et al., 1986. *Br J Dermatol.* 114(6):741-3; Hausser et al., 1996. *Pediatr Dermatol.* 13(3): 183-99). Postnatal mortality rates for Netherton Syndrome are extremely high, with up to 20% of patients failing to reach their first birthday (Renner et al., 2009. *J Allergy Clin Immunol.* 124(3):536-43).

Clinically, Netherton Syndrome is characterized by congenital ichthyosiform erythroderma, hair shaft defects, recurrent infections, and a defective skin barrier (Judge et al., 1994. *Br J Dermatol.* 131(5):615-21; Schmuth et al., 2013. *Eur J Hum Genet.* 21(2):123-33). Hair shafts are fragile and break easily due to trichorrhexis invaginata, or "bamboo hair", resulting in short sparse hair. A predisposition to allergies, asthma, and eczema is also characteristic of NS. Ultimately, those afflicted by Netherton Syndrome often experience chronic skin inflammation, severe dehydration, and stunted growth.

The disease arises due to mutations in the Serine Protease Inhibitor Kazal-type 5 (SPINK5) gene, resulting in loss of activity of its encoded serine protease inhibitor protein SPINK5 (also known as Lympho-Epithelial Kazal-type-related Inhibitor (LEKTI)) (Bitoun et al., 2002. *J Invest Dermatol.* 118(2):352-61). In healthy individuals, SPINK5 is one of the serine protease inhibitors expressed in the outermost layers of the skin, and it plays a critical role in the regulation of serine proteases which hydrolyze extracellular proteins that hold corneocytes together. In patients suffering from Netherton Syndrome, the suppressive effects of SPINK5 on these serine proteases is abolished due to underlying genetic mutations in the SPINK5 gene (Komatsu et al., 2008. *J Invest Dermatol.* 128(5):1148-59). Consequently, hyperactivated serine proteases in the skin cause uncontrolled desquamation, leading to a defective skin barrier (Descargues et al., 2005. *Nat Genet.* 37(1):56-65).

Presently, there is no known cure for Netherton Syndrome, and treatment options for patients are limited. Current care focuses on managing the symptoms of the disease, including using moisturizing products to minimize scaling/cracking of the skin, and providing anti-infective treatments when appropriate. Additionally, intravenous administration of immunoglobulin to reduce skin infections has gained in popularity. Unfortunately, while steroid and retinoid products have shown some success in treating other ichthyosis-related disorders, these products have proven ineffective against NS, and may in fact make things worse for affected individuals (Braun et al., 1997. *Dermatology.* 195(1):75). Thus, there exists a clear need for novel treatment options targeting molecular correction of SPINK5 deficiencies observed in this sensitive patient population.

All references cited herein, including patent applications, patent publications, non-patent literature, and NCBI/UniProtKB/Swiss-Prot accession numbers are herein incorporated by reference in their entirety, as if each individual reference were specifically and individually indicated to be incorporated by reference.

BRIEF SUMMARY

The present disclosure provides recombinant nucleic acids comprising one or more polynucleotides encoding a Serine Protease Inhibitor Kazal-type (SPINK) polypeptide (e.g., a SPINK5 polypeptide); viruses comprising the recombinant nucleic acids; compositions and formulations comprising the recombinant nucleic acids and/or viruses; methods of their use (e.g., for the treatment of Netherton Syndrome); and articles of manufacture or kits thereof.

In order to meet these and other needs, provided herein are recombinant nucleic acids (e.g., recombinant herpes simplex virus genomes) encoding Serine Protease Inhibitor Kazal-type (SPINK) polypeptides (e.g., SPINK5 polypeptides) for use in viruses (e.g., herpes viruses), pharmaceutical compositions and formulations, medicaments, and/or methods useful for remedying SPINK deficiencies and/or for treating an individual having, or at risk of developing, a SPINK-associated disorder (e.g., Netherton Syndrome, atopic dermatitis, hereditary pancreatitis, tropical calcific pancreatitis, spermatogenic failure 29, etc. The present inventors have shown that the recombinant viruses described herein were capable of transducing human epidermal cells, successfully expressing the encoded exogenous SPINK (RNA and protein), and that the exogenous polypeptide was appropriately secreted and was fully functional (see e.g., Example 2). Moreover, the present inventors have shown that the viruses described herein may be successfully administered either topically or intradermally in vivo without significant cytotoxicity, allowing for the encoded human SPINK polypeptide to be expressed in and localized to the appropriate region of the skin (see e.g., Example 3). Without wishing to be bound by theory, it is believed that increasing, augmenting, and/or supplementing the levels of SPINK polypeptide (e.g., human SPINK5) in a subject in need thereof by administering one or more of the recombinant nucleic acids, viruses, compositions, and/or medicaments described herein will: 1) enhance anti-inflammatory and/or anti-microbial protection of mucous epithelia; 2) reduce transepidermal water loss (TEWL); 3) inhibit desquamation; and 4) reduce or treat skin barrier defects in the subject. In addition, without wishing to be bound by theory, it is believed that increasing, augmenting, and/or supplementing the levels of a SPINK polypeptide (e.g., human SPINK5) in one or more cells of a subject (by administering any of the recombinant nucleic acids, viruses, medicaments, and/or pharmaceutical composition described herein) will lead to the treatment of existing skin abnormalities in individuals suffering from a SPINK deficiency (e.g., Netherton Syndrome, atopic dermatitis, etc.), as well as will prevent or delay reformation of skin abnormalities in the treated areas.

Accordingly, certain aspects of the present disclosure relate to a recombinant herpes virus genome comprising one or more polynucleotides encoding a Serine Protease Inhibitor Kazal-type (SPINK) polypeptide. In some embodiments, the recombinant herpes virus genome comprises two or more polynucleotides encoding a SPINK polypeptide. In some embodiments, the recombinant herpes virus genome is replication competent. In some embodiments, the recombinant herpes virus genome is replication defective. In some embodiments that may be combined with any of the preceding embodiments, the recombinant herpes virus genome is selected from a recombinant herpes simplex virus genome, a recombinant varicella zoster virus genome, a recombinant human cytomegalovirus genome, a recombinant herpesvirus 6A genome, a recombinant herpesvirus 6B genome, a recombinant herpesvirus 7 genome, a recombinant Kaposi's sarcoma-associated herpesvirus genome, and any combinations or derivatives thereof. In some embodiments that may be combined with any of the preceding embodiments, the recombinant herpes virus genome is a recombinant herpes simplex virus genome. In some embodiments, the recombinant herpes simplex virus genome is a recombinant type 1 herpes simplex virus (HSV-1) genome, a recombinant type 2 herpes simplex virus (HSV-2) genome, or any derivatives thereof. In some embodiments, the recombinant herpes simplex virus genome is a recombinant HSV-1 genome.

In some embodiments that may be combined with any of the preceding embodiments, the recombinant herpes simplex virus genome comprises an inactivating mutation. In some embodiments, the inactivating mutation is in a herpes simplex virus gene. In some embodiments, the inactivating mutation is a deletion of the coding sequence of the herpes simplex virus gene. In some embodiments, the herpes simplex virus gene is selected from Infected Cell Protein (ICP) 0 (one or both copies), ICP4 (one or both copies), ICP22, ICP27, ICP47, thymidine kinase (tk), Long Unique Region (UL) 41, and UL55. In some embodiments, the recombinant herpes simplex virus genome comprises an inactivating mutation in one or both copies of the ICP4 gene. In some embodiments, the recombinant herpes simplex virus genome comprises an inactivating mutation in the ICP22 gene. In some embodiments, the recombinant herpes simplex virus genome comprises an inactivating mutation in the UL41 gene. In some embodiments, the recombinant herpes simplex virus genome comprises an inactivating mutation in one or both copies of the ICP0 gene. In some embodiments, the recombinant herpes simplex virus genome comprises an inactivating mutation in the ICP27 gene. In some embodiments, the recombinant herpes simplex virus genome comprises an inactivating mutation in the UL55 gene. In some embodiments, the recombinant herpes simplex virus genome comprises an inactivating mutation in the Joint region. In some embodiments, the recombinant herpes simplex virus genome comprises a deletion of the Joint region.

In some embodiments that may be combined with any of the preceding embodiments, the recombinant herpes virus genome comprises the one or more polynucleotides encoding the SPINK polypeptide within one or more viral gene loci. In some embodiments that may be combined with any of the preceding embodiments, the recombinant herpes simplex virus genome comprises the one or more polynucleotides encoding the SPINK polypeptide within one or both of the ICP4 viral gene loci. In some embodiments that may be combined with any of the preceding embodiments, the recombinant herpes simplex virus genome comprises the one or more polynucleotides encoding the SPINK polypeptide within the ICP22 viral gene locus. In some embodiments that may be combined with any of the preceding embodiments, the recombinant herpes simplex virus genome comprises the one or more polynucleotides encoding the SPINK polypeptide within the UL41 viral gene locus.

In some embodiments that may be combined with any of the preceding embodiments, the SPINK polypeptide is a human SPINK polypeptide. In some embodiments that may be combined with any of the preceding embodiments, the SPINK polypeptide is a Serine Protease Inhibitor Kazal-type 5 (SPINK5) polypeptide. In some embodiments that may be combined with any of the preceding embodiments, the SPINK polypeptide is a human SPINK5 polypeptide. In some embodiments that may be combined with any of the preceding embodiments, the SPINK polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 7-25. In some embodiments that may be combined with any of the preceding embodiments, the SPINK polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 7-9. In some embodiments that may be combined with any of the preceding embodiments, the SPINK polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence of SEQ ID NO: 7. In some embodiments that may be combined with any of the preceding embodiments, the SPINK polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence of SEQ ID NO: 8. In some embodiments that may be combined with any of the preceding embodiments, the SPINK polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence of SEQ ID NO: 9.

In some embodiments that may be combined with any of the preceding embodiments, the recombinant herpes virus genome has reduced cytotoxicity when introduced into a target cell as compared to a corresponding wild-type herpes virus genome. In some embodiments, the target cell is a human cell. In some embodiments, the target cell is a cell of the epidermis and/or dermis. In some embodiments, the target cell is a keratinocyte or fibroblast.

Other aspects of the present disclosure relate to a herpes virus comprising any of the recombinant herpes virus genomes described herein. In some embodiments, the herpes virus is replication competent. In some embodiments, the herpes virus is replication defective. In some embodiments that may be combined with any of the preceding embodiments, the herpes virus has reduced cytotoxicity as compared to a corresponding wild-type herpes virus. In some embodiments that may be combined with any of the preceding embodiments, the herpes virus is selected from a herpes simplex virus, a varicella zoster virus, a human cytomegalovirus, a herpesvirus 6A, a herpesvirus 6B, a herpesvirus 7, a Kaposi's sarcoma-associated herpesvirus, and any combinations or derivatives thereof. In some embodiments that may be combined with any of the preceding embodiments, the herpes virus is a herpes simplex virus. In some embodiments, the herpes simplex virus is an HSV-1, an HSV-2, or any derivatives thereof. In some embodiments, the herpes simplex virus is an HSV-1.

Other aspects of the present disclosure relate to a pharmaceutical composition comprising any of the recombinant herpes virus genomes described herein and/or any of the herpes viruses described herein and a pharmaceutically acceptable excipient. In some embodiments, the pharmaceutical composition is suitable for topical, transdermal, subcutaneous, intradermal, oral, sublingual, buccal, rectal, vaginal, inhaled, intravenous, intraarterial, intramuscular, intracardiac, intraosseous, intraperitoneal, transmucosal, intravitreal, subretinal, intraarticular, peri-articular, local, epicutaneous administration, or any combinations thereof. In some embodiments that may be combined with any of the preceding embodiments, the pharmaceutical composition is suitable for topical, transdermal, subcutaneous, intradermal, and/or transmucosal administration. In some embodiments that may be combined with any of the preceding embodiments, the pharmaceutical composition is suitable for topical, transdermal, and/or intradermal administration. In some embodiments that may be combined with any of the preceding embodiments, the pharmaceutical composition is suitable for topical and/or intradermal administration. In some embodiments that may be combined with any of the preceding embodiments, the pharmaceutical composition is suitable for topical administration. In some embodiments that may be combined with any of the preceding embodiments, the pharmaceutical composition comprises a methylcellulose gel (e.g., a carboxy methylcellulose gel, a hydroxypropyl methylcellulose gel, etc.). In some embodiments that may be combined with any of the preceding embodiments, the pharmaceutical composition comprises a phosphate buffer. In some embodiments that may be combined with any of the preceding embodiments, the pharmaceutical composition comprises glycerol. In some embodiments that may be combined with any of the preceding embodiments, the pharmaceutical composition comprises a lipid carrier. In some embodiments that may be combined with any of the preceding embodiments, the pharmaceutical composition comprises a nanoparticle carrier.

Other aspects of the present disclosure relate to the use of any of the recombinant nucleic acids, herpes viruses, and/or pharmaceutical compositions described herein as a medicament.

Other aspects of the present disclosure relate to the use of any of the recombinant nucleic acids, herpes viruses, and/or pharmaceutical compositions described herein in a therapy.

Other aspects of the present disclosure relate to the use of any of the recombinant nucleic acids, herpes viruses, and/or pharmaceutical compositions described herein in the production or manufacture of a medicament for treating one or more signs or symptoms of SPINK polypeptide deficiency (e.g., Netherton Syndrome, atopic dermatitis, etc.).

Other aspects of the present disclosure relate to a method of enhancing, increasing, augmenting, and/or supplementing the levels of a SPINK polypeptide in one or more cells of a subject comprising administering to the subject an effective amount of any of the herpes viruses described herein and/or any of the pharmaceutical compositions described herein. In some embodiments, the SPINK polypeptide is a SPINK5 polypeptide (e.g., a human SPINK5 polypeptide). In some embodiments that may be combined with any of the preceding embodiments, the subject is a human. In some embodiments that may be combined with any of the preceding embodiments, the subject's genome comprises a loss-of-function mutation in a SPINK5 gene. In some embodiments that may be combined with any of the preceding embodiments, the herpes virus and/or pharmaceutical composition is administered topically, transdermally, subcutaneously, epicutaneously, intradermally, orally, sublingually, buccally, rectally, vaginally, intravenously, intraarterially, intramuscularly, intraosseously, intracardially, intraperitoneally, transmucosally, intravitreally, subretinally, intraarticularly, periarticularly, locally, or via inhalation to the subject. In some embodiments that may be combined with any of the preceding embodiments, the herpes virus and/or pharmaceutical composition is administered topically, transdermally, subcutaneously, intradermally, or transmucosally to the subject. In some embodiments that may be combined with any of the preceding embodiments, the herpes virus and/or pharmaceutical composition is administered topically to the subject. In some embodiments that may be combined with any of the preceding embodiments, the skin of the subject is abraded prior to administration.

Other aspects of the present disclosure relate to a method of enhancing, increasing, augmenting, and/or supplementing anti-inflammatory and/or anti-microbial protection of mucous epithelia in a subject in need thereof comprising administering to the subject an effective amount of any of the herpes viruses described herein and/or any of the pharmaceutical compositions described herein. In some embodiments, the subject is a human. In some embodiments that may be combined with any of the preceding embodiments, the subject's genome comprises a loss-of-function mutation in a SPINK5 gene. In some embodiments that may be combined with any of the preceding embodiments, the herpes virus and/or pharmaceutical composition is administered topically, transdermally, subcutaneously, epicutaneously, intradermally, orally, sublingually, buccally, rectally, vaginally, intravenously, intraarterially, intramuscularly, intraosseously, intracardially, intraperitoneally, transmucosally, intravitreally, subretinally, intraarticularly, periarticularly, locally, or via inhalation to the subject. In some embodiments that may be combined with any of the preceding embodiments, the herpes virus and/or pharmaceutical composition is administered topically, transdermally, subcutaneously, intradermally, or transmucosally to the subject. In some embodiments that may be combined with any of the preceding embodiments, the herpes virus and/or pharmaceutical composition is administered topically to the subject. In some embodiments that may be combined with any of the preceding embodiments, the skin of the subject is abraded prior to administration.

Other aspects of the present disclosure relate to a method of repressing desquamation in a subject in need thereof comprising administering to the subject an effective amount of any of the herpes viruses described herein and/or any of the pharmaceutical compositions described herein. In some embodiments, the subject is a human. In some embodiments that may be combined with any of the preceding embodiments, the subject's genome comprises a loss-of-function mutation in a SPINK5 gene. In some embodiments that may be combined with any of the preceding embodiments, the herpes virus and/or pharmaceutical composition is administered topically, transdermally, subcutaneously, epicutaneously, intradermally, orally, sublingually, buccally, rectally, vaginally, intravenously, intraarterially, intramuscularly, intraosseously, intracardially, intraperitoneally, transmucosally, intravitreally, subretinally, intraarticularly, periarticularly, locally, or via inhalation to the subject. In some embodiments that may be combined with any of the preceding embodiments, the herpes virus and/or pharmaceutical composition is administered topically, transdermally, subcutaneously, intradermally, or transmucosally to the subject. In some embodiments that may be combined with any of the preceding embodiments, the herpes virus and/or pharmaceutical composition is administered topically to the subject. In some embodiments that may be combined with any of the preceding embodiments, the skin of the subject is abraded prior to administration.

Other aspects of the present disclosure relate to a method of reducing or treating a skin barrier defect in a subject in need thereof comprising administering to the subject an effective amount of any of the herpes viruses described herein and/or any of the pharmaceutical compositions described herein. In some embodiments, the skin barrier defect is transepithelial water loss (TEWL). In some embodiments that may be combined with any of the preceding embodiments, the subject is a human. In some embodiments that may be combined with any of the preceding embodiments, the subject's genome comprises a loss-of-function mutation in a SPINK5 gene. In some embodiments that may be combined with any of the preceding embodiments, the herpes virus and/or pharmaceutical composition is administered topically, transdermally, subcutaneously, epicutaneously, intradermally, orally, sublingually, buccally, rectally, vaginally, intravenously, intraarterially, intramuscularly, intraosseously, intracardially, intraperitoneally, transmucosally, intravitreally, subretinally, intraarticularly, periarticularly, locally, or via inhalation to the subject. In some embodiments that may be combined with any of the preceding embodiments, the herpes virus and/or pharmaceutical composition is administered topically, transdermally, subcutaneously, intradermally, or transmucosally to the subject. In some embodiments that may be combined with any of the preceding embodiments, the herpes virus and/or pharmaceutical composition is administered topically to the subject. In some embodiments that may be combined with any of the preceding embodiments, the skin of the subject is abraded prior to administration.

Other aspects of the present disclosure relate to a method of providing prophylactic, palliative, or therapeutic relief of one or more signs or symptoms of Netherton Syndrome (NS) in a subject in need thereof comprising administering to the subject an effective amount of any of the herpes viruses described herein and/or any of the pharmaceutical compositions described herein. In some embodiments, the one or more signs or symptoms of NS are selected from defective keratinization, a defective skin barrier, chronic skin inflammation, universal pruritus, severe dehydration, stunted growth, trichorrhexis invaginata and/or trichorrhexis nodosa, leaking fluid from the skin, development of ring-like lesions on the skin, eczema, increased susceptibility to infection, recurrent skin infections, increased susceptibility to allergy, development of scaly/reddish skin, development of ichthyosis linearis circumflexa and/or ichthyosiform erythroderma, altered immunoglobulin levels, immature natural killer cells having reduced lytic function, difficulty regulating body temperature, and any combinations thereof. In some embodiments that may be combined with any of the preceding embodiments, the one or more sign or symptoms of NS are selected from defective keratinization, a defective skin barrier, recurrent skin infections, congenital ichthyosiform erythroderma, ichthyosis linearis circumflexa, trichorrhexis invaginata, chronic skin inflammation, and any combinations thereof. In some embodiments that may be combined with any of the preceding embodiments, the subject is a human. In some embodiments that may be combined with any of the preceding embodiments, the subject's genome comprises a loss-of-function mutation in a SPINK5 gene. In some embodiments that may be combined with any of the preceding embodiments, the herpes virus and/or pharmaceutical composition is administered topically, transdermally, subcutaneously, epicutaneously, intradermally, orally, sublingually, buccally, rectally, vaginally, intravenously, intraarterially, intramuscularly, intraosseously, intracardially, intraperitoneally, transmucosally, intravitreally, subretinally, intraarticularly, periarticularly, locally, or via inhalation to the subject. In some embodiments that may be combined with any of the preceding embodiments, the herpes virus and/or pharmaceutical composition is administered topically, transdermally, subcutaneously, intradermally, or transmucosally to the subject. In some embodiments that may be combined with any of the preceding embodiments, the herpes virus and/or pharmaceutical composition is administered topically, transdermally, or intradermally to the subject. In some embodiments that may be combined with any of the preceding embodiments, the herpes virus and/or pharmaceutical composition is administered topically or intradermally to the subject. In some embodiments that may be combined with any of the preceding embodiments, the herpes virus and/or pharmaceutical composition is administered intradermally to the subject. In some embodiments that may be combined with any of the preceding embodiments, the herpes virus and/or pharmaceutical composition is administered topically to the subject. In some embodiments that may be combined with any of the preceding embodiments, the skin of the subject is abraded prior to administration.

Other aspects of the present disclosure relate to a method of providing prophylactic, palliative, or therapeutic relief of one or more signs or symptoms of atopic dermatitis in a subject in need thereof comprising administering to the subject an effective amount of any of the herpes viruses described herein and/or any of the pharmaceutical compositions described herein. In some embodiments, the one or more signs or symptoms of atopic dermatitis are selected from itchy skin, dry skin, red to brownish-grey patches on the skin, small raised bumps on the skin, thickened skin, cracked skin, scaly skin, swollen skin, weeping sores, skin infections, eyelid dermatitis, cataracts, and any combinations thereof. In some embodiments that may be combined with any of the preceding embodiments, the subject is a human. In some embodiments that may be combined with any of the preceding embodiments, the subject's genome comprises a loss-of-function mutation in a SPINK5 gene. In some embodiments that may be combined with any of the preceding embodiments, the herpes virus and/or pharmaceutical composition is administered topically, transdermally, subcutaneously, epicutaneously, intradermally, orally, sublingually, buccally, rectally, vaginally, intravenously, intraarterially, intramuscularly, intraosseously, intracardially, intraperitoneally, transmucosally, intravitreally, subretinally, intraarticularly, periarticularly, locally, or via inhalation to the subject. In some embodiments that may be combined with any of the preceding embodiments, the herpes virus and/or pharmaceutical composition is administered topically, transdermally, subcutaneously, intradermally, or transmucosally to the subject. In some embodiments that may be combined with any of the preceding embodiments, the herpes virus and/or pharmaceutical composition is administered topically, transdermally, or intradermally to the subject. In some embodiments that may be combined with any of the preceding embodiments, the herpes virus and/or pharmaceutical composition is administered topically or intradermally to the subject. In some embodiments that may be combined with any of the preceding embodiments, the herpes virus and/or pharmaceutical composition is administered intradermally to the subject. In some embodiments that may be combined with any of the preceding embodiments, the herpes virus and/or pharmaceutical composition is administered topically to the subject. In some embodiments that may be combined with any of the preceding embodiments, the skin of the subject is abraded prior to administration.

Other aspects of the present disclosure relate to an article of manufacture or kit comprising any of the recombinant nucleic acids, viruses, medicaments, and/or pharmaceutical compositions or formulations described herein and instructions for administration thereof.

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 1A-I show schematics of wild-type and modified herpes simplex virus genomes. FIG. 1A shows a wild-type herpes simplex virus genome. FIG. 1B shows a modified herpes simplex virus genome comprising deletions of the coding sequence of ICP4 (both copies), with an expression cassette containing a nucleic acid encoding a human SPINK5 polypeptide integrated at each of the ICP4 loci. FIG. 1C shows a modified herpes simplex virus genome comprising deletions of the coding sequences of ICP4 (both copies) and ICP22, with an expression cassette containing a nucleic acid encoding a human SPINK5 polypeptide integrated at each of the ICP4 loci. FIG. 1D shows a modified herpes simplex virus genome comprising deletions of the coding sequences of ICP4 (both copies) and ICP22, with an expression cassette containing a nucleic acid encoding a human SPINK5 polypeptide integrated at the ICP22 locus. FIG. 1E shows a modified herpes simplex virus genome comprising deletions of the coding sequences of ICP4 (both copies) and UL41, with an expression cassette containing a nucleic acid encoding a human SPINK5 polypeptide integrated at each of the ICP4 loci. FIG. 1F shows a modified herpes simplex virus genome comprising deletions of the coding sequences of ICP4 (both copies) and UL41, with an expression cassette containing a nucleic acid encoding a human SPINK5 polypeptide integrated at the UL41 locus. FIG. 1G shows a modified herpes simplex virus genome comprising deletions of the coding sequences of ICP4 (both copies), ICP22, and UL41, with an expression cassette containing a nucleic acid encoding a human SPINK5 polypeptide integrated at each of the ICP4 loci. FIG. 1H shows a modified herpes simplex virus genome comprising deletions of the coding sequences of ICP4 (both copies), ICP22, and UL41, with an expression cassette containing a nucleic acid encoding a human SPINK5 polypeptide integrated at the UL41 locus. FIG. 1I shows a modified herpes simplex virus genome comprising deletions of the coding sequences of ICP4 (both copies), ICP22, and UL41, with an expression cassette containing a nucleic acid encoding a human SPINK5 polypeptide integrated at the ICP22 locus.

FIG. 2A shows the levels of codon-optimized human SPINK5 DNA present in immortalized normal keratinocytes 48 hours after infection with HSV-S5 at the indicated MOIs, as determined by qPCR analysis. FIG. 2B shows the levels of codon-optimized human SPINK5 transcripts present in immortalized normal keratinocytes 48 hours after infection with HSV-S5 at the indicated MOIs, as determined by qRT-PCR analysis. FIG. 2C shows western blot analysis of human SPINK5 protein expression in immortalized normal keratinocytes 48 hours after infection with HSV-S5 at the indicated MOIs. GAPDH was used as a loading control. FIG. 2D shows representative immunofluorescence images of human SPINK5 protein expression in immortalized normal keratinocytes 48 hours after infection with HSV-S5 at the indicated MOIs. DAPI staining was used to visualize nuclei. For all experiments, uninfected (mock) cells were used as a negative control.

FIG. 5A shows the levels of human SPINK5 DNA present in the skin of immunocompetent animals harvested 48 hours after topical application of HSV-S5 or vehicle control, as assessed by qPCR analysis. FIG. 5B shows the levels of human SPINK5 transcripts present in the skin of immunocompetent animals harvested 48 hours after topical application of HSV-S5 or vehicle control, as assessed by qRT-PCR analysis. FIG. 5C shows the levels of human SPINK5 DNA present in the skin of immunocompetent animals harvested 48 hours after intradermal injection of HSV-S5 or vehicle control, as assessed by qPCR analysis. FIG. 5D shows the levels of human SPINK5 transcripts present in the skin of immunocompetent animals harvested 48 hours after intradermal injection of HSV-S5 or vehicle control, as assessed by qRT-PCR analysis. For qPCR and qRT-PCR analyses, vehicle control data is presented as the average of two tissue samples (two replicates/tissue sample)±SEM, and HSV-S5 data is presented as the average of six tissue samples (two replicates/tissue sample)±SEM.

FIG. 5E shows representative immunofluorescence images of human SPINK5 and mouse filaggrin protein expression in skin biopsies harvested from BALB/c mice 48 hours after topical application of HSV-S5 or vehicle control. DAPI staining was used to visualize nuclei. FIG. 5F shows representative histology of mouse skin biopsies harvested from BALB/c mice 48 hours after topical application of HSV-S5 or vehicle control.

DETAILED DESCRIPTION

Figure 1C:
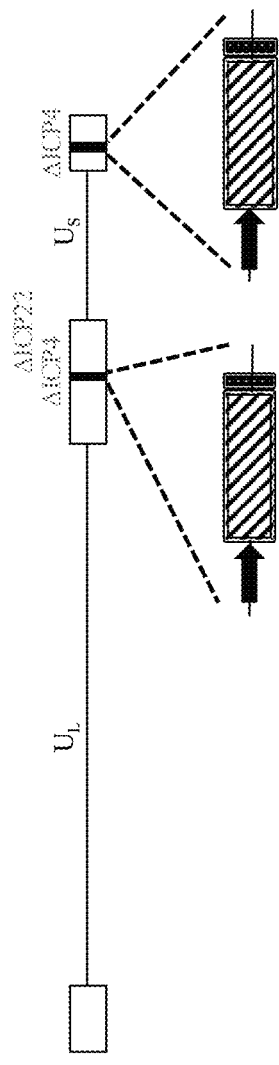

In some embodiments, the present disclosure relates to recombinant nucleic acids (e.g., recombinant herpes viral genomes) comprising one or more polynucleotides encoding a Serine Protease Inhibitor Kazal-type (SPINK) polypeptide (e.g., a human SPINK5 polypeptide), and/or use of these recombinant nucleic acids in viruses (e.g., herpes viruses), compositions, formulations, medicaments, and/or methods in order to supplement or treat SPINK gene deficiencies (e.g., in a subject whose genome naturally harbors a loss-of-function and/or pathogenic variant of a SPINK gene), and/or provide medical intervention to a subject in need thereof (e.g., to provide prophylactic, palliative, and/or therapeutic relief to one or more diseases or disorders arising from a SPINK gene deficiency (e.g., Netherton Syndrome, atopic dermatitis, etc.). Without wishing to be bound by theory, it is believed that the recombinant nucleic acids, viruses, compositions, formulations, medicaments, and/or methods described herein will help to treat the existing skin abnormalities in individuals suffering from Netherton Syndrome and/or atopic dermatitis, as well as prevent or delay reformation of skin abnormalities in treated subjects.

The following description sets forth exemplary methods, parameters, and the like. It should be recognized, however, that such description is not intended as a limitation on the scope of the present disclosure but is instead provided as a description of exemplary embodiments.

I. General Techniques

The techniques and procedures described or referenced herein are generally well understood and commonly employed using conventional methodology by those skilled in the art, such as, for example, the widely utilized methodologies described in Sambrook et al., 2001. *Molecular Cloning: A Laboratory Manual* 3d edition Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): *PCR 2: A Practical Approach* (M. J. MacPherson, B. D. Hames and G. R. Taylor eds. (1995)), Harlow and Lane, eds. (1988); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Gene Transfer Vectors for Mammalian Cells* (J. M. Miller and M. P. Calos, eds., 1987); *PCR: The Polymerase Chain Reaction*, (Mullis et al., eds., 1994); *Short Protocols in Molecular Biology* (Wiley and Sons, 1999).

II. Definitions

Before describing the present disclosure in detail, it is to be understood that the present disclosure is not limited to particular compositions or biological systems, which can, of course, vary. It is also to be understood that the terminology used herein is for the purpose of describing particular embodiments only and is not intended to be limiting.

As used herein, the singular forms "a", "an" and "the" include plural referents unless the content clearly dictates otherwise. Thus, for example, reference to "a molecule" optionally includes a combination of two or more such molecules, and the like.

As used herein, the term "and/or" may include any and all combinations of one or more of the associated listed items. For example, the term "a and/or b" may refer to "a alone", "b alone", "a or b", or "a and b"; the term "a, b, and/or c" may refer to "a alone", "b alone", "c alone", "a or b", "a or c", "b or c", "a, b, or c", "a and b", "a and c", "b and c", or "a, b, and c"; etc.

As used herein, the term "about" refers to the usual error range for the respective value readily known to the skilled person in this technical field. Reference to "about" a value or parameter herein includes (and describes) embodiments that are directed to that value or parameter per se.

It is understood that aspects and embodiments of the present disclosure include "comprising", "consisting", and "consisting essentially of" aspects and embodiments As used herein, the terms "polynucleotide", "nucleic acid sequence", "nucleic acid", and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing non-nucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally occurring nucleotides with an analog, and inter-nucleotide modifications.

As used herein, a nucleic acid is "operatively linked" or "operably linked" when it is placed into a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Generally, "operatively linked" or "operably linked" means that the DNA sequences being linked are contiguous.

As used herein, the term "vector" refers to discrete elements that are used to introduce heterologous nucleic acids into cells for either expression or replication thereof. An expression vector includes vectors capable of expressing nucleic acids that are operatively linked with regulatory sequences, such as promoter regions, that are capable of effecting expression of such nucleic acids. Thus, an expression vector may refer to a DNA or RNA construct, such as a plasmid, a phage, recombinant virus or other vector that, upon introduction into an appropriate host cell, results in expression of the nucleic acids. Appropriate expression vectors are well known to those of skill in the art and include those that are replicable in eukaryotic cells and those that remain episomal or those which integrate into the host cell genome.

As used herein, an "open reading frame" or "ORF" refers to a contiguous stretch of nucleic acids, either DNA or RNA, that encode a protein or polypeptide. Typically, the nucleic acid comprises a translation start signal or initiation codon, such as ATG or AUG, and a termination codon.

As used herein, an "untranslated region" or "UTR" refers to untranslated nucleic acids at the 5' and/or 3' ends of an open reading frame. The inclusion of one or more UTRs in a polynucleotide may affect post-transcriptional regulation, mRNA stability, and/or translation of the polynucleotide.

As used herein, the term "transgene" refers to a polynucleotide that is capable of being transcribed into RNA and translated and/or expressed under appropriate conditions, after being introduced into a cell. In some embodiments, it confers a desired property to a cell into which it was introduced, or otherwise leads to a desired therapeutic or diagnostic outcome.

As used herein, the terms "polypeptide," "protein," and "peptide" are used interchangeably and may refer to a polymer of two or more amino acids.

As used herein, a "subject", "host", or an "individual" refers to any animal classified as a mammal, including humans, domestic and farm animals, and zoo, sports, or pet animals, such as dogs, horses, cats, cows, as well as animals used in research, such as mice, rats, hamsters, rabbits, and non-human primates, etc. In some embodiments, the mammal is human.

As used herein, the terms "pharmaceutical formulation" or "pharmaceutical composition" refer to a preparation which is in such a form as to permit the biological activity of the active ingredient(s) to be effective, and which contains no additional components which are unacceptably toxic to a subject to which the composition or formulation would be administered. "Pharmaceutically acceptable" excipients (e.g., vehicles, additives) are those which can reasonably be administered to a subject mammal to provide an effective dose of the active ingredient(s) employed.

As used herein, an "effective amount" is at least the minimum amount required to affect a measurable improvement or prevention of one or more symptoms of a particular disorder. An "effective amount" may vary according to factors such as the disease state, age, sex, and weight of the patient. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications used to treat symptoms of the disease, delaying the progression of the disease, and/or prolonging survival. An effective amount can be administered in one or more administrations. For purposes of the present disclosure, an effective amount of a recombinant nucleic acid, virus, and/or pharmaceutical composition is an amount sufficient to accomplish prophylactic or therapeutic treatment either directly or indirectly. As is understood in the clinical context, an effective amount of a recombinant nucleic acid, virus, and/or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

As used herein, "treatment" refers to clinical intervention designed to alter the natural course of the individual or cell being treated during the course of clinical pathology. Desirable effects of treatment include decreasing the rate of disease/disorder/defect progression, ameliorating or palliating the disease/disorder/defect state, and remission or improved prognosis. For example, an individual is successfully "treated" if one or more symptoms associated with Netherton Syndrome and/or atopic dermatitis are mitigated or eliminated.

As used herein, the term "delaying progression of" a disease/disorder/defect refers to deferring, hindering, slowing, retarding, stabilizing, and/or postponing development of the disease/disorder/defect. This delay can be of varying lengths or time, depending on the history of the disease/disorder/defect and/or the individual being treated. As is evident to one of ordinary skill in the art, a sufficient or significant delay can, in effect, encompass prevention, in that the individual does not develop the disease.

III. Recombinant Nucleic Acids

Certain aspects of the present disclosure relate to recombinant nucleic acids (e.g., isolated recombinant nucleic acids) comprising one or more (e.g., one or more, two or more, three or more, four or more, five or more, ten or more, etc.) polynucleotides encoding a Serine Protease Inhibitor Kazal-type (SPINK) polypeptide. In some embodiments, the recombinant nucleic acid comprises one polynucleotide encoding a SPINK polypeptide. In some embodiments, the recombinant nucleic acid comprises two polynucleotides encoding a SPINK polypeptide. In some embodiments, the SPINK polypeptide is a human SPINK polypeptide. In some embodiments, the SPINK polypeptide is a Serine Protease Inhibitor Kazal-type 5 (SPINK5) polypeptide. In some embodiments, the SPINK5 polypeptide is a human SPINK5 polypeptide.

In some embodiments, the recombinant nucleic acid is a vector. In some embodiments, the recombinant nucleic acid is a viral vector. In some embodiments, the recombinant nucleic acid is a herpes viral vector. In some embodiments, the recombinant nucleic acid is a herpes simplex virus amplicon. In some embodiments, the recombinant nucleic acid is a recombinant herpes virus genome. In some embodiments, the recombinant nucleic acid is a recombinant herpes simplex virus genome. In some embodiments, the recombinant nucleic acid is a recombinant type 1 herpes simplex virus (HSV-1) genome.

Polynucleotides Encoding SPINK Polypeptides

In some embodiments, the present disclosure relates to a recombinant nucleic acid comprising one or more polynucleotides comprising the coding sequence of a SPINK gene, or portions thereof (e.g., the coding sequence corresponding to one or more Kazal-type domains resulting from proteolytic cleavage (e.g., via furin cleavage) of a full-length SPINK polypeptide). Any suitable SPINK gene (including any isoform thereof) known in the art may be encoded by a polynucleotide of the present disclosure, including, for example, a SPINK1 gene (e.g., a human SPINK1 gene (see e.g., NCBI Gene ID: 6690)), a SPINK2 gene (e.g., a human SPINK2 gene (see e.g., NCBI Gene ID: 6691)), a SPINK4 gene (e.g., a human SPINK4 gene (see e.g., NCBI Gene ID: 27920)), a SPINK5 gene (e.g., a human SPINK5 gene (see e.g., NCBI Gene ID: 11005)), a SPINK6 gene (e.g., a human SPINK6 gene (see e.g., NCBI Gene ID: 404203)), a SPINK7 gene (e.g., a human SPINK7 gene (see e.g., NCBI Gene ID: 84651)), a SPINK8 gene (e.g., a human SPINK8 gene (see e.g., NCBI Gene ID: 646424)), a SPINK9 gene (e.g., a human SPINK9 gene (see e.g., NCBI Gene ID: 643394)), a SPINK13 gene (e.g., a human SPINK13 gene (see e.g., NCBI Gene ID: 153218)), a SPINK14 gene (e.g., a human SPINK14 gene (see e.g., NCBI Gene ID: 408187)), etc. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of any SPINK gene (and/or coding sequences thereof) described herein or known in the art. Methods of identifying SPINK gene homologs/orthologs from additional species are known to one of ordinary skill in the art, including, for example, using a nucleic acid sequence alignment program such as the BLAST® blastn suite. In some embodiments, one or more polynucleotides of the present disclosure comprises the coding sequence of a human SPINK gene.

In some embodiments, a polynucleotide of the present disclosure comprises a codon-optimized variant of any SPINK gene described herein or known in the art. In some embodiments, use of a codon-optimized variant of a SPINK gene increases stability and/or yield of heterologous expression (RNA and/or protein) of the encoded SPINK polypeptide in a target cell (e.g., a target human cell such as a human keratinocyte or fibroblast), as compared to the stability and/or yield of heterologous expression of a corresponding non-codon-optimized, wild-type sequence. Any suitable method known in the art for performing codon optimization of a sequence for expression in one or more target cells (e.g., one or more human cells) may be used, including, for example, by the methods described by Fath et al. (PLoS One. 2011 Mar. 3; 6(3): e17596).

In some embodiments, the present disclosure relates to a recombinant nucleic acid comprising one or more polynucleotides comprising the coding sequence of a SPINK5 gene (e.g., a human SPINK5 gene), or portions thereof (e.g., the coding sequence corresponding to one or more Kazal-type domains resulting from proteolytic cleavage (e.g., via furin cleavage) of a full-length SPINK5 polypeptide). Any suitable SPINK5 gene (including any isoform thereof) known in the art may be encoded by a polynucleotide of the present disclosure, including, for example, a human SPINK5 gene (see e.g., NCBI Gene ID: 11005; SEQ ID NOS: 1, 3, or 5), a chimpanzee SPINK5 gene (see e.g., NCBI Gene ID: 462173), a mouse SPINK5 gene (see e.g., NCBI Gene ID: 72432), a rat SPINK5 gene (see e.g., NCBI Gene ID: 361319), a dog SPINK5 gene (see e.g., NCBI Gene ID: 478055), a cow SPINK5 gene (see e.g., NCBI Gene ID: 526637), a horse SPINK5 gene (see e.g., NCBI Gene ID: 100071873), a pig SPINK5 gene (see e.g., NCBI Gene ID: 100512160), etc. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of any SPINK5 gene (and/or the coding sequences thereof) described herein or known in the art. Methods of identifying SPINK5 gene homologs/orthologs from additional species are known to one of ordinary skill in the art, including, for example, using a nucleic acid sequence alignment program such as the BLAST® blastn suite.

In some embodiments, a polynucleotide of the present disclosure comprises a codon-optimized variant of any SPINK5 gene described herein or known in the art (see e.g., SEQ ID NOS: 2, 4, 6, or 26). In some embodiments, use of a codon-optimized variant of a SPINK5 gene (e.g., a codon-optimized variant of a human SPINK5 gene) increases stability and/or yield of heterologous expression (RNA and/or protein) of the encoded SPINK5 polypeptide in a target cell (e.g., a target human cell such as a human keratinocyte or fibroblast), as compared to the stability and/or yield of heterologous expression of a corresponding non-codon-optimized, wild-type sequence. Any suitable method known in the art for performing codon optimization of a sequence for expression in one or more target cells (e.g., one or more human cells) may be used, including, for example, by the methods described by Fath et al. (PLoS One. 2011 Mar. 3; 6(3): e17596).

In some embodiments, one or more polynucleotides of the present disclosure comprises the coding sequence of a human SPINK5 gene (or a codon-optimized variant thereof), or portions thereof (e.g., the coding sequence corresponding to one or more Kazal-type domains resulting from proteolytic cleavage (e.g., via human furin cleavage) of a full-length human SPINK5 polypeptide). In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to a sequence selected from SEQ ID NOS: 1-6 and 26. In some embodiments, a polynucleotide of the present disclosure comprises a sequence selected from SEQ ID NOS: 1-6 and 26. In some embodiments, a polynucleotide of the present disclosure comprises a sequence selected from SEQ ID NOS: 2, 4, 6, and 26.

In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 1 or SEQ ID NO: 2. In some embodiments, a polynucleotide of the present disclosure comprises the sequence of SEQ ID NO: 1 or SEQ ID NO: 2. In some embodiments, a polynucleotide of the present disclosure comprises the sequence of SEQ ID NO: 2.

In some embodiments, a polynucleotide of the present disclosure comprises a 5' truncation, a 3' truncation, or a fragment of the sequence of SEQ ID NO: 1 or SEQ ID NO: 2. In some embodiments, the 5' truncation, 3' truncation, or fragment of the sequence of SEQ ID NO: 1 or SEQ ID NO: 2 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, at least 1250, at least 1500, at least 1750, at least 2000, at least 2250, at least 2500, at least 2750, at least 3000, at least 3250, but fewer than 3285 consecutive nucleotides of SEQ ID NO: 1 or SEQ ID NO: 2. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-3282 of SEQ ID NO: 1 or SEQ ID NO: 2. In some embodiments, a polynucleotide of the present disclosure comprises the sequence of nucleic acids 1-3282 of SEQ ID NO: 1 or SEQ ID NO: 2.

In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 82-198 of SEQ ID NO: 1 or SEQ ID NO: 2. In some embodiments, a polynucleotide of the present disclosure comprises the sequence of nucleic acids 82-198 of SEQ ID NO: 1 or SEQ ID NO: 2.

In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 271-459 of SEQ ID NO: 1 or SEQ ID NO: 2. In some embodiments, a polynucleotide of the present disclosure comprises the sequence of nucleic acids 271-459 of SEQ ID NO: 1 or SEQ ID NO: 2.

In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 463-648 of SEQ ID NO: 1 or SEQ ID NO: 2. In some embodiments, a polynucleotide of the present disclosure comprises the sequence of nucleic acids 463-648 of SEQ ID NO: 1 or SEQ ID NO: 2.

In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 655-855 of SEQ ID NO: 1 or SEQ ID NO: 2. In some embodiments, a polynucleotide of the present disclosure comprises the sequence of nucleic acids 655-855 of SEQ ID NO: 1 or SEQ ID NO: 2.

In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 871-1056 of SEQ ID NO: 1 or SEQ ID NO: 2. In some embodiments, a polynucleotide of the present disclosure comprises the sequence of nucleic acids 871-1056 of SEQ ID NO: 1 or SEQ ID NO: 2.

In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1081-1269 of SEQ ID NO: 1 or SEQ ID NO: 2. In some embodiments, a polynucleotide of the present disclosure comprises the sequence of nucleic acids 1081-1269 of SEQ ID NO: 1 or SEQ ID NO: 2.

In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1291-1467 of SEQ ID NO: 1 or SEQ ID NO: 2. In some embodiments, a polynucleotide of the present disclosure comprises the sequence of nucleic acids 1291-1467 of SEQ ID NO: 1 or SEQ ID NO: 2.

In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1468-1653 of SEQ ID NO: 1 or SEQ ID NO: 2. In some embodiments, a polynucleotide of the present disclosure comprises the sequence of nucleic acids 1468-1653 of SEQ ID NO: 1 or SEQ ID NO: 2.

In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1681-1866 of SEQ ID NO: 1 or SEQ ID NO: 2. In some embodiments, a polynucleotide of the present disclosure comprises the sequence of nucleic acids 1681-1866 of SEQ ID NO: 1 or SEQ ID NO: 2.

In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1876-2064 of SEQ ID NO: 1 or SEQ ID NO: 2. In some embodiments, a polynucleotide of the present disclosure comprises the sequence of nucleic acids 1876-2064 of SEQ ID NO: 1 or SEQ ID NO: 2.

In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 2101-2271 of SEQ ID NO: 1 or SEQ ID NO: 2. In some embodiments, a polynucleotide of the present disclosure comprises the sequence of nucleic acids 2101-2271 of SEQ ID NO: 1 or SEQ ID NO: 2.

In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 2302-2490 of SEQ ID NO: 1 or SEQ ID NO: 2. In some embodiments, a polynucleotide of the present disclosure comprises the sequence of nucleic acids 2302-2490 of SEQ ID NO: 1 or SEQ ID NO: 2.

In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 2527-2715 of SEQ ID NO: 1 or SEQ ID NO: 2. In some embodiments, a polynucleotide of the present disclosure comprises the sequence of nucleic acids 2527-2715 of SEQ ID NO: 1 or SEQ ID NO: 2.

In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 2728-3003 of SEQ ID NO: 1 or SEQ ID NO: 2. In some embodiments, a polynucleotide of the present disclosure comprises the sequence of nucleic acids 2728-3003 of SEQ ID NO: 1 or SEQ ID NO: 2.

In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 3049-3234 of SEQ ID NO: 1 or SEQ ID NO: 2. In some embodiments, a polynucleotide of the present disclosure comprises the sequence of nucleic acids 3049-3234 of SEQ ID NO: 1 or SEQ ID NO: 2.

In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 3 or SEQ ID NO: 4. In some embodiments, a polynucleotide of the present disclosure comprises the sequence of SEQ ID NO: 3 or SEQ ID NO: 4. In some embodiments, a polynucleotide of the present disclosure comprises the sequence of SEQ ID NO: 4.

In some embodiments, a polynucleotide of the present disclosure comprises a 5' truncation, a 3' truncation, or a fragment of the sequence of SEQ ID NO: 3 or SEQ ID NO: 4. In some embodiments, the 5' truncation, 3' truncation, or fragment of the sequence of SEQ ID NO: 3 or SEQ ID NO: 4 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, at least 1250, at least 1500, at least 1750, at least 2000, at least 2250, at least 2500, at least 2750, but fewer than 2751 consecutive nucleotides of SEQ ID NO: 3 or SEQ ID NO: 4. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-2748 of SEQ ID NO: 3 or SEQ ID NO: 4. In some embodiments, a polynucleotide of the present disclosure comprises the sequence of nucleic acids 1-2748 of SEQ ID NO: 3 or SEQ ID NO: 4.

In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 5, SEQ ID NO: 6, or SEQ ID NO: 26. In some embodiments, a polynucleotide of the present disclosure comprises the sequence of SEQ ID NO: 5, SEQ ID NO: 6, or SEQ ID NO: 26. In some embodiments, a polynucleotide of the present disclosure comprises the sequence of SEQ ID NO: 6. In some embodiments, a polynucleotide of the present disclosure comprises the sequence of SEQ ID NO: 26.

In some embodiments, a polynucleotide of the present disclosure comprises a 5' truncation, a 3' truncation, or a fragment of the sequence of SEQ ID NO: 5, SEQ ID NO: 6, or SEQ ID NO: 26. In some embodiments, the 5' truncation, 3' truncation, or fragment of the sequence of SEQ ID NO: 5, SEQ ID NO: 6, or SEQ ID NO: 26 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, at least 1250, at least 1500, at least 1750, at least 2000, at least 2250, at least 2500, at least 2750, at least 3000, but fewer than 3195 consecutive nucleotides of SEQ ID NO: 5, SEQ ID NO: 6, or SEQ ID NO: 26. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-3192 of SEQ ID NO: 5, SEQ ID NO: 6, or SEQ ID NO: 26. In some embodiments, a polynucleotide of the present disclosure comprises the sequence of nucleic acids 1-3192 of SEQ ID NO: 5, SEQ ID NO: 6, or SEQ ID NO: 26.

A polynucleotide of the present disclosure encoding a SPINK polypeptide (e.g., a human SPINK5 polypeptide) may further encode additional coding and non-coding sequences. Examples of additional coding and non-coding sequences may include, but are not limited to, sequences encoding additional polypeptide tags (e.g., encoded in-frame with the SPINK protein in order to produce a fusion protein), introns (e.g., native, modified, or heterologous introns), 5' and/or 3' UTRs (e.g., native, modified, or heterologous 5' and/or 3' UTRs), and the like. Examples of suitable polypeptide tags may include, but are not limited, to any combination of purification tags, such as his-tags, flag-tags, maltose binding protein and glutathione-S-transferase tags, detection tags, such as tags that may be detected photometrically (e.g., green fluorescent protein, red fluorescent protein, etc.) and tags that have a detectable enzymatic activity (e.g., alkaline phosphatase, etc.), tags containing secretory sequences, signal sequences, leader sequences, and/or stabilizing sequences, protease cleavage sites (e.g., furin cleavage sites, TEV cleavage sites, Thrombin cleavage sites, etc.), and the like. In some embodiments, the 5' and/or 3'UTRs increase the stability, localization, and/or translational efficiency of the polynucleotides. In some embodiments, the 5' and/or 3'UTRs improve the level and/or duration of protein expression. In some embodiments, the 5' and/or 3'UTRs include elements (e.g., one or more miRNA binding sites, etc.) that may block or reduce off-target expression (e.g., inhibiting expression in specific cell types (e.g., neuronal cells), at specific times in the cell cycle, at specific developmental stages, etc.). In some embodiments, the 5' and/or 3'UTRs include elements (e.g., one or more miRNA binding sites, etc.) that may enhance effector protein expression in specific cell types (such as human keratinocytes and/or fibroblasts).

In some embodiments, a polynucleotide of the present disclosure is operably linked to one or more (e.g., one or more, two or more, three or more, four or more, five or more, ten or more, etc.) regulatory sequences. The term "regulatory sequence" may include enhancers, insulators, promoters, and other expression control elements (e.g., polyadenylation signals). Any suitable enhancer(s) known in the art may be used, including, for example, enhancer sequences from mammalian genes (such as globin, elastase, albumin, α-fetoprotein, insulin and the like), enhancer sequences from a eukaryotic cell virus (such as SV40 enhancer on the late side of the replication origin (bp 100-270), the cytomegalovirus early promoter enhancer, the polyoma enhancer on the late side of the replication origin, adenovirus enhancers, and the like), and any combinations thereof. Any suitable insulator(s) known in the art may be used, including, for example, herpes simplex virus (HSV) chromatin boundary (CTRL/CTCF-binding/insulator) elements CTRL1 and/or CTRL2, chicken hypersensitive site 4 insulator (cHS4), human HNRPA2B1-CBX3 ubiquitous chromatin opening element (UCOE), the scaffold/matrix attachment region (S/MAR) from the human interferon beta gene (IFNB1), and any combinations thereof. Any suitable promoter (e.g., suitable for transcription in mammalian host cells) known in the art may be used, including, for example, promoters obtained from the genomes of viruses (such as polyoma virus, fowlpox virus, adenovirus (such as Adenovirus 2), bovine papilloma virus, avian sarcoma virus, cytomegalovirus, a retrovirus, hepatitis-B virus, Simian Virus 40 (SV40), and the like), promoters from heterologous mammalian genes (such as the actin promoter (e.g., the β-actin promoter), a ubiquitin promoter (e.g., a ubiquitin C (UbC) promoter), a phosphoglycerate kinase (PGK) promoter, an immunoglobulin promoter, from heat-shock protein promoters, and the like), promoters from native and/or homologous mammalian genes (e.g., human SPINK gene promoters), synthetic promoters (such as the CAGG promoter), and any combinations thereof, provided such promoters are compatible with the host cells. Regulatory sequences may include those which direct constitutive expression of a nucleic acid, as well as tissue-specific regulatory and/or inducible or repressible sequences.

In some embodiments, a polynucleotide of the present disclosure is operably linked to one or more heterologous promoters. In some embodiments, the one or more heterologous promoters are one or more of constitutive promoters, tissue-specific promoters, temporal promoters, spatial promoters, inducible promoters and repressible promoters. In some embodiments, the one or more heterologous promoters are one or more of the human cytomegalovirus (HCMV) immediate early promoter, the human elongation factor-1 (EF1) promoter, the human β-actin promoter, the human UbC promoter, the human PGK promoter, the synthetic CAGG promoter, and any combinations thereof. In some embodiments, a polynucleotide of the present disclosure is operably linked to an HCMV promoter.

In some embodiments, a recombinant nucleic acid of the present disclosure does not comprise a polynucleotide comprising the coding sequence of (e.g., a transgene encoding) a Collagen alpha-1 (VII) chain polypeptide (COL7). In some embodiments, a recombinant nucleic acid of the present disclosure does not comprise a polynucleotide comprising the coding sequence of (e.g., a transgene encoding) a Lysyl hydroxylase 3 polypeptide (LH3). In some embodiments, a recombinant nucleic acid of the present disclosure does not comprise a polynucleotide comprising the coding sequence of (e.g., a transgene encoding) a Keratin type I cytoskeletal 17 polypeptide (KRT17). In some embodiments, a recombinant nucleic acid of the present disclosure does not comprise a polynucleotide comprising the coding sequence of (e.g., a transgene encoding) a transglutaminase (TGM) polypeptide (e.g., a human transglutaminase polypeptide such as a human TGM1 polypeptide). In some embodiments, a recombinant nucleic acid of the present disclosure does not comprise a polynucleotide comprising the coding sequence of (e.g., a transgene encoding) a cosmetic protein (e.g., collagen proteins, fibronectins, elastins, lumicans, vitronectins/vitronectin receptors, laminins, neuromodulators, fibrillins, additional dermal extracellular matrix proteins, etc.). In some embodiments, a recombinant nucleic acid of the present disclosure does not comprise a polynucleotide comprising the coding sequence of (e.g., a transgene encoding) an antibody (e.g., a full-length antibody, an antibody fragments, etc.). In some embodiments, a recombinant nucleic acid of the present disclosure does not comprise a polynucleotide comprising the coding sequence of (e.g., a transgene encoding) a Collagen alpha-1 (VII) chain polypeptide, a Lysyl hydroxylase 3 polypeptide, a Keratin type I cytoskeletal 17 polypeptide, and/or any chimeric polypeptides thereof. In some embodiments, a recombinant nucleic acid of the present disclosure does not comprise a polynucleotide comprising the coding sequence of (e.g., a transgene encoding) a Collagen alpha-1 (VII) chain polypeptide, a Lysyl hydroxylase 3 polypeptide, a Keratin type I cytoskeletal 17 polypeptide, a transglutaminase (TGM) polypeptide, a cosmetic protein, an antibody, and/or any chimeric polypeptides thereof.

SPINK Polypeptides

In some embodiments, the present disclosure relates to one or more polynucleotides encoding a SPINK polypeptide, or any portions thereof (e.g., the amino acid sequence of one or more Kazal-type domains resulting from proteolytic cleavage (e.g., via furin cleavage) of a full-length SPINK polypeptide). Any suitable SPINK polypeptide (or portions thereof) known in the art may be encoded by a polynucleotide of the present disclosure, including, for example, a SPINK1 polypeptide (e.g., a human SPINK1 polypeptide (see e.g., UniProt accession number: P00995)), a SPINK2 polypeptide (e.g., a human SPINK2 polypeptide (see e.g., UniProt accession number: P20155)), a SPINK4 polypeptide (e.g., a human SPINK4 polypeptide (see e.g., UniProt accession number: O60575)), a SPINK5 polypeptide (e.g., a human SPINK5 polypeptide (see e.g., UniProt accession number: Q9NQ38)), a SPINK6 polypeptide (e.g., a human SPINK6 polypeptide (see e.g., UniProt accession number: Q6UWN8)), a SPINK7 polypeptide (e.g., a human SPINK7 polypeptide (see e.g., UniProt accession number: P58062)), a SPINK8 polypeptide (e.g., a human SPINK8 polypeptide (see e.g., UniProt accession number: P0C7L1)), a SPINK9 polypeptide (e.g., a human SPINK9 polypeptide (see e.g., UniProt accession number: Q5DT21)), a SPINK13 polypeptide (e.g., a human SPINK13 polypeptide (see e.g., UniProt accession number: Q1W4C9)), a SPINK14 polypeptide (e.g., a human SPINK14 polypeptide (see e.g., UniProt accession number: Q6IE38)), etc. In some embodiments, a SPINK polypeptide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of any SPINK polypeptide described herein or known in the art. Methods of identifying SPINK polypeptide homologs/orthologs from additional species are known to one of ordinary skill in the art, including, for example, using an amino acid sequence alignment program such as the BLAST® blastp suite or OrthoDB. In some embodiments, the SPINK polypeptide is a human SPINK polypeptide.

In some embodiments, the present disclosure relates to one or more polynucleotides encoding a SPINK5 polypeptide (e.g., SEQ ID NOS: 7-9), or any portions thereof (e.g., the amino acid sequence of one or more Kazal-type domains resulting from proteolytic cleavage (e.g., via furin cleavage) of a full-length SPINK5 polypeptide (e.g., SEQ ID NOS: 10-25)). Any suitable SPINK5 polypeptide (or portions thereof) known in the art may be encoded by a polynucleotide of the present disclosure, including, for example, a human SPINK5 polypeptide (see e.g., UniProt accession number: 11005), a chimpanzee SPINK5 polypeptide (see e.g., UniProt accession number: 462173), a mouse SPINK5 polypeptide (see e.g., UniProt accession number: Q5K5D4), a rat SPINK5 polypeptide (see e.g., UniProt accession number: D3ZET2), a dog SPINK5 polypeptide (see e.g., UniProt accession number: F1PR80), a cow SPINK5 polypeptide (see e.g., UniProt accession number: F1MJH0), a horse SPINK5 polypeptide (see e.g., UniProt accession number: B9VJ40), a pig SPINK5 polypeptide (see e.g., UniProt accession number: F1RLZ2), etc. In some embodiments, a SPINK5 polypeptide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of any SPINK5 polypeptide described herein or known in the art. Methods of identifying SPINK5 polypeptide homologs/orthologs from additional species are known to one of ordinary skill in the art, including, for example, using an amino acid sequence alignment program such as the BLAST® blastp suite or OrthoDB.

In some embodiments, a SPINK5 polypeptide of the present disclosure is a human SPINK5 polypeptide, or portions thereof (e.g., a polypeptide comprising the amino acid sequence corresponding to one or more Kazal-type domains resulting from proteolytic cleavage (e.g., via human furin cleavage) of a full-length human SPINK5 polypeptide). In some embodiments, a polynucleotide encoding a human SPINK5 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a sequence selected from SEQ ID NOS: 7-25. In some embodiments, a polynucleotide encoding a human SPINK5 polypeptide is a polynucleotide that encodes a polypeptide comprising an amino acid sequence selected from SEQ ID NOS: 7-25. In some embodiments, a polynucleotide encoding a human SPINK5 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a sequence selected from SEQ ID NOS: 7-9. In some embodiments, a polynucleotide encoding a human SPINK5 polypeptide is a polynucleotide that encodes a polypeptide comprising an amino acid sequence selected from SEQ ID NOS: 7-9.

In some embodiments, a SPINK5 polypeptide of the present disclosure comprises, consists essentially of, or consists of a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 7-25. In some embodiments, a SPINK5 polypeptide of the present disclosure comprises, consists essentially of, or consists of a sequence selected from SEQ ID NOS: 7-25. In some embodiments, a SPINK5 polypeptide of the present disclosure comprises, consists essentially of, or consists of a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 7-9. In some embodiments, a SPINK5 polypeptide of the present disclosure comprises, consists essentially of, or consists of a sequence selected from SEQ ID NOS: 7-9.

In some embodiments, a polynucleotide encoding a human SPINK5 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 7. In some embodiments, a polynucleotide encoding a human SPINK5 polypeptide is a polynucleotide that encodes a polypeptide comprising the amino acid sequence of SEQ ID NO: 7.

In some embodiments, a polynucleotide encoding a human SPINK5 polypeptide is a polynucleotide that encodes an N-terminal truncation, a C-terminal truncation, or a fragment of the amino acid sequence of SEQ ID NO: 7. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 600, at least 700, at least 800, at least 900, at least 1000, but fewer than 1094, consecutive amino acids of SEQ ID NO: 7.

In some embodiments, a polynucleotide encoding a human SPINK5 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 8. In some embodiments, a polynucleotide encoding a human SPINK5 polypeptide is a polynucleotide that encodes a polypeptide comprising the amino acid sequence of SEQ ID NO: 8.

In some embodiments, a polynucleotide encoding a human SPINK5 polypeptide is a polynucleotide that encodes an N-terminal truncation, a C-terminal truncation, or a fragment of the amino acid sequence of SEQ ID NO: 8. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 600, at least 700, at least 800, at least 900, but fewer than 916, consecutive amino acids of SEQ ID NO: 8.

In some embodiments, a polynucleotide encoding a human SPINK5 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 9. In some embodiments, a polynucleotide encoding a human SPINK5 polypeptide is a polynucleotide that encodes a polypeptide comprising the amino acid sequence of SEQ ID NO: 9.

In some embodiments, a polynucleotide encoding a human SPINK5 polypeptide is a polynucleotide that encodes an N-terminal truncation, a C-terminal truncation, or a fragment of the amino acid sequence of SEQ ID NO: 9. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 600, at least 700, at least 800, at least 900, at least 1000, but fewer than 1064, consecutive amino acids of SEQ ID NO: 9.

In some embodiments, a polynucleotide of the present disclosure encodes a Kazal-type domain derived from a human SPINK5 polypeptide (e.g., a Kazal-type domain resulting from proteolytic cleavage (e.g., via furin cleavage) of human SPINK5).

In some embodiments, a SPINK5 polypeptide of the present disclosure comprises or consists of an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 10. In some embodiments, a SPINK5 polypeptide of the present disclosure comprises or consists of the amino acid sequence of SEQ ID NO: 10.

In some embodiments, a SPINK5 polypeptide of the present disclosure comprises or consists of an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 11. In some embodiments, a SPINK5 polypeptide of the present disclosure comprises or consists of the amino acid sequence of SEQ ID NO: 11.

In some embodiments, a SPINK5 polypeptide of the present disclosure comprises or consists of an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 12. In some embodiments, a SPINK5 polypeptide of the present disclosure comprises or consists of the amino acid sequence of SEQ ID NO: 12.

In some embodiments, a SPINK5 polypeptide of the present disclosure comprises or consists of an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 13. In some embodiments, a SPINK5 polypeptide of the present disclosure comprises or consists of the amino acid sequence of SEQ ID NO: 13.

In some embodiments, a SPINK5 polypeptide of the present disclosure comprises or consists of an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 14. In some embodiments, a SPINK5 polypeptide of the present disclosure comprises or consists of the amino acid sequence of SEQ ID NO: 14.

In some embodiments, a SPINK5 polypeptide of the present disclosure comprises or consists of an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 15.

In some embodiments, a SPINK5 polypeptide of the present disclosure comprises or consists of the amino acid sequence of SEQ ID NO: 15.

In some embodiments, a SPINK5 polypeptide of the present disclosure comprises or consists of an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 16. In some embodiments, a SPINK5 polypeptide of the present disclosure comprises or consists of the amino acid sequence of SEQ ID NO: 16.

In some embodiments, a SPINK5 polypeptide of the present disclosure comprises or consists of an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 17. In some embodiments, a SPINK5 polypeptide of the present disclosure comprises or consists of the amino acid sequence of SEQ ID NO: 17.

In some embodiments, a SPINK5 polypeptide of the present disclosure comprises or consists of an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 18. In some embodiments, a SPINK5 polypeptide of the present disclosure comprises or consists of the amino acid sequence of SEQ ID NO: 18.

In some embodiments, a SPINK5 polypeptide of the present disclosure comprises or consists of an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 19. In some embodiments, a SPINK5 polypeptide of the present disclosure comprises or consists of the amino acid sequence of SEQ ID NO: 19.

In some embodiments, a SPINK5 polypeptide of the present disclosure comprises or consists of an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 20. In some embodiments, a SPINK5 polypeptide of the present disclosure comprises or consists of the amino acid sequence of SEQ ID NO: 20.

In some embodiments, a SPINK5 polypeptide of the present disclosure comprises or consists of an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 21. In some embodiments, a SPINK5 polypeptide of the present disclosure comprises or consists of the amino acid sequence of SEQ ID NO: 21.

In some embodiments, a SPINK5 polypeptide of the present disclosure comprises or consists of an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 22. In some embodiments, a SPINK5 polypeptide of the present disclosure comprises or consists of the amino acid sequence of SEQ ID NO: 22.

In some embodiments, a SPINK5 polypeptide of the present disclosure comprises or consists of an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 23. In some embodiments, a SPINK5 polypeptide of the present disclosure comprises or consists of the amino acid sequence of SEQ ID NO: 23.

In some embodiments, a SPINK5 polypeptide of the present disclosure comprises or consists of an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 24. In some embodiments, a SPINK5 polypeptide of the present disclosure comprises or consists of the amino acid sequence of SEQ ID NO: 24.

In some embodiments, a SPINK5 polypeptide of the present disclosure comprises or consists of an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 25. In some embodiments, a SPINK5 polypeptide of the present disclosure comprises or consists of the amino acid sequence of SEQ ID NO: 25.

In some embodiments, a polynucleotide of the present disclosure encoding a SPINK polypeptide (e.g., a SPINK5 polypeptide) expresses the SPINK polypeptide when the polynucleotide is delivered into one or more target cells of a subject. In some embodiments, expression of the SPINK polypeptide (e.g., a SPINK5 polypeptide) enhances, increases, augments, and/or supplements the levels, function, and/or activity of a SPINK polypeptide in one or more target cells of a subject (e.g., as compared to prior to expression of the exogenous SPINK polypeptide). In some embodiments, expression of the SPINK polypeptide (e.g., a SPINK5 polypeptide) enhances, increases, augments, and/or supplements the anti-inflammatory and/or anti-microbial protection of mucous epithelia in the subject. In some embodiments, expression of the SPINK polypeptide (e.g., a SPINK5 polypeptide) enhances, increases, augments, and/or supplements the integrity and/or protective barrier function of the skin of the subject. In some embodiments, expression of the SPINK polypeptide (e.g., a SPINK5 polypeptide) decreases, augments, and/or inhibits one or more of Kallikrein-5 (KLK5), Kallikrein-7 (KLK7), Kallikrein-14 (KLK14), Caspase-14 (CASP14) and/or trypsin in the subject (e.g., decreases, augments, and/or inhibits one or more activities of KLK5, KLK7, KLK14, CASP14, and/or trypsin).

Recombinant Nucleic Acids

In some embodiments, the present disclosure relates to recombinant nucleic acids comprising any one or more of the polynucleotides described herein. In some embodiments, the recombinant nucleic acid is a vector (e.g., an expression vector, a display vector, etc.). In some embodiments, the vector is a DNA vector or an RNA vector. Generally, vectors suitable to maintain, propagate, and/or express polynucleotides to produce one or more polypeptides in a subject may be used. Examples of suitable vectors may include, for example, plasmids, cosmids, episomes, transposons, and viral vectors (e.g., adenoviral vectors, adeno-associated viral vectors, vaccinia viral vectors, Sindbis-viral vectors, measles vectors, herpes viral vectors, lentiviral vectors, retroviral vectors, etc.). In some embodiments, the vector is a herpes viral vector. In some embodiments, the vector is capable of autonomous replication in a host cell. In some embodiments, the vector is incapable of autonomous replication in a host cell. In some embodiments, the vector can integrate into a host DNA. In some embodiments, the vector cannot integrate into a host DNA (e.g., is episomal). Methods of making vectors containing one or more polynucleotides of interest are well known to one of ordinary skill in the art, including, for example, by chemical synthesis or by artificial manipulation of isolated segments of nucleic acids (e.g., by genetic engineering techniques).

In some embodiments, a recombinant nucleic acid of the present disclosure is a herpes simplex virus (HSV) amplicon. Herpes virus amplicons, including the structural features and methods of making the same, are generally known to one of ordinary skill in the art (see e.g., de Silva S. and Bowers W. "Herpes Virus Amplicon Vectors". *Viruses* 2009, 1, 594-629). In some embodiments, the herpes simplex virus amplicon is an HSV-1 amplicon. In some embodiments, the herpes simplex virus amplicon is an HSV-1 hybrid amplicon. Examples of HSV-1 hybrid amplicons may include, but are not limited to, HSV/AAV hybrid amplicons, HSV/EBV hybrid amplicons, HSV/EBV/RV hybrid amplicons, and/or HSV/Sleeping Beauty hybrid amplicons. In some embodiments, the amplicon is an HSV/AAV hybrid amplicon. In some embodiments, the amplicon is an HSV/Sleeping Beauty hybrid amplicon.

In some embodiments, a recombinant nucleic acid of the present disclosure is a recombinant herpes virus genome. The recombinant herpes virus genome may be a recombinant genome from any member of the Herpesviridae family of DNA viruses known in the art, including, for example, a recombinant herpes simplex virus genome, a recombinant varicella zoster virus genome, a recombinant human cytomegalovirus genome, a recombinant herpesvirus 6A genome, a recombinant herpesvirus 6B genome, a recombinant herpesvirus 7 genome, a recombinant Kaposi's sarcoma-associated herpesvirus genome, and any combinations or derivatives thereof. In some embodiments, the recombinant herpes virus genome comprises one or more (e.g., one or more, two or more, three or more, four or more, five or more, six or more, seven or more, eight or more, nine or more, ten or more, etc.) inactivating mutations. In some embodiments, the one or more inactivating mutations are in one or more (e.g., one or more, two or more, three or more, four or more, five or more, six or more, seven or more, eight or more, nine or more, ten or more, etc.) herpes virus genes. In some embodiments, the recombinant herpes virus genome is attenuated (e.g., as compared to a corresponding, wild-type herpes virus genome). In some embodiments, the recombinant herpes virus genome is replication competent. In some embodiments, the recombinant herpes virus genome is replication defective.

In some embodiments, the recombinant nucleic acid is a recombinant herpes simplex virus (HSV) genome. In some embodiments, the recombinant herpes simplex virus genome is a recombinant type 1 herpes simplex virus (HSV-1) genome, a recombinant type 2 herpes simplex virus (HSV-2)

genome, or any derivatives thereof. In some embodiments, the recombinant herpes simplex virus genome is a recombinant HSV-1 genome. In some embodiments, the recombinant HSV-1 genome may be from any HSV-1 strain known in the art, including, for example, strains 17, Ty25, R62, S25, Ku86, S23, R11, Ty148, Ku47, H166syn, 1319-2005, F-13, M-12, 90237, F-17, KOS, 3083-2008, F12g, L2, CD38, H193, M-15, India 2011, 0116209, F-11I, 66-207, 2762, 369-2007, 3355, MacIntyre, McKrae, 7862, 7-hse, HF10, 1394,2005, 270-2007, OD4, SC16, M-19, 4J1037, 5J1060, J1060, KOS79, 132-1988, 160-1982, H166, 2158-2007, RE, 78326, F18g, F11, 172-2010, H129, F, E4, CJ994, F14g, E03, E22, E10, E06, E11, E25, E23, E35, E15, E07, E12, E14, E08, E19, E13, ATCC 2011, etc. (see e.g., Bowen et al. J Virol. 2019 Apr. 3; 93(8)). In some embodiments, the recombinant HSV-1 genome is from the KOS strain. In some embodiments, the recombinant HSV-1 genome is not from the McKrae strain. In some embodiments, the recombinant herpes simplex virus genome is attenuated. In some embodiments, the recombinant herpes simplex virus genome is replication competent. In some embodiments, the recombinant herpes simplex virus genome is replication defective. In some embodiments, the recombinant herpes simplex virus genome comprises one or more (e.g., one or more, two or more, three or more, four or more, five or more, six or more, seven or more, eight or more, nine or more, ten or more, etc.) inactivating mutations. In some embodiments, the one or more inactivating mutations are in one or more (e.g., one or more, two or more, three or more, four or more, five or more, six or more, seven or more, eight or more, nine or more, ten or more, etc.) herpes simplex virus genes. As used herein, an "inactivating mutation" may refer to any mutation that results in a gene or regulon product (RNA or protein) having reduced, undetectable, or eliminated quantity and/or function (e.g., as compared to a corresponding sequence lacking the inactivating mutation). Examples of inactivating mutations may include, but are not limited to, deletions, insertions, point mutations, and rearrangements in transcriptional control sequences (promoters, enhancers, insulators, etc.) and/or coding sequences of a given gene or regulon. Any suitable method of measuring the quantity of a gene or regulon product known in the art may be used, including, for example, qPCR, Northern blots, RNAseq, western blots, ELISAs, etc.

In some embodiments, the recombinant herpes simplex virus genome comprises an inactivating mutation in at least one, at least two, at least three, at least four, at least five, at least six, at least seven, or all eight of the Infected Cell Protein (or Infected Cell Polypeptide) (ICP) 0, ICP4, ICP22, ICP27, ICP47, thymidine kinase (tk), Long Unique Region (UL) 41 and/or UL55 herpes simplex virus genes. In some embodiments, the recombinant herpes simplex virus genome does not comprise an inactivating mutation in the ICP34.5 (one or both copies) and/or ICP47 herpes simplex virus genes (e.g., to avoid production of an immune-stimulating virus). In some embodiments, the recombinant herpes simplex virus genome does not comprise an inactivating mutation in the ICP34.5 (one or both copies) herpes simplex virus gene. In some embodiments, the recombinant herpes simplex virus genome does not comprise an inactivating mutation in the ICP47 herpes simplex virus gene. In some embodiments, the recombinant herpes simplex virus genome does not comprise an inactivating mutation in the ICP34.5 (one or both copies) and ICP47 herpes simplex virus genes. In some embodiments, the recombinant herpes simplex virus genome is not oncolytic.

In some embodiments, the recombinant herpes simplex virus genome comprises an inactivating mutation in the ICP0 gene (one or both copies). In some embodiments, the recombinant herpes simplex virus genome comprises an inactivating mutation in the ICP0 gene (one or both copies), and further comprises an inactivating mutation in the ICP4 (one or both copies), ICP22, ICP27, ICP47, UL41, and/or UL55 genes. In some embodiments, the recombinant herpes simplex virus genome comprises an inactivating mutation in the ICP0 gene (one or both copies), and an inactivating mutation in the ICP4 gene (one or both copies). In some embodiments, the recombinant herpes simplex virus genome comprises an inactivating mutation in the ICP0 gene (one or both copies), and an inactivating mutation in the ICP22 gene. In some embodiments, the recombinant herpes simplex virus genome comprises an inactivating mutation in the ICP0 gene (one or both copies), and an inactivating mutation in the UL41 gene. In some embodiments, the recombinant herpes simplex virus genome comprises an inactivating mutation in the ICP0 gene (one or both copies), an inactivating mutation in the ICP4 gene (one or both copies), and an inactivating mutation in the ICP22 gene. In some embodiments, the recombinant herpes simplex virus genome comprises an inactivating mutation in the ICP0 gene (one or both copies), an inactivating mutation in the ICP4 gene (one or both copies), and an inactivating mutation in the UL41 gene. In some embodiments, the recombinant herpes simplex virus genome comprises an inactivating mutation in the ICP0 gene (one or both copies), an inactivating mutation in the ICP22 gene, and an inactivating mutation in the UL41 gene. In some embodiments, the recombinant herpes simplex virus genome comprises an inactivating mutation in the ICP0 gene (one or both copies), an inactivating mutation in the ICP4 gene (one or both copies), an inactivating mutation in the ICP22 gene, and an inactivating mutation in the UL41 gene. In some embodiments, the inactivating mutation is a deletion of the coding sequence of the ICP0 (one or both copies), ICP4 (one or both copies), ICP22, and/or UL41 genes. In some embodiments, the recombinant herpes simplex virus genome further comprises an inactivating mutation in the ICP27, ICP47, and/or UL55 genes.

In some embodiments, the recombinant herpes simplex virus genome comprises an inactivating mutation in the ICP4 gene (one or both copies). In some embodiments, the recombinant herpes simplex virus genome comprises an inactivating mutation in the ICP4 gene (one or both copies), and further comprises an inactivating mutation in the ICP0 (one or both copies), ICP22, ICP27, ICP47, UL41, and/or UL55 genes. In some embodiments, the recombinant herpes simplex virus genome comprises an inactivating mutation in the ICP4 gene (one or both copies), and an inactivating mutation in the ICP22 gene. In some embodiments, the recombinant herpes simplex virus genome comprises an inactivating mutation in the ICP4 gene (one or both copies), and an inactivating mutation in the UL41 gene. In some embodiments, the recombinant herpes simplex virus genome comprises an inactivating mutation in the ICP4 gene (one or both copies), an inactivating mutation in the ICP22 gene, and an inactivating mutation in the UL41 gene. In some embodiments, the inactivating mutation is a deletion of the coding sequence of the ICP4 (one or both copies), ICP22, and/or UL41 genes. In some embodiments, the recombinant herpes simplex virus genome further comprises an inactivating mutation in the ICP0 (one or both copies), ICP27, ICP47, and/or UL55 genes.

In some embodiments, the recombinant herpes simplex virus genome comprises an inactivating mutation in the ICP22 gene. In some embodiments, the recombinant herpes simplex virus genome comprises an inactivating mutation in the ICP22 gene, and further comprises an inactivating mutation in the ICP0 (one or both copies), ICP4 (one or both copies), ICP27, ICP47, UL41, and/or UL55 genes. In some embodiments, the recombinant herpes simplex virus genome comprises an inactivating mutation in the ICP22 gene, and an inactivating mutation UL41 gene. In some embodiments, the inactivating mutation is a deletion of the coding sequence of the ICP22 and/or UL41 genes. In some embodiments, the recombinant herpes simplex virus genome further comprises an inactivating mutation in the ICP0 (one or both copies), ICP4 (one or both copies), ICP27, ICP47, and/or UL55 genes.

In some embodiments, the recombinant herpes simplex virus genome comprises an inactivating mutation in the ICP27 gene. In some embodiments, the recombinant herpes simplex virus genome comprises an inactivating mutation in the ICP27 gene, and further comprises an inactivating mutation in the ICP0 (one or both copies), ICP4 (one or both copies), ICP22, ICP47, UL41, and/or UL55 genes. In some embodiments, the inactivating mutation is a deletion of the coding sequence of the ICP27 gene.

In some embodiments, the recombinant herpes simplex virus genome comprises an inactivating mutation in the ICP47 gene. In some embodiments, the recombinant herpes simplex virus genome comprises an inactivating mutation in the ICP47 gene, and further comprises an inactivating mutation in the ICP0 (one or both copies), ICP4 (one or both copies), ICP22, ICP27, UL41, and/or UL55 genes. In some embodiments, the inactivating mutation is a deletion of the coding sequence of the ICP47 gene.

In some embodiments, the recombinant herpes simplex virus genome comprises an inactivating mutation in the UL41 gene. In some embodiments, the recombinant herpes simplex virus genome comprises an inactivating mutation in the UL41 gene, and further comprises an inactivating mutation in the ICP0 (one or both copies), ICP4 (one or both copies), ICP22, ICP27, ICP47, and/or UL55 genes. In some embodiments, the inactivating mutation is a deletion of the coding sequence of the UL41 gene.

In some embodiments, the recombinant herpes simplex virus genome comprises an inactivating mutation in the UL55 gene. In some embodiments, the recombinant herpes simplex virus genome comprises an inactivating mutation in the UL55 gene, and further comprises an inactivating mutation in the ICP0 (one or both copies), ICP4 (one or both copies), ICP22, ICP27, ICP47, and/or UL41 genes. In some embodiments, the inactivating mutation is a deletion of the coding sequence of the UL55 gene.

In some embodiments, the recombinant herpes simplex virus genome comprises an inactivating mutation in (e.g., a deletion of) the internal repeat (Joint) region comprising the internal repeat long (IRL) and internal repeat short (IRs) regions. In some embodiments, inactivation (e.g., deletion) of the Joint region eliminates one copy each of the ICP4 and ICP0 genes. In some embodiments, inactivation (e.g., deletion) of the Joint region further inactivates (e.g., deletes) the promoter for the ICP22 and ICP47 genes. If desired, expression of one or both of these genes can be restored by insertion of an immediate early promoter into the recombinant herpes simplex virus genome (see e.g., Hill et al. (1995). Nature 375(6530): 411-415; Goldsmith et al. (1998). J Exp Med 187(3): 341-348). Without wishing to be bound by theory, it is believed that inactivating (e.g., deleting) the Joint region may contribute to the stability of the recombinant herpes simplex virus genome and/or allow for the recombinant herpes simplex virus genome to accommodate more and/or larger transgenes.

In some embodiments, the recombinant herpes simplex virus genome comprises an inactivating mutation in the ICP4 (one or both copies), ICP22, and ICP27 genes. In some embodiments, the recombinant herpes simplex virus genome comprises an inactivating mutation in the ICP4 (one or both copies), ICP27, and UL55 genes. In some embodiments, the recombinant herpes simplex virus genome comprises an inactivating mutation in the ICP4 (one or both copies), ICP22, ICP27, ICP47, and UL55 genes. In some embodiments, the inactivating mutation in the ICP4 (one or both copies), ICP27, and/or UL55 genes is a deletion of the coding sequence of the ICP4 (one or both copies), ICP27, and/or UL55 genes. In some embodiments, the inactivating mutation in the ICP22 and ICP47 genes is a deletion in the promoter region of the ICP22 and ICP47 genes (e.g., the ICP22 and ICP47 coding sequences are intact but are not transcriptionally active). In some embodiments, the recombinant herpes simplex virus genome comprises a deletion in the coding sequence of the ICP4 (one or both copies), ICP27, and UL55 genes, and a deletion in the promoter region of the ICP22 and ICP47 genes. In some embodiments, the recombinant herpes simplex virus genome further comprises an inactivating mutation in the ICP0 (one or both copies) and/or UL41 genes.

In some embodiments, the recombinant herpes simplex virus genome comprises an inactivating mutation in the ICP0 (one or both copies) and ICP4 (one or both copies) genes. In some embodiments, the recombinant herpes simplex virus genome comprises an inactivating mutation in the ICP0 (one or both copies), ICP4 (one or both copies), and ICP22 genes. In some embodiments, the recombinant herpes simplex virus genome comprises an inactivating mutation in the ICP0 (one or both copies), ICP4 (one or both copies), ICP22, and ICP27 genes. In some embodiments, the recombinant herpes simplex virus genome comprises an inactivating mutation in the ICP0 (one or both copies), ICP4 (one or both copies), ICP22, ICP27 and UL55 genes. In some embodiments, the inactivating mutation in the ICP0 (one or both copies), ICP4 (one or both copies), ICP22, ICP27 and/or UL55 genes comprises a deletion of the coding sequence of the ICP0 (one or both copies), ICP4 (one or both copies), ICP22, ICP27 and/or UL55 genes. In some embodiments, the recombinant herpes simplex virus genome further comprises an inactivating mutation in the ICP47 and/or the UL41 genes.

In some embodiments, a recombinant herpes simplex virus genome comprises one or more polynucleotides of the present disclosure within one, two, three, four, five, six, seven or more viral gene loci. Examples of suitable viral loci may include, without limitation, the ICP0 (one or both copies), ICP4 (one or both copies), ICP22, ICP27, ICP47, tk, UL41 and/or UL55 herpes simplex viral gene loci. In some embodiments, a recombinant herpes simplex virus genome comprises one or more polynucleotides of the present disclosure within one or both of the viral ICP4 gene loci (e.g., a recombinant virus comprising a polynucleotide encoding a SPINK polypeptide in one or both of the ICP4 loci). In some embodiments, a recombinant herpes simplex virus genome comprises one or more polynucleotides of the present disclosure within the viral ICP22 gene locus (e.g., a recombinant virus comprising a polynucleotide encoding a SPINK polypeptide in the ICP22 locus). In some embodiments, a recombinant herpes simplex virus genome comprises one or more polynucleotides of the present disclosure within the viral UL41 gene locus (e.g., a recombinant virus comprising a polynucleotide encoding a SPINK polypeptide in the UL41 locus). In some embodiments, a recombinant herpes simplex virus genome comprises one or more polynucleotides of the present disclosure within the viral ICP47 gene locus (e.g., a recombinant virus comprising a polynucleotide encoding a SPINK polypeptide in the ICP47 locus). In some embodiments, a recombinant herpes simplex virus genome comprises one or more polynucleotides of the present disclosure within one or both of the viral ICP4 gene loci, and one or more polynucleotides of the present disclosure within the viral ICP22 gene locus (e.g., a recombinant virus comprising a polynucleotide encoding a SPINK polypeptide in one or both of the ICP4 loci, and a polynucleotide encoding the same or a different SPINK polypeptide in the ICP22 locus). In some embodiments, a recombinant herpes simplex virus genome comprises one or more polynucleotides of the present disclosure within one or both of the viral ICP4 gene loci, and one or more polynucleotides of the present disclosure within the viral UL41 gene locus (e.g., a recombinant virus comprising a polynucleotide encoding a SPINK polypeptide in one or both of the ICP4 loci, and a polynucleotide encoding the same or a different SPINK polypeptide in the UL41 locus). In some embodiments, a recombinant herpes simplex virus genome comprises one or more polynucleotides of the present disclosure within the viral ICP22 gene locus, and one or more polynucleotides of the present disclosure within the viral UL41 gene locus (e.g., a recombinant virus comprising a polynucleotide encoding a SPINK polypeptide in the ICP22 locus, and a polynucleotide encoding the same or a different SPINK polypeptide in the UL41 locus). In some embodiments, a recombinant herpes simplex virus genome comprises one or more polynucleotides of the present disclosure within one or both of the viral ICP4 gene loci, one or more polynucleotides of the present disclosure within the viral ICP22 gene locus, and one or more polynucleotides of the present disclosure within the viral UL41 gene locus (e.g., a recombinant virus comprising a polynucleotide encoding a SPINK polypeptide in one or both of the ICP4 loci, a polynucleotide encoding the same or a different SPINK polypeptide in the ICP22 locus, and a polynucleotide encoding a SPINK polypeptide in the UL41 locus (which may be the same SPINK polypeptide encoded in the ICP4 and/or ICP22 loci or may be a different SPINK polypeptide than those encoded in the ICP4 and/or ICP22 loci).

In some embodiments, the recombinant herpes virus genome (e.g., a recombinant herpes simplex virus genome) has been engineered to decrease or eliminate expression of one or more herpes virus genes (e.g., one or more toxic herpes virus genes), such as one or both copies of the HSV ICP0 gene, one or both copies of the HSV ICP4 gene, the HSV ICP22 gene, the HSV UL41 gene, the HSV ICP27 gene, etc. In some embodiments, the recombinant herpes virus genome (e.g., recombinant herpes simplex virus genome) has been engineered to reduce cytotoxicity of the recombinant genome (e.g., when introduced into a target cell) as compared to a corresponding wild-type herpes virus genome (e.g., a wild-type herpes simplex virus genome). In some embodiments, the target cell is a human cell. In some embodiments, the target cell is a cell of the epidermis and/or dermis (e.g., a cell of the human epidermis and/or dermis). In some embodiments, the target cell is a keratinocyte or fibroblast (e.g., a human keratinocyte or human fibroblast). In some embodiments, cytotoxicity (e.g., in human keratinocytes and/or fibroblasts) of the recombinant genome (e.g., a recombinant herpes simplex virus genome) is reduced by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% as compared to a corresponding wild-type herpes virus genome (e.g., measuring the relative cytotoxicity of a recombinant ΔICP4 (one or both copies) herpes simplex virus genome vs. a wild-type herpes simplex virus genome in human keratinocytes or fibroblasts (primary cells or cell lines); measuring the relative cytotoxicity of a recombinant ΔICP4 (one or both copies)/ΔICP22 herpes simplex virus genome vs. a wild-type herpes simplex virus genome in human keratinocytes or fibroblasts (primary cells or cell lines); etc.). In some embodiments, cytotoxicity (e.g., in human keratinocytes and/or fibroblasts) of the recombinant genome (e.g., a recombinant herpes simplex virus genome) is reduced by at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 50-fold, at least about 75-fold, at least about 100-fold, at least about 250-fold, at least about 500-fold, at least about 750-fold, at least about 1000-fold, or more as compared to a corresponding wild-type herpes virus genome (e.g., measuring the relative cytotoxicity of a recombinant ΔICP4 (one or both copies) herpes simplex virus genome vs. a wild-type herpes simplex virus genome in human keratinocytes or fibroblasts (primary cells or cell lines); measuring the relative cytotoxicity of a recombinant ΔICP4 (one or both copies)/ΔICP22 herpes simplex virus genome vs. a wild-type herpes simplex virus genome in human keratinocytes or fibroblasts (primary cells or cell lines); etc.). Methods of measuring cytotoxicity are known to one of ordinary skill in the art, including, for example, through the use of vital dyes (formazan dyes), protease biomarkers, an MTT assay (or an assay using related tetrazolium salts such as XTT, MTS, water-soluble tetrazolium salts, etc.), measuring ATP content, etc.

In some embodiments, the recombinant herpes virus genome (e.g., a recombinant herpes simplex virus genome) has been engineered to reduce its impact on host cell proliferation after exposure of a target cell to the recombinant genome, as compared to a corresponding wild-type herpes virus genome (e.g., a wild-type herpes simplex virus genome). In some embodiments, the target cell is a human cell. In some embodiments, the target cell is a cell of the epidermis and/or dermis (e.g., a cell of the human epidermis and/or dermis). In some embodiments, the target cell is a keratinocyte or fibroblast (e.g., a human keratinocyte or human fibroblast). In some embodiments, host cell proliferation (e.g., of human keratinocytes and/or fibroblasts) after exposure to the recombinant genome is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% faster as compared to host cell proliferation after exposure to a corresponding wild-type herpes virus genome (e.g., measuring the relative cellular proliferation after exposure to a recombinant ΔICP4 (one or both copies) herpes simplex virus genome vs. cellular proliferation after exposure to a wild-type herpes simplex virus genome in human keratinocytes or fibroblasts (primary cells or cell lines); measuring the relative cellular proliferation after exposure to a recombinant ΔICP4 (one or both copies)/ΔICP22 herpes simplex virus genome vs. cellular proliferation after exposure to a wild-type herpes simplex virus genome in human keratinocytes or fibroblasts (primary cells or cell lines); etc.). In some embodiments, host cell proliferation (e.g., of human keratinocytes and/or fibroblasts) after exposure to the recombinant genome is at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 50-fold, at least about 75-fold, at least about 100-fold, at least about 250-fold, at least about 500-fold, at least about 750-fold, or at least about 1000-fold faster as compared to host cell proliferation after exposure to a corresponding wild-type herpes virus genome (e.g., measuring the relative cellular proliferation after exposure to a recombinant ΔICP4 (one or both copies) herpes simplex virus genome vs. cellular proliferation after exposure to a wild-type herpes simplex virus genome in human keratinocytes or fibroblasts (primary cells or cell lines); measuring the relative cellular proliferation after exposure to a recombinant ΔICP4 (one or both copies)/ΔICP22 herpes simplex virus genome vs. cellular proliferation after exposure to a wild-type herpes simplex virus genome in human keratinocytes or fibroblasts (primary cells or cell lines); etc.). Methods of measuring cellular proliferation are known to one of ordinary skill in the art, including, for example, through the use of a Ki67 cell proliferation assay, a BrdU cell proliferation assay, etc.

A vector (e.g., herpes viral vector) may include one or more polynucleotides of the present disclosure in a form suitable for expression of the polynucleotide in a host cell. Vectors may include one or more regulatory sequences operatively linked to the polynucleotide to be expressed (e.g., as described above).

In some embodiments, a recombinant nucleic acid (e.g., a recombinant herpes virus genome, such as a recombinant herpes simplex virus genome) of the present disclosure comprises one or more of the polynucleotides described herein inserted in any orientation in the recombinant nucleic acid. If the recombinant nucleic acid comprises two or more polynucleotides described herein (e.g., two or more, three or more, etc.), the polynucleotides may be inserted in the same orientation or opposite orientations to one another. Without wishing to be bound by theory, incorporating two polynucleotides (e.g., two transgenes) into a recombinant nucleic acid (e.g., a vector) in an antisense orientation may help to avoid read-through and ensure proper expression of each polynucleotide.

In some embodiments, the present disclosure relates to one or more heterologous polynucleotides (e.g., a bacterial artificial chromosome (BAC)) comprising any of the recombinant nucleic acids described herein.

IV. Viruses

Certain aspects of the present disclosure relate to viruses comprising any of the polynucleotides and/or recombinant nucleic acids described herein. In some embodiments, the virus is capable of infecting one or more target cells of a subject (e.g., a human). In some embodiments, the virus is suitable for delivering the polynucleotides and/or recombinant nucleic acids into one or more target cells of a subject (e.g., a human). In some embodiments, the present disclosure relates to one or more viral particles comprising any of the polynucleotides and/or recombinant nucleic acids described herein. In some embodiments, the one or more target cells are one or more human cells. In some embodiments, the one or more target cells are one or more cells with a SPINK deficiency (e.g., one or more cells comprising a loss-of-function mutation in, or a pathogenic variant of, a native SPINK gene, such as a SPINK5 gene). In some embodiments, the one or more target cells are one or more cells of the skin (e.g., one or more cells of the epidermis, dermis, and/or subcutis). In some embodiments, the one or more target cells are cells of the epidermis and/or dermis (e.g., cells of the human epidermis and/or dermis). In some embodiments, the one or more target cells are selected from keratinocytes, melanocytes, Langerhans cells, Merkel cells, mast cells, fibroblasts, and/or adipocytes. In some embodiments, the one or more target cells are keratinocytes. In some embodiments, the one or more target cells reside in the stratum corneum, stratum granulosum, stratum spinulosum, stratum basale, and/or basement membrane. In some embodiments, the one or more target cells are one or more epidermal cells. In some embodiments, the one or more target cells are one or more dermal cells.

Any suitable virus known in the art may be used, including, for example, adenovirus, adeno-associated virus, retrovirus, lentivirus, sendai virus, papillomavirus, herpes virus (e.g., a herpes simplex virus), vaccinia virus, and/or any hybrid or derivative viruses thereof. In some embodiments, the virus is attenuated. In some embodiments, the virus is replication defective. In some embodiments, the virus is replication competent. In some embodiments, the virus has been modified to alter its tissue tropism relative to the tissue tropism of a corresponding unmodified, wild-type virus. In some embodiments, the virus has reduced cytotoxicity as compared to a corresponding wild-type virus. Methods of producing a virus comprising recombinant nucleic acids are well known to one of ordinary skill in the art.

In some embodiments, the virus is a member of the Herpesviridae family of DNA viruses, including, for example, a herpes simplex virus, a varicella zoster virus, a human cytomegalovirus, a herpesvirus 6A, a herpesvirus 6B, a herpesvirus 7, and a Kaposi's sarcoma-associated herpesvirus, etc. In some embodiments, the herpes virus is attenuated. In some embodiments, the herpes virus is replication defective. In some embodiments, the herpes virus is replication competent. In some embodiments, the herpes virus has reduced cytotoxicity as compared to a corresponding wild-type herpes virus. In some embodiments, the herpes virus is not oncolytic.

In some embodiments, the herpes virus is a herpes simplex virus. Herpes simplex viruses comprising recombinant nucleic acids may be produced by a process disclosed, for example, in WO2015/009952 and/or WO2017/176336. In some embodiments, the herpes simplex virus is attenuated. In some embodiments, the herpes simplex virus is replication defective. In some embodiments, the herpes simplex virus is replication competent. In some embodiments, the herpes simplex virus is an HSV-1 virus, an HSV-2, or any derivatives thereof. In some embodiments, the herpes simplex virus is an HSV-1 virus. In some embodiments, the HSV-1 is attenuated. In some embodiments, the HSV-1 is replication defective. In some embodiments, the HSV-1 is replication competent. In some embodiments, the herpes simplex virus (e.g., the HSV-1) has reduced cytotoxicity as compared to a corresponding wild-type herpes simplex virus (e.g., a wild-type HSV-1). In some embodiments, the herpes simplex virus (e.g., the HSV-1) is not oncolytic.

In some embodiments, the herpes simplex virus has been modified to alter its tissue tropism relative to the tissue tropism of an unmodified, wild-type herpes simplex virus. In some embodiments, the herpes simplex virus comprises a modified envelope. In some embodiments, the modified envelope comprises one or more (e.g., one or more, two or more, three or more, four or more, etc.) mutant herpes simplex virus glycoproteins. Examples of herpes simplex virus glycoproteins may include, but are not limited to, the glycoproteins gB, gC, gD, gH, and gL. In some embodiments, the modified envelope alters the herpes simplex virus tissue tropism relative to a wild-type herpes simplex virus.

In some embodiments, the transduction efficiency (in vitro and/or in vivo) of a virus of the present disclosure (e.g., a herpes virus such as a herpes simplex virus) for one or more target cells (e.g., one or more human keratinocytes and/or fibroblasts) is at least about 25%. For example, the transduction efficiency of the virus for one or more target cells may be at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, at least about 99.5%, or more. In some embodiments, the virus is a herpes simplex virus and the transduction efficiency of the virus for one or more target cells (e.g., one or more human keratinocytes and/or fibroblasts) is about 85% to about 100%. In some embodiments, the virus is a herpes simplex virus and the transduction efficiency of the virus for one or more target cells (e.g., one or more human keratinocytes and/or fibroblasts) is at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100%. Methods of measuring viral transduction efficiency in vitro or in vivo are well known to one of ordinary skill in the art, including, for example, qPCR analysis, deep sequencing, western blotting, fluorometric analysis (such as fluorescent in situ hybridization (FISH), fluorescent reporter gene expression, immunofluorescence, FACS), etc.

V. Pharmaceutical Compositions and Formulations

Certain aspects of the present disclosure relate to pharmaceutical compositions and formulations comprising any of the recombinant nucleic acids (e.g., recombinant herpes virus genomes) and/or viruses (e.g., herpes viruses comprising the recombinant genomes) described herein (such as a herpes simplex virus comprising a recombinant herpes simplex virus genome), and a pharmaceutically acceptable excipient or carrier.

In some embodiments, the pharmaceutical composition or formulation comprises any one or more of the viruses (e.g., herpes viruses) described herein. In some embodiments, the pharmaceutical composition or formulation comprises from about $10^4$ to about $10^{12}$ plaque forming units (PFU)/mL of the virus. For example, the pharmaceutical composition or formulation may comprise from about $10^4$ to about $10^{12}$, about $10^5$ to about $10^{12}$, about $10^6$ to about $10^{12}$, about $10^7$ to about $10^{12}$, about $10^8$ to about $10^{12}$, about $10^9$ to about $10^{12}$, about $10^{10}$ to about $10^{12}$, about $10^{11}$ to about $10^{12}$, about $10^4$ to about $10^{11}$, about $10^5$ to about $10^{11}$, about $10^6$ to about $10^{11}$, about $10^7$ to about $10^{11}$, about $10^8$ to about $10^{11}$, about $10^9$ to about $10^{11}$, about $10^{10}$ to about $10^{11}$, about $10^4$ to about $10^{10}$, about $10^5$ to about $10^{10}$, about $10^6$ to about $10^{10}$, about $10^7$ to about $10^{10}$, about $10^8$ to about $10^{10}$, about $10^9$ to about $10^{10}$, about $10^4$ to about $10^9$, about $10^5$ to about $10^9$, about $10^6$ to about $10^9$, about $10^7$ to about $10^9$, about $10^8$ to about $10^9$, about $10^4$ to about $10^8$, about $10^5$ to about $10^8$, about $10^6$ to about 108, about $10^7$ to about $10^8$, about $10^4$ to about $10^7$, about $10^5$ to about $10^7$, about $10^6$ to about $10^7$, about $10^4$ to about $10^6$, about $10^5$ to about $10^6$, or about $10^4$ to about $10^5$ PFU/mL of the virus. In some embodiments, the pharmaceutical composition or formulation comprises about $10^4$, about $10^5$, about $10^6$, about $10^7$, about $10^8$, about $10^9$, about $10^{10}$, about $10^{11}$, or about $10^{12}$ PFU/mL of the virus.

Pharmaceutical compositions and formulations can be prepared by mixing the active ingredient(s) (such as a recombinant nucleic acid and/or a virus) having the desired degree of purity with one or more pharmaceutically acceptable carriers or excipients. Pharmaceutically acceptable carriers or excipients are generally nontoxic to recipients at the dosages and concentrations employed, and may include, but are not limited to: buffers (such as phosphate, citrate, acetate, and other organic acids); antioxidants (such as ascorbic acid and methionine); preservatives (such as octadecyldimethylbenzyl ammonium chloride, benzalkonium chloride, benzethonium chloride, phenol, butyl or benzyl alcohol, alkyl parabens, catechol, resorcinol, cyclohexanol, 3-pentanol, and m-cresol); amino acids (such as glycine, glutamine, asparagine, histidine, arginine, or lysine); low molecular weight (less than about 10 residues) polypeptides; proteins (such as serum albumin, gelatin, or immunoglobulins); polyols (such as glycerol, e.g., formulations including 1%, 2%, 3%, 4%, 5%, 6%, 7%, 8%, 9%, 10%, 11%, 12%, 13%, 14%, 15%, etc. glycerol); hydrophilic polymers (such as polyvinylpyrrolidone); monosaccharides, disaccharides, and other carbohydrates (including glucose, mannose, or dextrins); chelating agents (such as EDTA); sugars (such as sucrose, mannitol, trehalose, or sorbitol); salt-forming counter-ions (such as sodium); metal complexes (such as Zn-protein complexes); and/or non-ionic surfactants (such as polyethylene glycol (PEG)). A thorough discussion of pharmaceutically acceptable carriers is available in REMINGTON'S PHARMACEUTICAL SCIENCES (Mack Pub. Co., N.J. 1991).

In some embodiments, the pharmaceutical composition or formulation comprises one or more lipid (e.g., cationic lipid) carriers. In some embodiments, the pharmaceutical composition or formulation comprises one or more nanoparticle carriers. Nanoparticles are submicron (less than about 1000 nm) sized drug delivery vehicles that can carry encapsulated drugs (such as synthetic small molecules, proteins, peptides, cells, viruses, and nucleic acid-based biotherapeutics) for rapid or controlled release. A variety of molecules (e.g., proteins, peptides, recombinant nucleic acids, etc.) can be efficiently encapsulated in nanoparticles using processes well known in the art. In some embodiments, a molecule "encapsulated" in a nanoparticle may refer to a molecule (such as a virus) that is contained within the nanoparticle or attached to and/or associated with the surface of the nanoparticle, or any combination thereof. Nanoparticles for use in the compositions or formulations described herein may be any type of biocompatible nanoparticle known in the art, including, for example, nanoparticles comprising poly(lactic acid), poly(glycolic acid), PLGA, PLA, PGA, and any combinations thereof (see e.g., Vauthier et al. Adv Drug Del Rev. (2003) 55: 519-48; US2007/0148074; US2007/0092575; US2006/0246139; U.S. Pat. Nos. 5,753,234; 7,081,483; and WO2006/052285).

In some embodiments, the pharmaceutically acceptable carrier or excipient may be adapted for or suitable for any administration route known in the art, including, for example, intravenous, intramuscular, subcutaneous, cutaneous, oral, nasal, intratracheal, sublingual, buccal, topical, transdermal, intradermal, intraperitoneal, intraorbital, intravitreal, subretinal, transmucosal, intraarticular, by implantation, by inhalation, intrathecal, intraventricular, and/or intranasal administration. In some embodiments, the pharmaceutical composition or formulation is adapted for or suitable for any administration route known in the art, including, for example, intravenous, intramuscular, subcutaneous, cutaneous, oral, nasal, intratracheal, sublingual, buccal, topical, transdermal, intradermal, intraperitoneal, intraorbital, intravitreal, subretinal, transmucosal, intraarticular, by implantation, by inhalation, intrathecal, intraventricular, and/or intranasal administration. In some embodiments, the pharmaceutically acceptable carrier or excipient is adapted for or suitable for topical, transdermal, subcutaneous, intradermal, and/or transmucosal administration. In some embodiments, the pharmaceutical composition or formulation is adapted for or suitable for topical, transdermal, subcutaneous, intradermal, and/or transmucosal administration. In some embodiments, the pharmaceutically acceptable carrier or excipient is adapted for or suitable for topical, transdermal, and/or intradermal administration. In some embodiments, the pharmaceutical composition or formulation is adapted for or suitable for topical, transdermal, and/or intradermal administration. In some embodiments, the pharmaceutically acceptable carrier or excipient is adapted for or suitable for topical administration. In some embodiments, the pharmaceutical composition or formulation is adapted for or suitable for topical administration.

Examples of carriers or excipients adapted for or suitable for use in pharmaceutical compositions or formulations of the present disclosure may include, but are not limited to, ointments, oils, pastes, creams, aerosols, suspensions, emulsions, fatty ointments, gels (e.g., methylcellulose gels, such as carboxy methylcellulose, hydroxypropyl methylcellulose, etc.), powders, liquids, lotions, solutions, sprays, patches (e.g., transdermal patches or microneedle patches), adhesive strips, a microneedle or microneedle arrays, and inhalants. In some embodiments, the carrier or excipient (e.g., the pharmaceutically acceptable carrier or excipient) comprises one or more (e.g., one or more, two or more, three or more, four or more, five or more, etc.) of an ointment, oil, paste, cream, aerosol, suspension, emulsion, fatty ointment, gel, powder, liquid, lotion, solution, spray, patch, adhesive strip, and an inhalant. In some embodiments, the carrier comprises a patch (e.g. a patch that adheres to the skin), such as a transdermal patch or microneedle patch. In some embodiments, the carrier comprises a microneedle or microneedle array. Methods for making and using microneedle arrays suitable for composition delivery are generally known in the art (see e.g., Kim Y. et al. "Microneedles for drug and vaccine delivery". *Advanced Drug Delivery Reviews* 2012, 64 (14): 1547-68).

In some embodiments, the pharmaceutical composition or formulation further comprises one or more additional components. Examples of additional components may include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); wetting agents (e.g., sodium lauryl sulphate, etc.); salt solutions; alcohols; polyethylene glycols; gelatin; lactose; amylase; magnesium stearate; talc; silicic acid; viscous paraffin; methylcellulose; polyvinylpyrrolidone; sweetenings; flavorings; perfuming agents; colorants; moisturizers; sunscreens; antibacterial agents; agents able to stabilize polynucleotides or prevent their degradation, and the like. In some embodiments, the pharmaceutical composition or formulation comprises a methylcellulose gel, such as a carboxy methylcellulose gel, a hydroxypropyl methylcellulose gel, etc. (e.g., at about 0.5%, at about 1%, at about 1.5%, at about 2%, at about 2.5%, at about 3%, at about 3.5%, at about 4%, at about 4.5%, at about 5%, at about 5.5%, at about 6%, at about 6.5%, at about 7%, at about 7.5%, at about 8%, at about 8.5%, at about 9%, at about 9.5%, at about 10%, at about 10.5%, at about 11%, at about 11.5%, at about 12%, etc.). In some embodiments, the pharmaceutical composition or formulation comprises a phosphate buffer. In some embodiments, the pharmaceutical composition or formulation comprises glycerol (e.g., at about 1%, about 2%, about 3%, about 4%, about 5%, about 6%, about 7%, about 8%, about 9%, about 10%, about 11%, about 12%, about 13%, about 14%, about 15%, etc.). In some embodiments, the pharmaceutical composition or formulation comprises a methylcellulose gel (a carboxy methylcellulose gel, a hydroxypropyl methylcellulose gel, etc.), a phosphate buffer, and/or glycerol.

Compositions and formulations (e.g., pharmaceutical compositions and formulations) to be used for in vivo administration are generally sterile. Sterility may be readily accomplished, e.g., by filtration through sterile filtration membranes.

In some embodiments, any of the recombinant nucleic acids, viruses, and/or pharmaceutical compositions or formulations described herein may be used to deliver one or more polynucleotides encoding a SPINK polypeptide into one or more cells of a subject (e.g., one or more SPINK-deficient cells, one or more cells harboring a SPINK gene mutation, etc.). In some embodiments, any of the recombinant nucleic acids, viruses, and/or pharmaceutical compositions or formulations may be used in a therapy. In some embodiments, any of the recombinant nucleic acids, viruses, and/or pharmaceutical compositions or formulations described herein may be used in the treatment of a disease or condition that would benefit from the expression of a SPINK polypeptide (e.g., a disease associated with a SPINK deficiency and/or a disease associated with a SPINK gene mutation). In some embodiments, any of the recombinant nucleic acids, viruses, and/or pharmaceutical compositions or formulations described herein may be used for providing prophylactic, palliative, or therapeutic relief to one or more signs or symptoms of Netherton Syndrome (e.g., via delivery of a SPINK5 polypeptide), atopic dermatitis (e.g., via delivery of a SPINK5 polypeptide), hereditary pancreatitis (PCTT) (e.g., via delivery of a SPINK1 polypeptide), tropical calcific pancreatitis (e.g., via delivery of a SPINK1 polypeptide), and/or spermatogenic failure 29 (SPGF29) (e.g., via delivery of a SPINK2 polypeptide). In some embodiments, any of the recombinant nucleic acids, viruses, and/or pharmaceutical compositions or formulations described herein may be used to treat Netherton Syndrome (e.g., via delivery of a human SPINK5 polypeptide). In some embodiments, any of the recombinant nucleic acids, viruses, and/or pharmaceutical compositions or formulations described herein may be used to treat atopic dermatitis (e.g., via delivery of a human SPINK5 polypeptide).

In some embodiments, any of the recombinant nucleic acids, viruses, and/or pharmaceutical compositions or formulations described herein may be used in the preparation or manufacture of a medicament. In some embodiments, any of the recombinant nucleic acids, viruses, and/or pharmaceutical compositions or formulations described herein may be used in the preparation or manufacture of a medicament useful for delivering one or more polynucleotides encoding a SPINK polypeptide into one or more cells of a subject (e.g., one or more SPINK-deficient cells, one or more cells harboring a SPINK gene mutation, etc.). In some embodiments, any of the recombinant nucleic acids, viruses, and/or pharmaceutical compositions or formulations described herein may be used in the preparation or manufacture of a medicament useful for the treatment of a disease or condition that would benefit from the expression of a SPINK polypeptide (e.g., a disease associated with a SPINK deficiency and/or a disease associated with a SPINK gene mutation). In some embodiments, any of the recombinant nucleic acids, viruses, and/or pharmaceutical compositions or formulations described herein may be used in the preparation or manufacture of a medicament useful for the treatment of Netherton Syndrome (e.g., via delivery of a SPINK5 polypeptide), atopic dermatitis (e.g., via delivery of a SPINK5 polypeptide), hereditary pancreatitis (PCTT) (e.g., via delivery of a SPINK1 polypeptide), tropical calcific pancreatitis (e.g., via delivery of a SPINK1 polypeptide), and/or spermatogenic failure 29 (SPGF29) (e.g., via delivery of a SPINK2 polypeptide). In some embodiments, any of the recombinant nucleic acids, viruses, and/or pharmaceutical compositions or formulations described herein may be used in the preparation or manufacture of a medicament useful for the treatment of Netherton Syndrome (e.g., via delivery of a human SPINK5 polypeptide). In some embodiments, any of the recombinant nucleic acids, viruses, and/or pharmaceutical compositions or formulations described herein may be used in the preparation or manufacture of a medicament useful for the treatment of atopic dermatitis (e.g., via delivery of a human SPINK5 polypeptide).

VI. Methods

Certain aspects of the present disclosure relate to enhancing, increasing, augmenting, and/or supplementing the levels of a SPINK polypeptide in one or more cells of a subject comprising administering to the subject an effective amount of any of the recombinant nucleic acids, viruses, medicaments, and/or pharmaceutical compositions or formulations described herein. In some embodiments, the SPINK polypeptide is a human SPINK polypeptide. In some embodiments, the SPINK polypeptide is a SPINK5 polypeptide. In some embodiments, the SPINK5 polypeptide is a human SPINK5 polypeptide. In some embodiments, the subject is a human. In some embodiments, the subject's genome comprises a mutation (e.g., a loss-of-function mutation, a pathogenic variant) in an endogenous SPINK gene (such as an endogenous SPINK5 gene). In some embodiments, the subject suffers from Netherton Syndrome. In some embodiments, the subject suffers from atopic dermatitis.

In some embodiments, administration of the recombinant nucleic acid, virus, medicament, and/or pharmaceutical composition or formulation to the subject increases SPINK (e.g., SPINK5) levels (transcript or protein levels) by at least about 2-fold in one or more contacted or treated cells of the subject, as compared to the endogenous levels of the SPINK in one or more corresponding untreated cells of the subject. For example, administration of the recombinant nucleic acid, virus, medicament, and/or pharmaceutical composition or formulation may increase SPINK (e.g., SPINK5) levels (transcript or protein levels) by at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 50-fold, at least about 75-fold, at least about 100-fold, at least about 250-fold, at least about 500-fold, at least about 750-fold, at least about 1000-fold, or more in one or more contacted or treated cells of the subject, as compared to the endogenous levels of the SPINK in one or more corresponding untreated cells of the subject. In some embodiments, the one or more contacted or treated cells are one or more cells of the epidermis and/or dermis (e.g., a keratinocyte). Methods of measuring transcript or protein levels from a sample are well known to one of ordinary skill in the art, including, for example, by qPCR, western blot, mass spectrometry, etc.

In some embodiments, administering to an individual an effective amount of any of the recombinant nucleic acids, viruses, medicaments, and/or pharmaceutical compositions or formulation described herein enhances, increases, augments, and/or supplements the integrity and/or protective barrier function of the skin of the subject. In some embodiments, administering to an individual an effective amount of any of the recombinant nucleic acids, viruses, medicaments, and/or pharmaceutical compositions or formulations described herein decreases, augments, and/or inhibits one or more of Kallikrein-5 (KLK5), Kallikrein-7 (KLK7), Kallikrein-14 (KLK14), Caspase-14 (CASP14) and trypsin in the subject (e.g., decreases, augments, and/or inhibits one or more activities (e.g., proteolytic activities) of KLK5, KLK7, KLK14, CASP14, and/or trypsin).

Other aspects of the present disclosure relate to enhancing, increasing, augmenting, and/or supplementing anti-inflammatory and/or anti-microbial protection of mucous epithelia in a subject in need thereof comprising administering to the subject an effective amount of any of the recombinant nucleic acids, viruses, medicaments, and/or pharmaceutical compositions or formulations described herein. In some embodiments, administration of the recombinant nucleic acid, virus, medicament, and/or pharmaceutical composition reduces the susceptibility to skin infections of the subject.

Other aspects of the present disclosure relate to repressing or inhibiting desquamation in a subject in need thereof comprising administering to the subject an effective amount of any of the recombinant nucleic acids, viruses, medicaments, and/or pharmaceutical compositions or formulations described herein.

Other aspects of the present disclosure relate to reducing or treating a skin barrier defect in a subject in need thereof comprising administering to the subject an effective amount of any of the recombinant nucleic acids, viruses, medicaments, and/or pharmaceutical compositions or formulations described herein. In some embodiments, the skin barrier defect is transepidermal water loss (TEWL), also called transepithelial water loss. In some embodiments, the methods of the present disclosure reduce transepidermal water loss in a subject in need thereof. Methods of measuring skin barrier function, including TEWL, are well known to one of ordinary skill in the art, including, for example, by any of the methods described by Antonov et al. (Curr Probl Dermatol. 2016; 49:61-70).

Other aspects of the present disclosure relate to providing prophylactic, palliative, or therapeutic relief of one or more signs or symptoms of Netherton Syndrome in a subject in need thereof comprising administering to the subject an effective amount of any of the recombinant nucleic acids, viruses, medicaments, and/or pharmaceutical compositions or formulations described herein. In some embodiments, the subject's genome comprises a mutation (e.g., a loss-of-function mutation, a pathogenic variant) in an endogenous SPINK5 gene. In some embodiments, the recombinant nucleic acid, virus, medicament, and/or pharmaceutical composition or formulation comprises one or more polynucleotides encoding a human SPINK5 polypeptide.

Signs and/or symptoms of Netherton Syndrome may include, but are not limited to defective keratinization, a defective skin barrier, chronic skin inflammation, universal pruritus (itch), severe dehydration, stunted growth, trichorrhexis invaginata and/or trichorrhexis nodosa (hair shaft defect, also known as bamboo hair), leaking fluid from the skin, development of ring-like lesions on the skin, eczema, increased susceptibility to infection (particularly of the skin, including recurrent skin infections with *Staphylococcus*), increased susceptibility to allergy, development of scaly/reddish skin (similar to atopic dermatitis), development of ichthyosis linearis circumflexa and/or ichthyosiform erythroderma, altered immunoglobulin levels (typically high IgE and low to normal IgG immunoglobulins), immature natural killer cells (having reduced lytic function), and difficulty regulating body temperature.

Other aspects of the present disclosure relate to providing prophylactic, palliative, or therapeutic relief of one or more signs or symptoms of atopic dermatitis in a subject in need thereof comprising administering to the subject an effective amount of any of the recombinant nucleic acids, viruses, medicaments, and/or pharmaceutical compositions or formulations described herein. In some embodiments, the subject's genome comprises a mutation (e.g., a loss-of-function mutation, a pathogenic variant) in an endogenous SPINK5 gene. In some embodiments, the recombinant nucleic acid, virus, medicament, and/or pharmaceutical composition or formulation comprises one or more polynucleotides encoding a human SPINK5 polypeptide.

Signs and symptoms of atopic dermatitis may include, without limitation: dry skin; itching, which may be severe, especially at night; red to brownish-gray patches, especially on the hands, feet, ankles, wrists, neck, upper chest, eyelids, inside the bend of the elbows and knees, and in infants, the face and scalp; small, raised bumps on the skin which may be weeping; skin infections; eyelid dermatitis; cataracts; increased IgE levels; thickened, cracked, or scaly skin; and raw, sensitive, swollen skin from scratching.

The recombinant nucleic acids, viruses, medicaments, and/or pharmaceutical compositions or formulations described herein may be administered by any suitable method or route known in the art, including, without limitation, orally, sublingually, buccally, topically, rectally, via inhalation, transdermally, subcutaneously, intradermally, intravenously, intraarterially, intramuscularly, intracardially, intraosseously, intraperitoneally, transmucosally, vaginally, intravitreally, intraorbitally, subretinally, intraarticularly, peri-articularly, locally, epicutaneously, or any combinations thereof. The present disclosure thus encompasses methods of delivering any of the recombinant nucleic acids, viruses, medicaments, and/or pharmaceutical compositions or formulations described herein to an individual (e.g., an individual having, or at risk of developing, Netherton Syndrome and/or atopic dermatitis).

In some embodiments, the recombinant nucleic acids, viruses, medicaments, and/or pharmaceutical compositions or formulations described herein are administered topically, transdermally, subcutaneously, intradermally, or transmucosally to the subject. In some embodiments, the recombinant nucleic acids, viruses, medicaments, and/or pharmaceutical compositions or formulations are administered topically, transdermally, or intradermally to the subject. In some embodiments, the recombinant nucleic acids, viruses, medicaments, and/or pharmaceutical compositions or formulations are administered topically or intradermally to the subject. In some embodiments, the recombinant nucleic acids, viruses, medicaments, and/or pharmaceutical compositions or formulations are administered topically to the subject.

In some embodiments, the recombinant nucleic acids, viruses, medicaments, and/or pharmaceutical compositions or formulations are administered once to the subject. In some embodiments, the recombinant nucleic acids, viruses, medicaments, and/or pharmaceutical compositions or formulations are administered at least twice (e.g., at least 2 times, at least 3 times, at least 4 times, at least 5 times, at least 10 times, etc.) to the subject. In some embodiments, at least about 1 hour (e.g., at least about 1 hour, at least about 6 hours, at least about 12 hours, at least about 18 hours, at least about 1 day, at least about 2 days, at least about 3 days, at least about 4 days, at least about 5 days, at least about 6 days, at least about 7 days, at least about 15 days, at least about 20 days, at least about 30 days, at least about 40 days, at least about 50 days, at least about 60 days, at least about 70 days, at least about 80 days, at least about 90 days, at least about 100 days, at least about 120 days, etc.) pass between administrations (e.g., between the first and second administrations, between the second and third administrations, etc.). In some embodiments, the recombinant nucleic acids, viruses, medicaments, and/or pharmaceutical compositions or formulations are administered one, two, three, four, five or more times per day to the subject. In some embodiments, the recombinant nucleic acids, viruses, medicaments, and/or pharmaceutical compositions or formulations are administered to one or more affected (e.g., one or more regions of the skin displaying one or more signs or symptoms of Netherton Syndrome and/or atopic dermatitis) and/or unaffected areas of the subject.

In some embodiments, one or more portions of the skin of the subject is abraded or made more permeable prior to treatment. Any suitable method of abrading the skin or increasing skin permeability known in the art may be used, including, for example, use of a dermal roller, repeated use of adhesive strips to remove layers of skin cells (tape stripping), scraping with a scalpel or blade, use of sandpaper, use of chemical permeation enhancers or electrical energy, use of sonic or ultrasonic energy, use of light (e.g., laser) energy, use of micron-sized needles or blades with a length suitable to pierce but not completely pass through the epidermis, etc.

VII. Host Cells

Certain aspects of the present disclosure relate to one or more host cells comprising any of the recombinant nucleic acids described herein. Any suitable host cell (prokaryotic or eukaryotic) known in the art may be used, including, for example: prokaryotic cells including eubacteria, such as Gram-negative or Gram-positive organisms, for example Enterobacteriaceae such as *Escherichia* (e.g., *E. coli*), Enterobacter, Erminia, *Klebsiella, Proteus, Salmonella* (e.g.,

*S. typhimurium*), *Serratia* (e.g., *S. marcescans*), and *Shigella*, as well as *Bacilli* such as *B. subtilis* and *B. ilcheniformis*; fungal cells (e.g., *S. cerevisiae*); insect cells (e.g., S2 cells, etc.); and mammalian cells, including monkey kidney CV1 line transformed by SV40 (COS-7, ATCC CRL 1651), human embryonic kidney line (293 or 293 cells subcloned for growth in suspension culture), baby hamster kidney cells (BHK, ATCC CCL 10), mouse Sertoli cells (TM4), monkey kidney cells (CV1 ATCC CCL 70), African green monkey kidney cells (VERO-76, ATCC CRL-1587), human cervical carcinoma cells (HELA, ATCC CCL 2), canine kidney cells (MDCK, ATCC CCL 34), buffalo rat liver cells (BRL 3A, ATCC CRL 1442), human lung cells (W138, ATCC CCL 75), human liver cells (Hep G2, HB 8065), mouse mammary tumor (MMT 060562, ATCC CCL51), TRI cells, MRC 5 cells, FS4 cells, human hepatoma line (Hep G2), Chinese hamster ovary (CHO) cells, including DHFR" CHO cells, and myeloma cell lines such as NS0 and Sp2/0. In some embodiments, the host cell is a human or non-human primate cell. In some embodiments, the host cells are cells from a cell line. Examples of suitable host cells or cell lines may include, but are not limited to, 293, HeLa, SH-Sy5y, Hep G2, CACO-2, A549, L929, 3T3, K562, CHO-K1, MDCK, HUVEC, Vero, N20, COS-7, PSN1, VCaP, CHO cells, and the like.

In some embodiments, the recombinant nucleic acid is a herpes simplex viral vector. In some embodiments, the recombinant nucleic acid is a herpes simplex virus amplicon. In some embodiments, the recombinant nucleic acid is an HSV-1 amplicon or HSV-1 hybrid amplicon. In some embodiments, a host cell comprising a helper virus is contacted with an HSV-1 amplicon or HSV-1 hybrid amplicon described herein, resulting in the production of a virus comprising one or more recombinant nucleic acids described herein. In some embodiments, the virus is collected from the supernatant of the contacted host cell. Methods of generating virus by contacting host cells comprising a helper virus with an HSV-1 amplicon or HSV-1 hybrid amplicon are known in the art.

In some embodiments, the host cell is a complementing host cell. In some embodiments, the complementing host cell expresses one or more genes that are inactivated in any of the viral vectors described herein. In some embodiments, the complementing host cell is contacted with a recombinant herpes virus genome (e.g., a recombinant herpes simplex virus genome) described herein. In some embodiments, contacting a complementing host cell with a recombinant herpes virus genome results in the production of a herpes virus comprising one or more recombinant nucleic acids described herein. In some embodiments, the virus is collected from the supernatant of the contacted host cell. Methods of generating virus by contacting complementing host cells with a recombinant herpes simplex virus are generally described in WO2015/009952 and/or WO2017/176336.

VIII. Articles of Manufacture or Kits

Certain aspects of the present disclosure relate to an article of manufacture or a kit comprising any of the recombinant nucleic acids, viruses, medicaments, and/or pharmaceutical compositions or formulations described herein. In some embodiments, the article of manufacture or kit comprises a package insert comprising instructions for administering the recombinant nucleic acid, virus, medicament, and/or pharmaceutical composition or formulation to treat a SPINK deficiency (e.g., in a subject harboring a SPINK gene mutation) and/or to provide prophylactic, palliative, or therapeutic relief of one or more signs or symptoms of a disease associated with a SPINK deficiency (such as Netherton Syndrome and/or atopic dermatitis).

Suitable containers for the recombinant nucleic acids, viruses, medicaments, and/or pharmaceutical compositions or formulations may include, for example, bottles, vials, bags, tubes, and syringes. The container may be formed from a variety of materials such as glass, plastic (such as polyvinyl chloride or polyolefin), or metal alloy (such as stainless steel or hastelloy). In some embodiments, the container comprises a label on, or associated with the container, wherein the label indicates directions for use. The article of manufacture or kit may further include other materials desirable from a commercial and user standpoint, including other buffers, diluents, filters, needles, syringes, package inserts, and the like.

IX. Enumerated Embodiments

Embodiment 1: a recombinant herpes virus genome comprising one or more polynucleotides encoding a Serine Protease Inhibitor Kazal-type (SPINK) polypeptide.

Embodiment 2: the recombinant herpes virus genome of embodiment 1, wherein the recombinant herpes virus genome is replication competent.

Embodiment 3: the recombinant herpes virus genome of embodiment 1, wherein the recombinant herpes virus genome is replication defective.

Embodiment 4: the recombinant herpes virus genome of any one of embodiments 1-3, wherein the recombinant herpes virus genome comprises the one or more polynucleotides encoding the SPINK polypeptide within one or more viral gene loci.

Embodiment 5: the recombinant herpes virus genome of any one of embodiments 1-4, wherein the recombinant herpes virus genome is selected from a recombinant herpes simplex virus genome, a recombinant varicella zoster virus genome, a recombinant human cytomegalovirus genome, a recombinant herpesvirus 6A genome, a recombinant herpesvirus 6B genome, a recombinant herpesvirus 7 genome, a recombinant Kaposi's sarcoma-associated herpesvirus genome, and any derivatives thereof.

Embodiment 6: the recombinant herpes virus genome of any one of embodiments 1-5, wherein the recombinant herpes virus genome is a recombinant herpes simplex virus genome.

Embodiment 7: the recombinant herpes virus genome of embodiment 5 or embodiment 6, wherein the recombinant herpes simplex virus genome is a recombinant type 1 herpes simplex virus (HSV-1) genome, a recombinant type 2 herpes simplex virus (HSV-2) genome, or any derivatives thereof.

Embodiment 8: the recombinant herpes virus genome of any one of embodiments 1-7, wherein the SPINK polypeptide is a human SPINK polypeptide.

Embodiment 9: the recombinant herpes virus genome of any one of embodiments 1-7, wherein the SPINK polypeptide is a Serine Protease Inhibitor Kazal-type 5 (SPINK5) polypeptide.

Embodiment 10: the recombinant herpes virus genome of any one of embodiments 1-9, wherein the SPINK polypeptide is a human SPINK5 polypeptide.

Embodiment 11: the recombinant herpes virus genome of embodiment 9 or embodiment 10, wherein the SPINK5 polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 7-25.

Embodiment 12: the recombinant herpes virus genome of any one of embodiments 9-11, wherein the SPINK5 polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 7-9.

Embodiment 13: the recombinant herpes virus genome of any one of embodiments 9-12, wherein the SPINK5 polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence of SEQ ID NO: 7.

Embodiment 14: the recombinant herpes virus genome of any one of embodiments 5-13, wherein the recombinant herpes simplex virus genome comprises an inactivating mutation.

Embodiment 15: the recombinant herpes virus genome of embodiment 14, wherein the inactivating mutation is in a herpes simplex virus gene.

Embodiment 16: the recombinant herpes virus genome of embodiment 15, wherein the inactivating mutation is a deletion of the coding sequence of the herpes simplex virus gene.

Embodiment 17: the recombinant herpes virus genome of embodiment 15 or embodiment 16, wherein the herpes simplex virus gene is selected from Infected Cell Protein (ICP) 0, ICP4, ICP22, ICP27, ICP47, thymidine kinase (tk), Long Unique Region (UL) 41, and UL55.

Embodiment 18: the recombinant herpes virus genome of embodiment 17, wherein the recombinant herpes simplex virus genome comprises an inactivating mutation in one or both copies of the ICP4 gene.

Embodiment 19: the recombinant herpes virus genome of embodiment 17 or embodiment 18, wherein the recombinant herpes simplex virus genome comprises an inactivating mutation in the ICP22 gene.

Embodiment 20: the recombinant herpes virus genome of any one of embodiments 17-19, wherein the recombinant herpes simplex virus genome comprises an inactivating mutation in the UL41 gene.

Embodiment 21: the recombinant herpes virus genome of any one of embodiments 17-20, wherein the recombinant herpes simplex virus genome comprises an inactivating mutation in one or both copies of the ICP0 gene.

Embodiment 22: the recombinant herpes virus genome of any one of embodiments 17-21, wherein the recombinant herpes simplex virus genome comprises an inactivating mutation in the ICP27 gene.

Embodiment 23: the recombinant herpes virus genome of any one of embodiments 5-22, wherein the recombinant herpes simplex virus genome comprises the one or more polynucleotides encoding the SPINK polypeptide within one or both of the ICP4 viral gene loci.

Embodiment 24: the recombinant herpes virus genome of any one or embodiments 5-23, wherein the recombinant herpes simplex virus genome comprises the one or more polynucleotides encoding the SPINK polypeptide within the ICP22 viral gene locus.

Embodiment 25: the recombinant herpes virus genome of any one of embodiments 5-24, wherein the recombinant herpes simplex virus genome comprises the one or more polynucleotides encoding the SPINK polypeptide within the UL41 viral gene locus.

Embodiment 26: the recombinant herpes virus genome of any one of embodiments 1-25, wherein the recombinant herpes virus genome has reduced cytotoxicity when introduced into a target cell as compared to a corresponding wild-type herpes virus genome.

Embodiment 27: the recombinant herpes virus genome of embodiment 26, wherein the target cell is a human cell.

Embodiment 28: the recombinant herpes virus genome of embodiment 26 or embodiment 27, wherein the target cell is a cell of the epidermis and/or dermis.

Embodiment 29: the recombinant herpes virus genome of any one of embodiments 26-28, wherein the target cell is a keratinocyte or fibroblast.

Embodiment 30: a herpes virus comprising the recombinant herpes virus genome of any one of embodiments 1-29.

Embodiment 31: the herpes virus of embodiment 30, wherein the herpes virus is replication competent.

Embodiment 32: the herpes virus of embodiment 30, wherein the herpes virus is replication defective.

Embodiment 33: the herpes virus of any one of embodiments 30-32, wherein the herpes virus has reduced cytotoxicity as compared to a corresponding wild-type herpes virus.

Embodiment 34: the herpes virus of any one of embodiments 30-33, wherein the herpes virus is selected from a herpes simplex virus, a varicella zoster virus, a human cytomegalovirus, a herpesvirus 6A, a herpesvirus 6B, a herpesvirus 7, a Kaposi's sarcoma-associated herpesvirus, and any derivatives thereof.

Embodiment 35: the herpes virus of any one of embodiments 30-34, wherein the herpes virus is a herpes simplex virus.

Embodiment 36: the herpes virus of embodiment 34 or embodiment 35, wherein the herpes simplex virus is an HSV-1 virus, an HSV-2 virus, or any derivatives thereof.

Embodiment 37: a pharmaceutical composition comprising the recombinant herpes virus genome of any one of embodiments 1-29 and/or the herpes virus of any one of embodiments 30-36 and a pharmaceutically acceptable excipient.

Embodiment 38: the pharmaceutical composition of embodiment 37, wherein the pharmaceutical composition is suitable for topical, transdermal, subcutaneous, intradermal, oral, sublingual, buccal, rectal, vaginal, inhaled, intravenous, intraarterial, intramuscular, intracardiac, intraosseous, intraperitoneal, transmucosal, intravitreal, subretinal, intraarticular, peri-articular, local, or epicutaneous administration.

Embodiment 39: the pharmaceutical composition of embodiment 37 or embodiment 38, wherein the pharmaceutical composition is suitable for topical, transdermal, subcutaneous, intradermal, or transmucosal administration.

Embodiment 40: the pharmaceutical composition of any one of embodiments 37-39, wherein the pharmaceutical composition is suitable for topical administration.

Embodiment 41: the pharmaceutical composition of any one of embodiments 37-40, wherein the pharmaceutical composition comprises a hydroxypropyl methylcellulose gel.

Embodiment 42: the pharmaceutical composition of any one of embodiments 37-41, wherein the pharmaceutical composition comprises a phosphate buffer.

Embodiment 43: the pharmaceutical composition of any one of embodiments 37-42, wherein the pharmaceutical composition comprises glycerol.

Embodiment 44: the pharmaceutical composition of any one of embodiments 37-43, wherein the pharmaceutical composition comprises a lipid carrier.

Embodiment 45: the pharmaceutical composition of any one of embodiments 37-44, wherein the pharmaceutical composition comprises a nanoparticle carrier.

Embodiment 46: a method of enhancing, increasing, augmenting, and/or supplementing the levels of a SPINK polypeptide in one or more cells of a subject, the method comprising administering to the subject an effective amount of the herpes virus of any one of embodiments 30-36 or the pharmaceutical composition of any one of embodiments 37-45.

Embodiment 47: the method of embodiment 46, wherein the SPINK polypeptide is a SPINK5 polypeptide.

Embodiment 48: a method of enhancing, increasing, augmenting, and/or supplementing anti-inflammatory and/or anti-microbial protection of mucous epithelia in a subject in need thereof, the method comprising administering to the subject an effective amount of the herpes virus of any one of embodiments 30-36 or the pharmaceutical composition of any one of embodiments 37-45.

Embodiment 49: a method of repressing desquamation in a subject in need thereof, the method comprising administering to the subject an effective amount of the herpes virus of any one of embodiments 30-36 or the pharmaceutical composition of any one of embodiments 37-45.

Embodiment 50: a method of reducing or treating a skin barrier defect in a subject in need thereof, the method comprising administering to the subject an effective amount of the herpes virus of any one of embodiments 30-36 or the pharmaceutical composition of any one of embodiments 37-45.

Embodiment 51: the method of embodiment 50, wherein the skin barrier defect is transepithelial water loss (TEWL).

Embodiment 52: a method of providing prophylactic, palliative, or therapeutic relief of one or more signs or symptoms of Netherton Syndrome (NS) in a subject in need thereof, the method comprising administering to the subject an effective amount of the herpes virus of any one of embodiments 30-36 or the pharmaceutical composition of any one of embodiments 37-45.

Embodiment 53: the method of embodiment 52, wherein the one or more signs or symptoms of NS are selected from the group consisting of defective keratinization, a defective skin barrier, recurrent skin infections, congenital ichthyosiform erythroderma, ichthyosis linearis circumflexa, trichorrhexis invaginata, chronic skin inflammation, and any combinations thereof.

Embodiment 54: the method of any one of embodiments 46-53, wherein the subject is a human.

Embodiment 55: the method of any one of embodiments 46-54, wherein the subject's genome comprises a loss-of-function mutation in a SPINK5 gene.

Embodiment 56: the method of any one of embodiments 46-55, wherein the herpes virus or pharmaceutical composition is administered topically, transdermally, subcutaneously, epicutaneously, intradermally, orally, sublingually, buccally, rectally, vaginally, intravenously, intraarterially, intramuscularly, intraosseously, intracardially, intraperitoneally, transmucosally, intravitreally, subretinally, intraarticularly, periarticularly, locally, or via inhalation to the subject.

Embodiment 57: the method of any one of embodiments 46-56, wherein the herpes virus or pharmaceutical composition is administered topically, transdermally, subcutaneously, intradermally, or transmucosally to the subject.

Embodiment 58: the method of any one of embodiments 46-57, wherein the herpes virus or pharmaceutical composition is administered topically to the subject.

Embodiment 59: the method of any one of embodiments 46-58, wherein the skin of the subject is abraded prior to administration.

The specification is considered to be sufficient to enable one skilled in the art to practice the present disclosure. Various modifications of the present disclosure in addition to those shown and described herein will become apparent to those skilled in the art from the foregoing description and fall within the scope of the appended claims.

EXAMPLES

The present disclosure will be more fully understood by reference to the following examples. They should not, however, be construed as limiting the scope of the present disclosure. It is understood that the examples and embodiments described herein are for illustrative purposes only and that various modifications or changes in light thereof will be suggested to persons skilled in the art and are to be included within the spirit and purview of this application and scope of the appended claims.

Figure 1D:
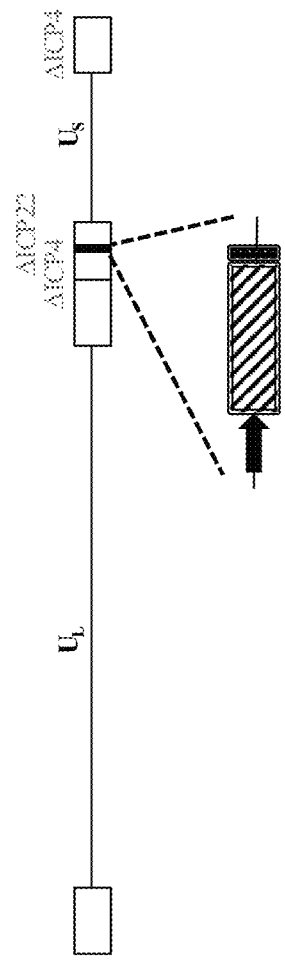
Figure 1E:
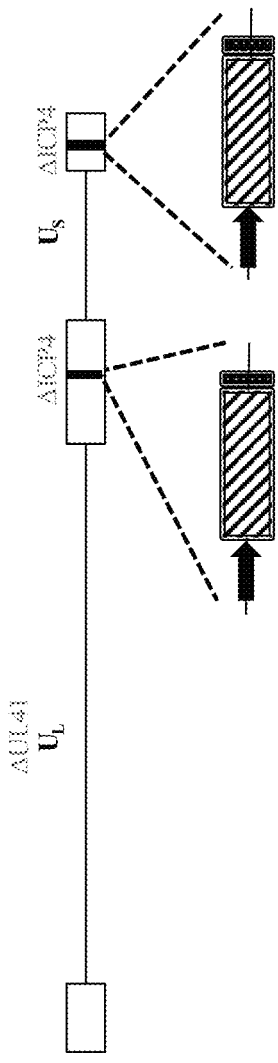
Figure 1F:
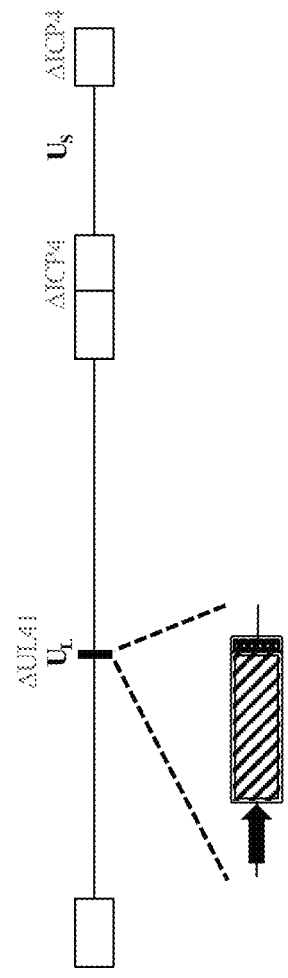
Figure 1G:
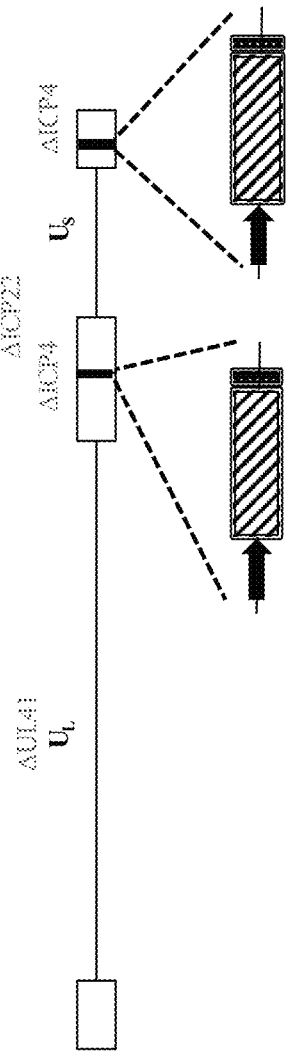
Figure 1H:
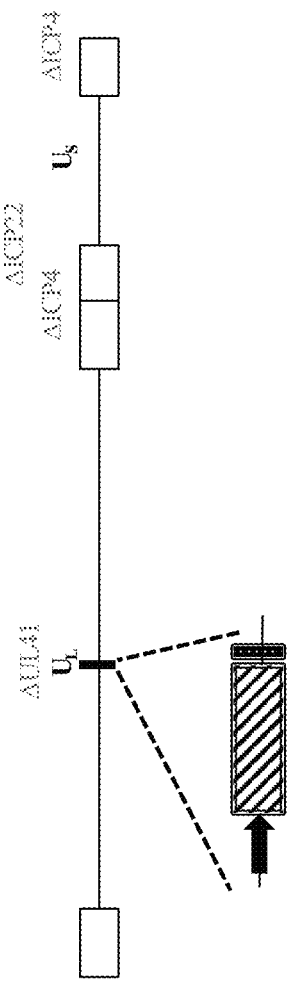
Figure 1I:
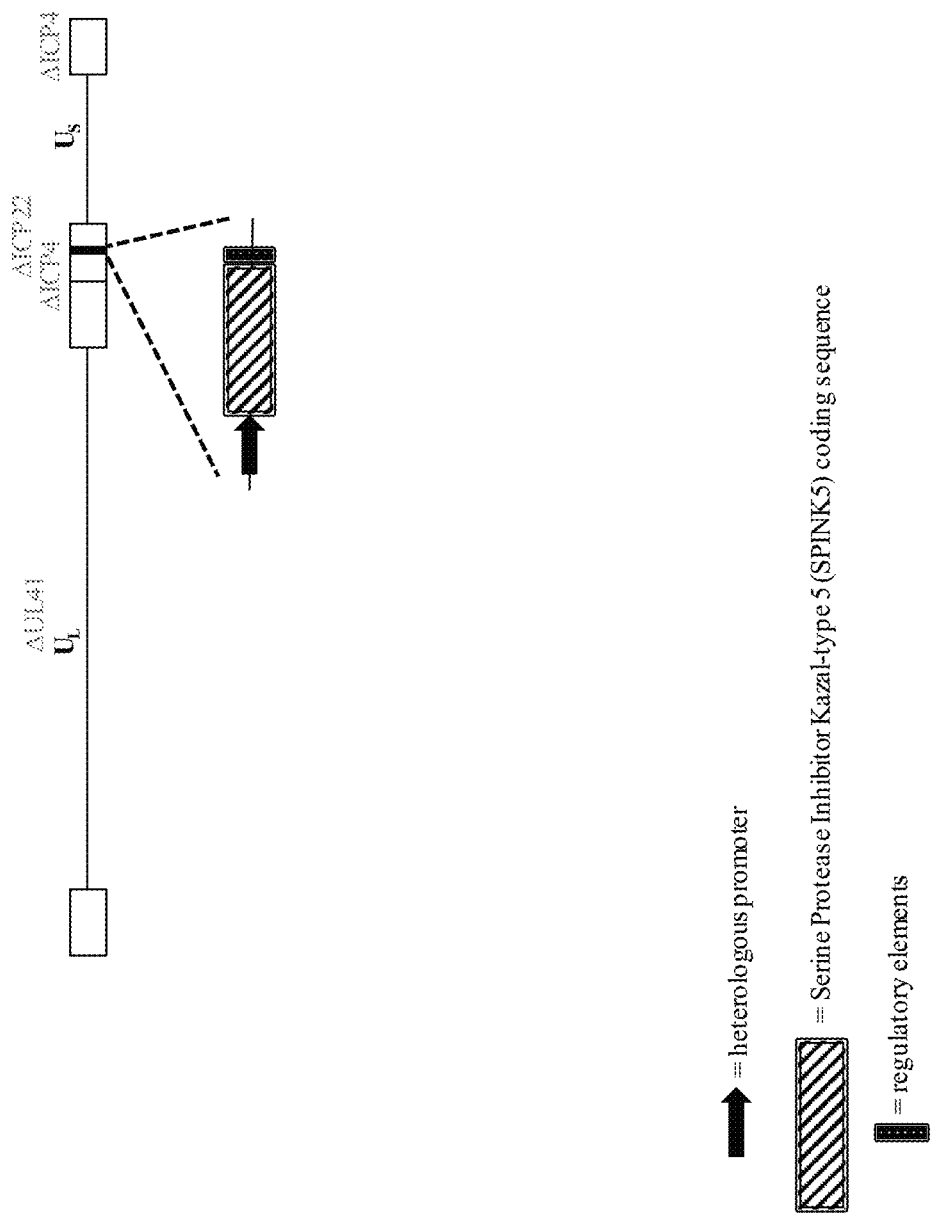

Example 1: Modified Herpes Simplex Virus Vectors Encoding a Human SPINK5 Protein To make modified, recombinant herpes simplex virus genome vectors capable of expressing SPINK5 polypeptides in a target mammalian cell (such as a human keratinocyte or fibroblast), a herpes simplex virus genome (FIG. 1A) is first modified to inactivate one or more herpes simplex virus genes. Such modifications may decrease the toxicity of the genome in mammalian cells. Next, variants of these modified/attenuated recombinant viral constructs are generated such that they carry one or more polynucleotides encoding the desired SPINK5 polypeptide. These variants include: 1) a recombinant ΔICP4-modified HSV-1 genome comprising expression cassettes containing the coding sequence (e.g., SEQ ID NO: 2) of a human SPINK5 polypeptide (e.g., SEQ ID NO: 7) under the control of a heterologous promoter integrated at each ICP4 locus (FIG. 1B); 2) a recombinant ΔICP4/ΔICP22-modified HSV-1 genome comprising expression cassettes containing the coding sequence (e.g., SEQ ID NO: 2) of a human SPINK5 polypeptide (e.g., SEQ ID NO: 4) under the control of a heterologous promoter integrated at each ICP4 locus (FIG. 1C); 3) a recombinant ΔICP4/ΔICP22-modified HSV-1 genome comprising an expression cassette containing the coding sequence (e.g., SEQ ID NO: 2) of a human SPINK5 polypeptide (e.g., SEQ ID NO: 4) under the control of a heterologous promoter integrated at the ICP22 locus (FIG. 1D); 4) a recombinant ΔICP4/ΔUL41-modified HSV-1 genome comprising an expression cassette containing the coding sequence (e.g., SEQ ID NO: 2) of a human SPINK5 polypeptide (e.g., SEQ ID NO: 4) under the control of a heterologous promoter integrated at each ICP4 locus (FIG. 1E); 5) a recombinant ΔICP4/ΔUL41-modified HSV-1 genome comprising an expression cassette containing the coding sequence (e.g., SEQ ID NO: 2) of a human SPINK5 polypeptide (e.g., SEQ ID NO: 4) under the control of a heterologous promoter integrated at the UL41 locus (FIG. 1F), 6) a recombinant ΔICP4/ΔICP22/ΔUL41-modified HSV-1 genome comprising an expression cassette containing the coding sequence (e.g., SEQ ID NO: 2) of a human SPINK5 polypeptide (e.g., SEQ ID NO: 4) under the control of a heterologous promoter integrated at each ICP4 locus (FIG. 1G), 7) a recombinant ΔICP4/ΔICP22/ΔUL41-modified HSV-1 genome comprising an expression cassette containing the coding sequence (e.g., SEQ ID NO: 2) of a human SPINK5 polypeptide (e.g., SEQ ID NO: 4) under the control of a heterologous promoter integrated at the UL41 locus (FIGS. 1H), and 8) a recombinant ΔICP4/ΔICP22/ΔUL41-modified HSV-1 genome comprising an expression cassette containing the coding sequence (e.g., SEQ ID NO: 2) of a human SPINK5 polypeptide (e.g., SEQ ID NO: 4) under the control of a heterologous promoter integrated at the ICP22 locus (FIG. 1I).

These modified herpes simplex virus genome vectors are transfected into engineered Vero cells that are modified to express one or more herpes virus genes. These engineered Vero cells subsequently secrete into the supernatant of the cell culture a replication-defective herpes simplex virus with the modified genomes packaged therein. The supernatant is then collected, concentrated, and sterile filtered through a 5 μm filter.

Example 2: Construction and In Vitro Analysis of an HSV Candidate Encoding Human SPINK5

The following example describes the construction of a recombinant herpes simplex virus type 1 (HSV-1) modified to express human SPINK5, and further, provides experiments showing that the recombinant virus was capable of expression functional human SPINK5 in vitro in infected human cells.

Materials and Methods

Virus Construction

The "HSV-S5" vector was generated as follows: a recombinant HSV-1 was engineered to incorporate a codon-optimized human SPINK5 expression cassette containing a heterologous promoter and polyA sequence into each of the ICP4 loci. Multiple plaques of the engineered virus putatively containing the human SPINK5 cassette were picked and screened by infection in Vero cells to test for SPINK5 expression (data not shown). The highest SPINK5 producing virus, termed "HSV-S5", was isolated and purified.

Cell Culture

All cells were cultured at 37° C. in 5% $CO_2$. Immortalized normal keratinocytes were cultured in DMEM supplemented with 10% FBS and 1% HEPES buffer. Cells were grown in 6-well plates for qPCR/qRT-PCR analyses, western blotting, and the effector secretion and functionality assays. Cells were grown in 8 chamber slides for immunofluorescence.

Viral Infections

Viral aliquots were removed from the −80° C. freezer and were left to defrost under the tissue culture laminar flow hood. Multiplicity of infection was calculated from the virus titer and target cell number, the appropriate volume of virus stock was diluted in cell culture medium to a final volume of 100 μL, and the prepared virus was incubated with the target cells for 1 hour at 37° C. After the hour-long infection, 2 mL of the appropriate cell culture medium was added to well of the 6-well plate, or in the case of 8 chamber slides, 40 μL of medium was added.

qPCR/qRT-PCR Analysis

Immortalized keratinocytes were plated in 6-well plates at $7\times10^5$ cells/well to achieve 90-100% confluence the following day. 48 hours after mock infection or infection with HSV-S5, cells were resuspended in 350 μL RLT buffer containing DTT and homogenized by passing through a QiaShredder column according to the manufacturer's protocol. DNA and RNA were isolated using an AllPrep DNA/RNA Mini kit (Qiagen) according to the manufacturer's protocol. For qPCR/qRT-PCR analysis, 50 ng of DNA or RNA were used per reaction in a total reaction volume of 25 μL. DNA quantification was determined by qPCR analysis using a Taqman® Fast Advanced Master Mix (Applied Biosystems); RNA quantification was determined by qRT-PCR analysis using Quantabio 1-Step RT-qPCR ToughMix. All samples were run in duplicate.

Western Blotting

Immortalized keratinocytes were plated in 6-well plates at $7\times10^5$ cells/well to achieve 90-100% confluence the following day. 48 hours after mock infection or infection with HSV-S5, media was aspirated, cells were recovered with gentle scraping, and cell pellets were generated by centrifugation. Cells were lysed with RIPA buffer and incubated with intermittent agitation. Next, benzonase (10U) was added to each lysate for 10 minutes at room temperature. Lysates were then mixed with 4× LDS sample buffer (Invitrogen) containing 5% 2-mercaptoethanol. Prior to loading, samples were first boiled for 10 minutes at 95° C., allowed to cool to room temperature, and then briefly centrifuged. Lysates were then run on a 4-20% Tris-Glycine gel and then transferred onto PVDF. Primary antibodies (rabbit anti-human SPINK5, R&D Systems cat. no. AF8515; rabbit anti-human GAPDH, Abcam cat. no. ab9485) were incubated with the blocked blots. Blots were then incubated with secondary antibody (goat anti-rabbit IgG-AP conjugated, Sigma) for 1 hour at room temperature, the blots were washed three times with TBS for five minutes each, and the washed blots were then incubated with AP Chromogenic substrate (Invitrogen) to allow for development of the bands.

Immunocytochemistry

Immortalized keratinocytes were plated in 8-chamber slides at $1.3\times10^5$ cells/well to achieve 90-100% confluence the following day. 48 hours after mock infection or infection with HSV-S5, cells were fixed with 2% paraformaldehyde, and were permeabilized with 0.2% Triton™ X-100 for five minutes. The cells were incubated with Powerblock (BioGenex) for 30 minutes, then were incubated with rabbit anti-human SPINK5 primary antibody (Novus Biologicals cat. no. NBP1-90509) overnight. Slides were subsequently incubated with Alexa Fluor® 488-conjugated secondary antibody, and mounted with ProLong Gold antifade reagent containing DAPI.

SPINK5 ELISA

The expression and secretion of human SPINK5 protein was assessed using a commercially available ELISA kit according to the manufacturer's protocol (LSBio). Briefly, standards or samples (media from cell culture) were added to the wells, unbound standard or sample was washed away, and a biotin-conjugated detection antibody was then added. An avidin-horseradish peroxidase conjugate was incubated in the wells to bind to the biotin, and a TMB substrate was then added resulting in quantitative colorimetric development. A sulfuric acid stop solution was added to terminate color development, and optical density of each well was measured at a wavelength of 450 nm using a Synergy H1 Hybrid Multi-Mode Reader.

SPINK5 Activity Assay

The inhibition of recombinant human Kallikrein 5 (R&D Systems) protease activity by HSV-S5-infected immortalized keratinocyte cell supernatants was evaluated using a modified method supplied by R&D Systems. Briefly, rhKLK5 (2 ng/μL) was preincubated with culture supernatants from HSV-S5-infected (or mock infected) cells for 5 minutes at room temperature. Following preincubation, the fluorogenic peptide Boc-VPR-AMC was added to a final concentration of 20 μM. Immediately after the addition of substrate, the cleavage of substrate (relative fluorescence units, RFU) was measured at Excitation 380 nm/Emission 460 nm using a Synergy H1 Hybrid Multi-Mode Reader every 70 seconds for 15 minutes.

Results

Immortalized normal human keratinocytes (HaCaTs) were infected with various multiplicities of infection (MOIs) of HSV-S5 ranging from 0.3 to 3.0. SPINK5 expression was evaluated by quantitative polymerase chain reaction (qPCR), quantitative reverse transcription PCR (qRT-PCR), western blot analysis, and an enzyme-linked immunosorbent assay (ELISA) 48 hours post-infection.

Figure 2A:
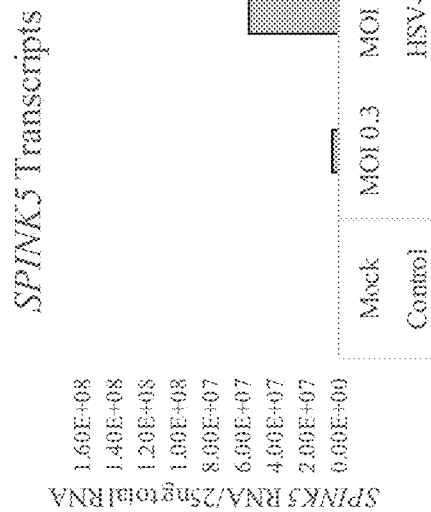
FIGS. 2A-D show human SPINK5 nucleic acid and protein analyses in immortalized normal keratinocytes infected with HSV-S5.
Figure 2B:
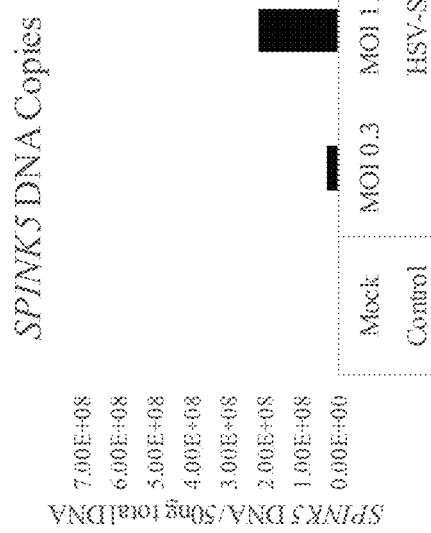
Figure 2C:
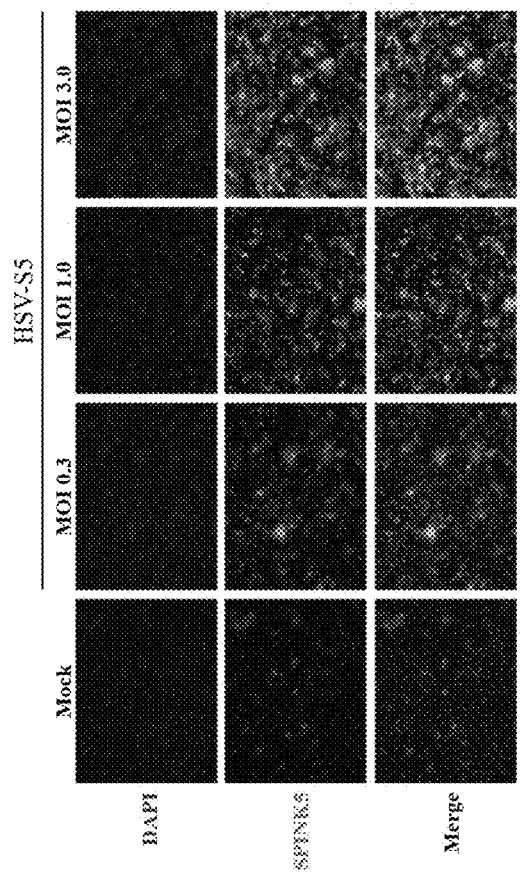

SPINK5 was detected in infected normal keratinocytes at an MOI as low as 0.3, and appeared to show a dose-dependent increase at both the DNA (FIG. 2A) and transcript (FIG. 2B) levels up to an MOI of 3.0. A concomitant dose-dependent increase in SPINK5 protein expression was observed in the cytoplasm of infected normal keratinocytes, as assessed by western blot (FIG. 2C).

Figure 2D:
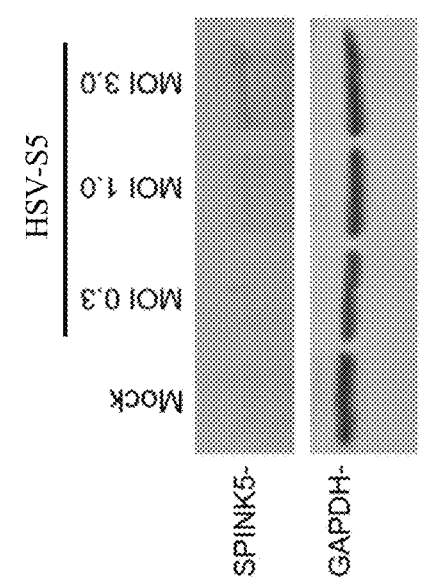

SPINK5 expression in HSV-S5-infected keratinocytes was also evaluated by immunocytochemistry (ICC). In agreement with the nucleic acid and western blot analyses, a dose-dependent increase in SPINK5 protein expression was observed by ICC analysis (FIG. 2D). 7.36% of mock infected cells were SPINK5-positive, while 27.3%, 68.48%, and 95.20% of the HSV-S5-transduced cells were SPINK5-positive when infected at a MOI of 0.3, 1.0, and 3.0, respectively. Notably, there was no significant effect of infection on either cell morphology or viability, even at high doses of HSV-S5.

Figure 3:
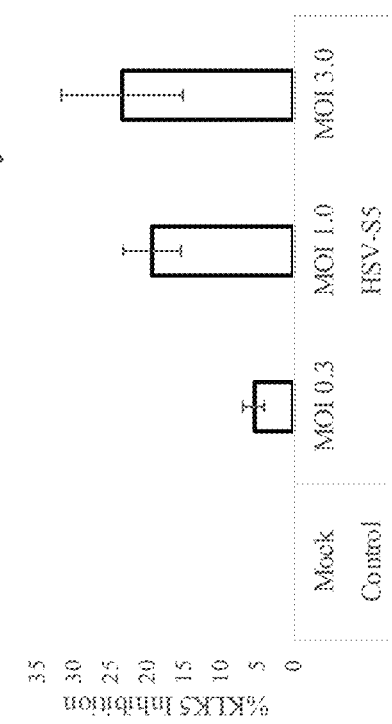
FIG. 3 shows the concentration of human SPINK5 secreted into the supernatant of cultured immortalized normal keratinocytes 48 hours after infection with HSV-S5 at the indicated MOIs, as assessed by ELISA. Cell supernatant collected from uninfected (mock) immortalized normal keratinocytes was used as a negative control.

Because endogenous SPINK5 is a naturally secreted protein, it was important to show that the HSV-S5-expressed exogenous human SPINK5 could also be effectively secreted from infected cells, thus supporting HSV-S5's use in SPINK5-deficient patients. As such, SPINK5 protein levels were quantitated in cell culture medium taken from infected HaCaTs. SPINK5 was successfully secreted from infected normal keratinocytes in a dose-dependent manner (FIG. 3).

Finally, functionality of the HSV-S5-expressed human SPINK5 secreted from infected keratinocytes was confirmed using an enzymatic inhibition assay that measured SPINK5's ability to inhibit a native target of the SPINK5, the human serine protease Kallikrein 5 (KLK5). Briefly, recombinant human KLK5 was preincubated with cell culture supernatants collected from HSV-S5-infected HaCaTs (supernatant from mock-infected cells was used as a control). Following this preincubation, a synthetic, non-natural peptide substrate of human KLK5 (Boc-VPR-AMC) was added to the samples, and KLK5-mediated cleavage of the substrate was assessed in each sample. Using this experimental approach, the proteolytic activity of KLK5 (and its inhibition by SPINK5) could be directly quantitated by determining fluorescence resulting from the liberation of the previously quenched fluorescent AMC moiety of Boc-VPR-AMC after hydrolysis of the Arg-AMC amide bond by KLK5.

Figure 4:
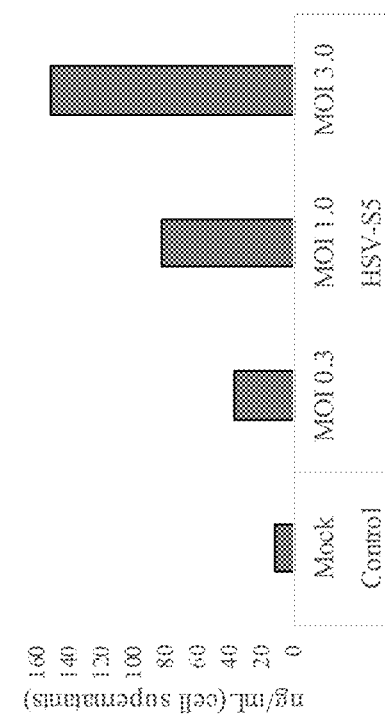
FIG. 4 shows the percent inhibition in proteolytic activity of recombinant human Kallikrein 5 (KLK5) after incubation with cell culture supernatants collected from immortalized normal keratinocytes infected with HSV-S5 at the indicated MOIs, as assessed in a fluorometric assay employing a synthetic, non-natural peptide substrate of human KLK5. Cell supernatant collected from uninfected (mock) immortalized normal keratinocytes was used as a negative control. Data is presented as the average±SEM.

As expected, no inhibition of KLK5 activity was observed when preincubating the protease with cell culture supernatant obtained from mock-infected keratinocytes. In contrast, infection with HSV-S5 resulted in a dose-dependent increase in functional SPINK5 expression, as observed by increased KLK5 inhibition when the protease was pretreated with cell culture supernatant collected from keratinocytes infected with increasing MOIs of HSV-S5 (FIG. 4).

Taken together, the data presented in this example demonstrate that an engineered herpes simplex virus can efficiently transduce normal human keratinocytes and produce high levels of exogenous SPINK5 after transduction. Importantly, while HSV-S5 was capable of rescuing/supplementing SPINK5 expression in human cells, the vector did not induce any major toxicity in any of the studies. In addition, the data presented herein indicates that HSV-S5 is capable of inducing secretion of functional SPINK5 at therapeutically relevant levels.

Example 3: In Vivo Characterization of HSV-S5

The following example describes in vivo experiments establishing multiple routes of delivery for HSV-S5 in healthy immunocompetent animals. These studies were conducted in BALB/c mice because there are no practical disease animal models for SPINK5 deficiency, as homozygous deletion of SPINK5 is neonatal-lethal in animals.

Materials and Methods

All procedures conducted in this example were in compliance with applicable animal welfare acts and were approved by the local Institutional Animal Care and Use Committee (IACUC).

Topical HSV-S5 Administration

The backs of mice were shaved, and hair follicles were removed with a hair removal product before further manipulations. Tape stripping (using Tegaderm™) was carried out as described previously (Ekanayake-Mudiyanselage et al. J Invest Dermatol (1998), 111(3):517-23). After tape stripping, two sites on the backs of each mouse were treated topically with the appropriate test article. To contain the topical formulation at the treatment site, sterile plastic wells covered by a transparent adhesive dressing were adhered to the skin of the animals using surgical glue. HSV-S5 (or vehicle control) formulated in a methylcellulose gel carrier was then applied to the treatment sites via injection through the transparent adhesive dressing.

Intradermal HSV-S5 Injection

The backs of mice were shaved before further manipulations. HSV-S5 (or vehicle control) was then injected intradermally to two sites in the backs of each mouse.

Tissue Harvest

After infection and the subsequent recovery period, the animals were euthanized by $CO_2$ inhalation followed by cervical dislocation, and the treatment sites were removed using an 8 mm punch biopsy. One half of each biopsy was quick-frozen in liquid nitrogen for qPCR/qRT-PCR analysis, while the other half was processed for immunofluorescence analysis and H&E staining.

qPCR/qRT-PCR Analyses

Quick-frozen biopsy halves were stored at −80° C. until analysis. For processing and analysis, samples were resuspended in 350 µL RLT buffer prepared with fresh DTT according to the manufacturer's protocol (Qiagen) and were sonicated three times at 25% amplitude with intermittent incubation for 1 minute on ice. DNA and RNA extractions were performed using the Qiagen AllPrep DNA/RNA extraction kit according to the manufacturer's protocol (with the inclusion of the optional DNase treatment step for the RNA samples). Both DNA and RNA samples were resuspended in distilled deionized RNase free water and quantified spectrophotometrically on a Synergy™ H1 microplate reader (BioTek).

Absolute quantification of SPINK5 DNA and RNA copies was performed by TaqMan Real Time PCR analysis using custom, transgene-specific primer/probe pairs. Taqman® Fast Advanced Master Mix (Applied Biosystems) was used for DNA quantification (qPCR) and Quantabio 1-Step RT-qPCR ToughMix was used for RNA quantification (qRT-PCR). All samples were run in duplicate, and copy number was determined using a standard curve derived from a dilution series of plasmid standard containing a known copy number of the SPINK5 transgene.

Immunofluorescence Staining

5 µm sections were taken from OCT frozen tissue, mounted on slides, and air dried for up to 1 hour. The slides were then dipped in 100% methanol (MeOH) for 10 minutes at −20° C. and left to air dry. The methanol-fixed sections were rehydrated by washing 3 times in PBS (5 minutes each) at room temperature, followed by an incubation in 3% $H_2O_2$ for 10 minutes at room temperature, and 3 washes with PBS. The samples were then incubated with a blocking solution (Power Block) for 10 minutes at room temperature in a humidified chamber. Excess blocking solution was removed, and the sections were stained with a drop of primary antibody (Ab) solution (1:200 final dilution) prepared in antibody diluent buffer (30 to 50 µL primary Ab solution/section). The sections were incubated with the primary antibody for 16 hours at 4° C. or 1 hour at room temperature, washed three times in TBST (TBS+0.025% Triton X-100) for 5 minutes at room temperature, and secondary Ab was applied at a 1:200 dilution in antibody diluent buffer for 30 minutes at room temperature in a humidified chamber. Slides were once again washed three times with TBST, and the stained sections were mounted with mounting media (ProLong™ Gold Antifade Mountant with DAPI, ThermoFisher, cat. no. P36931) and covered with a coverslip. The sections were imaged after dehydration (approximately 24 hours) using an ECHO Fluorescence Microscope. The primary and secondary antibodies used in this study are presented in Table 1.

TABLE 1 antibodies used for immunofluorescence

| Antibody: | Primary/Secondary: | Vendor: | Cat. No.: |
|---|---|---|---|
| Rabbit anti-SPINK5 | Primary | R&D Systems | AF8515 |
| Mouse anti-Filaggrin | Primary | BOSTER | M01063 |
| Anti-rabbit Alexa Fluor ® 488 | Secondary | Invitrogen | A11034 |
| Anti-mouse Alexa Fluor ® 594 | Secondary | Abcam | Ab150120 |

Hematoxylin and Eosin (H&E) Staining

5 µm sections were taken from cryopreserved tissue, mounted on slides, and air dried for up to 1 hour. The dried slides were rehydrated by soaking in double-distilled water for 2 minutes at room temperature. Sections were then incubated in Hematoxylin Gill 2× (VWR) for 2 minutes at room temperature, followed by being dipped 2 to 3 times in acid alcohol, dipped 3 to 4 times in Blue in Ammonia water, and incubated in eosin (Eosin Y Solution 1%, VWR) for 2 minutes. Samples were rinsed 3 to 4 times with tap water between each step. The stained and rinsed sections were gradually dehydrated with ethanol (EtOH) by first rinsing twice with 95% EtOH for 2 minutes each, then twice with 100% EtOH for 2 minutes each. Sections were then cleared through three rinses with Histo-Clear for 2 minutes each, mounted with mounting media (Permount™ Mounting Medium), and covered with a coverslip. The sections were imaged approximately 24 hours after dehydration using a brightfield microscope Results A single dose pharmacology study was conducted in immunocompetent BALB/c mice to determine feasibility of administering human SPINK5 via topical and/or intradermal administration of HSV-S5. A total of 4 BALB/c mice were used for this study. Prior to test article administration, the backs of the mice were shaved, and hair follicles were removed using a chemical hair removal product. Next, at the sites of topical treatment, the exposed skin was tape stripped nine times to disrupt/remove the stratum corneum and $1 \times 10^8$ plaque forming units (PFUs) of HSV-S5 (or vehicle control) formulated in a gel carrier were topically administered to two regions of the tape stripped skin on each mouse. For intradermal administration, $1 \times 10^8$ PFUs of HSV-S5 (or vehicle control) were injected at two parallel sites on the back of each animal. Table 2 below provides a synopsis of the experimental design.

TABLE 2 study design and test article administration

| Group No. | N | Test Article | Route of Administration | Location; No. of Sites | Termination |
|---|---|---|---|---|---|
| 1 | 1 | Vehicle | Topical & Intradermal | Back; 2 topical, 2 intradermal | 48 hours |
| 2 | 3 | HSV-S5 | Topical & Intradermal | Back; 2 topical, 2 intradermal | 48 hours |

Figure 5A:
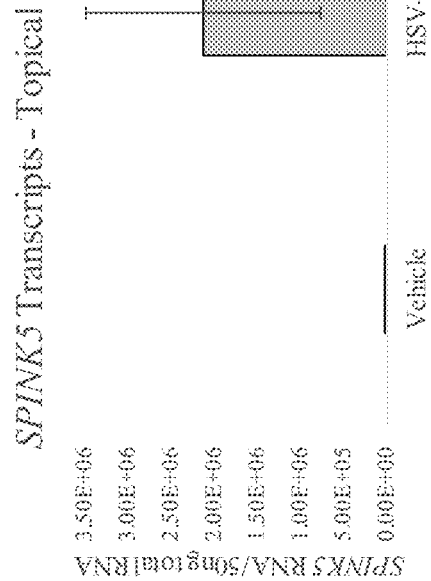
FIGS. 5A-F show nucleic acid and protein analyses, as well as histology, of skin biopsies harvested from control- or HSV-S5-treated BALB/c mice.
Figure 5C:
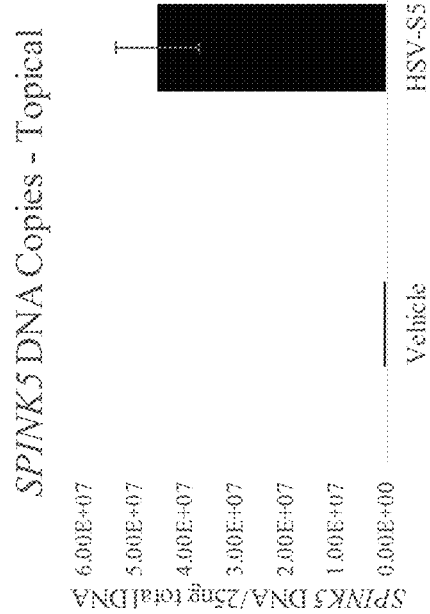
Figure 5B:
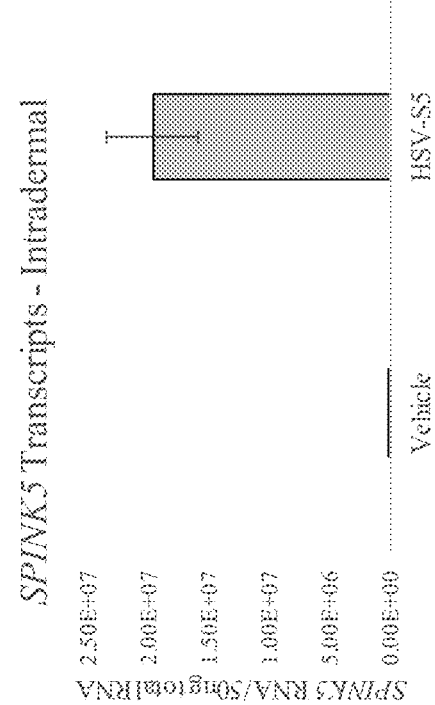
Figure 5D:
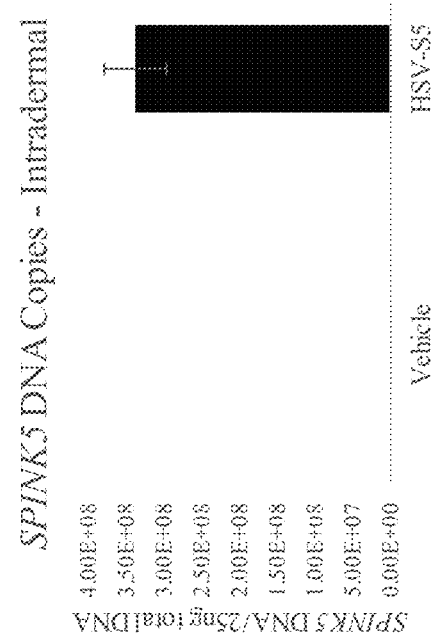

48 hours post-administration, a full thickness 8 mm biopsy was taken from each treatment site and split in half. One half of each section was flash frozen in liquid nitrogen and subsequently processed for qPCR and qRT-PCR analysis in order to quantify SPINK5 DNA copy numbers and transcript levels, respectively. The remaining half of each biopsy was embedded in OCT for immunofluorescence (IF).

qPCR analysis of the topically treated, tape-stripped skin indicated that the engineered HSV genomes encoding the human SPINK5 transgene efficiently transduced disrupted skin of immunocompetent animals (FIG. 5A). Not only did the genomes efficiently enter the targeted tissues, but the recombinant human SPINK5 was robustly expressed after infection, as assessed by qRT-PCR analysis (FIG. 5B). Similar results were found after intradermal injection of HSV-S5 into fully intact skin at both the DNA (FIG. 5C) and RNA (FIG. 5D) levels. No SPINK5 DNA or RNA was detected in the vehicle treated tissues, indicating specificity of the assay for the HSV-S5 test article.

Figure 5E:
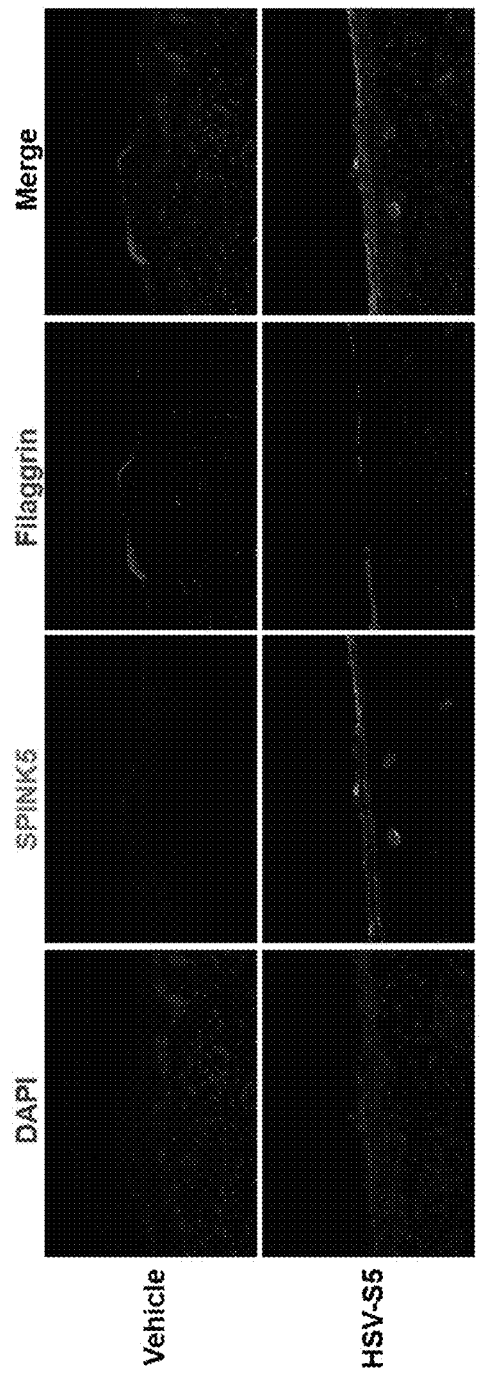

SPINK5 expression in cryosections harvested from topically treated animals was determined by immunofluorescent analysis using an anti-human SPINK5 antibody. To confirm that the SPINK5 expressed from HSV-S5 was correctly localized to the cornified layer of the epidermis, the samples were also counterstained for mouse Filaggrin, another structural protein localized to this region of the skin (FIG. 5E). This data demonstrated that topical application of HSV-S5 led to successful transduction of mouse skin, inducing robust expression of the encoded human transgene in the correct layer of the epidermis.

Figure 5F:
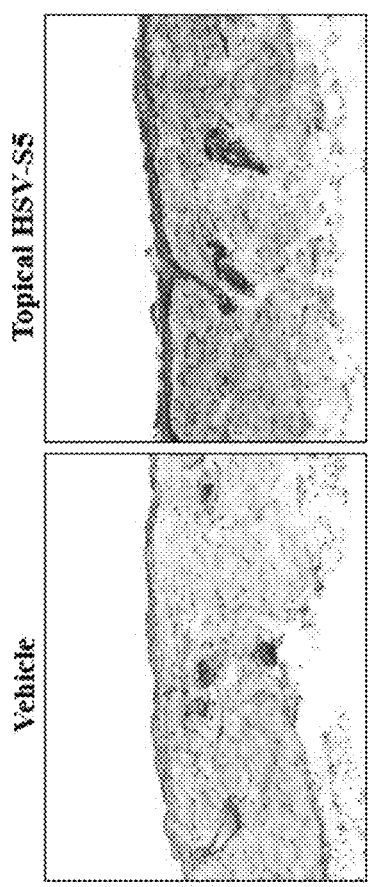

Histological evaluation of topically treated skin showed no inflammatory infiltration at the treated site, and the HSV-S5 treated skin appeared morphologically normal (comparable to vehicle-treated skin) (FIG. 5F), demonstrating the safety of this therapy.

Taken together, the in vivo data presented herein clearly demonstrates that (1) HSV-S5 successfully expresses human SPINK5 in vivo when administered topically and intradermally to immunocompetent mice, and (2) the recombinant SPINK5 is expressed in, and localizes to, the appropriate region of the epidermis. In addition, no inflammatory infiltration or gross structural changes to the skin were observed at the HSV-S5-treated sites, confirming that HSV-S5 is well tolerated. Without wishing to be bound by theory, it is believed that these data, paired with the results of the in vitro testing, provide strong support for the safe and effective use of topical or intradermal HSV-S5 for the transient and repeated delivery of human SPINK5. In addition, without wishing to be bound by theory, it is believed that HSV-S5 has the potential to be a clinically beneficial, non-invasive gene therapy candidate for the treatment of Netherton Syndrome.

What is claimed is:

1. A pharmaceutical composition comprising:
   (a) a replication defective herpes simplex virus comprising a recombinant herpes simplex virus genome, wherein the recombinant herpes simplex virus genome comprises one or more polynucleotides encoding a Serine Protease Inhibitor Kazal-type 5 (SPINK5) polypeptide; and
   (b) a pharmaceutically acceptable excipient,
   wherein the one or more polynucleotides encoding the SPINK5 polypeptide are operably linked to a promoter suitable for transcription in a mammalian cell.

2. The pharmaceutical composition of claim 1, wherein the recombinant herpes simplex virus genome is a recombinant herpes simplex virus type 1 (HSV-1) genome.

3. The pharmaceutical composition of claim 2, wherein the recombinant HSV-1 genome comprises an inactivating mutation in a herpes simplex virus gene selected from the group consisting of Infected Cell Protein (ICP) 0, ICP4, ICP22, ICP27, ICP47, thymidine kinase (tk), Long Unique Region (UL) 41, and UL55.

4. The pharmaceutical composition of claim 1, wherein the SPINK5 polypeptide is a human SPINK5 polypeptide.

5. The pharmaceutical composition of claim 1, wherein the SPINK5 polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from the group consisting of SEQ ID NOS: 7-25.

6. The pharmaceutical composition of claim 1, wherein the recombinant herpes simplex virus genome comprises an inactivating mutation in one or both copies of an ICP4 herpes simplex virus gene.

7. The pharmaceutical composition of claim 1, wherein the pharmaceutically acceptable excipient is suitable for topical, transdermal, subcutaneous, intradermal, and/or transmucosal administration.

\* \* \* \* \*

SEQUENCE LISTING

```
Sequence total quantity: 26
SEQ ID NO: 1              moltype = DNA   length = 3285
FEATURE                   Location/Qualifiers
source                    1..3285
                          mol_type = unassigned DNA
                          organism = Mus musculus
SEQUENCE: 1
atgaagatag ccacagtgtc agtgcttctg cccttggctc tttgcctcat acaagatgct    60
gccagtaaga atgaagatca ggaaatgtgc catgaatttc aggcatttat gaaaaatgga   120
aaactgttct gtcccagga taagaaattt tttcaaagtc ttgatggaat aatgttcatc   180
aataaatgtg ccacgtgcaa aatgatactg gaaaagaag caaaatcaca gaagagggcc   240
aggcatttag caagagctcc caaggctact gccccaacag agctgaattg tgatgatttt   300
aaaaaaggag aaagagatgg ggatttttatc tgtcctgatt attatgaagc tgtttgtggc   360
acagatggga aaacatatga caacagatgt gcactgtgtg ctgagaatgc gaaaaccggg   420
tcccaaattg gtgtaaaaag tgaaggggaa tgtaagagca gtaatccaga gcaggatgta   480
tgcagtgctt ttcggccctt tgttagagat ggaagacttg gatgcacaag ggaaaatgat   540
cctgttcttg gtcctgatgg gaagacgcat ggcaataagt gtgcaatgtg tgctgagctg   600
ttttttaaaag aagctgaaaa tgccaagcga gagggtgaaa ctagaattcg acgaaatgct   660
gaaaaggatt tttgcaagga atatgaaaaa caagtgagaa atggaaggct tttttgtaca   720
cgggagagtg atccagtccg tggccctgac ggcaggatgc atggcaacaa atgtgccctg   780
tgtgctgaaa ttttcaagca gcgtttttca gaggaaaaca gtaaaacaga tcaaaatttg   840
ggaaaagctg aagaaaaaac taaagttaaa agagaaattg tgaaactctg cagtcaatat   900
caaaatcagg caaagaatgg aatacttttc tgtaccagag aaaatgaccc tattcgtggt   960
ccagatggga aaatgcatgg caacttgtgt tccatgtgtc aagcctactt ccaagcagaa  1020
aatgaagaaa agaaaaaggc tgaagcacga gctagaaaca aaagagaatc tggaaaagca  1080
acctcatatg cagagctttg cagtgaatat cgaaagcttg tgaggaacgg aaaacttgct  1140
tgcaccagag agaacgatcc tatccagggc ccagatggga agtgcatgg caacacctgc  1200
tccatgtgtg aggtcttctt ccaagcagaa gaagaagaaa agaaaaagaa ggaaggtaaa  1260
tcaagaaaca aaagacaatc taagagtaca gcttcctttg aggagttgtg tagtgaatac  1320
cgcaaatcca ggaaaaacgg acggcttttt tgcaccagag agaatgaccc catccagggc  1380
ccagatggaa aaatgcatgg caacacctgc tccatgtgtg aggcctttctt tcaacaagaa  1440
gaaagagcaa gagccaaggc taaaagagaa gctgcaaagg aaatctgcag tgaatttcgg  1500
gaccaagtga ggaatggaac acttatatgc accagggagc ataatcctgt ccgtggccca  1560
gatggcaaaa tgcatggaaa caagtgtgcc atgtgtgcca gtgtgttcaa acttgaagaa  1620
gaagagaaga aaatgataa agaagaaaaa gggaaagtcg aggctgaaaa agttaagaga  1680
gaagcagttc aggagctgtg cagtgaatat cgtcattatg tgaggaatgg acgactcccc  1740
tgtaccagag agaatgatcc tattgagggt ctagatggga aaatccacgg caacacctgc  1800
tccatgtgtg aagccttctt ccagcaagaa gcaaaagaaa aagaaagagc tgaacccaga  1860
gcaaagagtca aaagagaagc tgaaaaggag acatgcgatg aatttcggag acttttgcaa  1920
aatggaaaac ttttctgcac aagagaaaat gatcctgtgc gtgcccaga tggcaagacc  1980
catggcaaca agtgtgccat gtgtaaggca gtcttccaga aagaaaatga ggaaagaaag  2040
aggaaagaag aggaagatca gagaaatgct gcaggacatg gttccagtgg tggtggagga  2100
ggaaacactc aggacgaatg tgctgagtat cgggaacaaa tgaaaaatgg aagactcagc  2160
tgtactcggg agagtgatcc tgtacgtgat gctgatggca aatcgtacaa caatcagtgt  2220
accatgtgta aagcaaaatt ggaaagagaa gcagagagaa aaaatgagta ttctcgctcc  2280
agatcaaatg ggactggatc agaatcaggg aaggatacat gtgatgagtt tagaagccaa  2340
atgaaaaatg gaaaactcat ctgcactcga gaaagtgacc ctgtccgggg tccagatggc  2400
aagacacatg gcaataagtg tactatgtgt aaggaaaaac tggaaaggga agcagctgaa  2460
aaaaaaaaga aagaggatga agacaggagc aatacaggag aaaggagcaa tacaggagaa  2520
aggagcaatg acaaagagga tctgtgtcgt gaatttcgaa gcatgcagag aaatggaaag  2580
cttatctgca ccagagaaaa taaccctgtt cgaggcccat atgcaagat gcacatcaat  2640
aaatgtgcta tgtgtcagag catctttgat cgagaagcta atgaaagaaa aagaaagat  2700
gaagagaaat caagtagcaa gccctcaaat aatgcaaagg accagtgcag acaggttcag  2760
aatgaagcgg aggatgcaaa atttagacaa cctgggcgtt ccttggcctc tgttgccagg  2820
atgagtacag atgagtgcag tgaatttcga aactatataa ggaacaatga actcatctgc  2880
cctagagaga atgacccagt gcacggtgct gatgaaagt tctatacaaa caagtgctac  2940
atgtgcagag ctgtcttttct aacagaagct ttggaaaggg caaagcttca agaaaagcca  3000
tcccatgtta gagcttctca agaggaagac agcccagact ctttcagttc tctggattct  3060
gagatgtgca aagactaccg agtattgccc aggataggtt atctttgtcc aaaggattta  3120
aagcctgtct gtggtgacga tggccaaacc tacaacaatc cttgcatgct ctgtcatgaa  3180
aacctgatac gccaaacaaa tacacacatc cgcagtacag gaagtgtga ggagagcagc  3240
accccaggaa ccaccgcagc cagcatgccc ccgtctgacg aatga                   3285

SEQ ID NO: 2              moltype = DNA   length = 3285
FEATURE                   Location/Qualifiers
misc_feature              1..3285
                          note = Synthetic Construct
source                    1..3285
                          mol_type = other DNA
                          organism = synthetic construct
SEQUENCE: 2
```

```
atgaagatcg ccaccgtgtc tgtgctgctg cctctggctc tgtgcctgat tcaggatgcc      60
gccagcaaga acgaggacca agagatgtgc cacgagttcc aggcctttat gaagaacggc     120
aagctgttct gccctcaaga caagaagttc ttccagagcc tggacggcat catgttcatc     180
aacaagtgcg ccacatgcaa gatgatcctg aaaaagagg ccaagagcca gaagcgggcc      240
agacaccttg ctagagcccc taaagccacc gctcctaccg agctgaactg cgacgacttc     300
aagaaaggcg agcgcgacgg cgacttcatc tgccccgatt attacgaggc cgtgtgcgc     360
accgatggca agacctacga taacagatgc gccctgtgcg ccgagaatgc caagacagga     420
tctcagatcg gcgtgaagtc tgagggcgag tgcaagagca gcaaccccga gcaggatgtg     480
tgcagcgcct tcagacccct cgtcagagat ggcagactgg gctgcaccag agaaaacgat     540
cctgtgctga gccctgacgg caagacacac ggaaacaagt gtgctatgtg tgccgagctg     600
ttcctgaaag aggccgaaaa cgccaagaga gagggcgaga cacggatcag aagaaacgcc     660
gagaaggact tctgcaaaga atacgagaag caagtgcgga acggacgcct gttctgtacc     720
cgggaaagcg atccagtcag aggccccgat ggaagaatgc acggcaacaa atgcgcactg     780
tgtgctgaga tcttcaagca gcggttcagc gaggaaaaca caagaccga gcagaacctg     840
ggcaaagcca agaaaagac caaagtgaag cgcgagatcg tgaagctgtg cagccagtac     900
cagaaccagg ccaagaatgg catcctgttc tgcacacgcg agaacgaccc catcagagga     960
cccgacggaa agatgcatgg aaacctgtgc agcatgtgcc aggcctactt ccaggccgag    1020
aacgaagaga agaagaaggc cgaagccagg gccagaaaca acggcaaggcc               1080
accagctacg ccgaactgtg tagcgagtac agaaagctcg tgcggaatgg caagctggcc    1140
tgcactaggg aaaatgaccc tattcaggga ccagacggca aggtgcacgg aatacctgt    1200
tccatgtgcg aggtgttctt tcaggccgag aagaggaaa aaagaagaa agagggcaag    1260
tcccgggaaca agcggcagag caagagcacc gccagcttcg aggaactgtg ctccgagtgc    1320
cggaagtcca aaagaatgg ccggcttttc tgcacgagag agaatgatcc catccagggg    1380
cctgatggca aaatgcatgg caatacttgc tctatgtgcg aggcattttt ccagcaagag    1440
gaacgggcca gagccaaggc caaaagagag ccgccaaaga gatctgcag cgagtttagg    1500
gaccaagtcc gcaacggcac cctgatctgc accagggaac acaaccctgt cagagggcca    1560
gacgggaaaa tgcacgggaa caagtgtgcc atgtgcgcct ccgtgttcaa gctggaagaa    1620
gaagaaaaga aaaacgacaa agaagagaag ggaaaagtcg aagccgagaa agtgaagagg    1680
gaagccgtgc aagaactctg ttctgagtac cggcactacg tccggaacgg cagactgcct    1740
tgtactcggg aaaacgaccc aatcgaagga ctggacggga agatccatgg caacaccgt    1800
agtatgtgcg aggcattctt tcaacaagaa gccaaagaaa aagagcgggc cgagcctcgg    1860
gccaaagtca aagagaagc tgagaaagag acatgcgacg agttccggcg gctgctgcag    1920
aatggaaaac tcttctgtac acgtgaaaat gatcccgtgc ggggaccaga tggaaagacc    1980
catgggaaca aatgcgctat gtgcaaggcc gtgttccaaa agagaatga ggaacgcaag    2040
cggaaaagag aagaagatca gcggaacgcc gctggccacg gatctagtgg cggaggtggt    2100
ggaaatacccc aggacgagtg tgccaataca cgggaacaga tgaagaatgg aaggctgagc    2160
tgcacacggg aatctgaccc cgttagagat gccgacggca gtcctacaa caaccagtgc    2220
accatgtgta agccaagct cgagcgcgag ccgagcgga agaatgagta cagcagaagc    2280
cggtctaacg gcaccggctc tgagtctggc aaggatacct cgcgagtt cagatcccag    2340
atgaagaacg ggaaactcat ctgcacaaga gaatcagacc cagtccgggg acctgacggg    2400
aaaactcatg gcaacaagtg cacaatgtgc aaagagaaac tggaacgcga ggctgccgag    2460
aagaaaaaga aagaggacga ggatcggagc aacaccggcg agagatctaa taccggcgag    2520
cggagcaatg acaaaaggga cctctgccgg gaattccgct ccatgcagag aaacggaaag    2580
ctgatatgta cgcgcgagaa caatcccgtt cggggcccctt atgggaagat gcacattaac    2640
aaaatgtgcaa tgtgccagag catcttcgac agagaggcca acgaacgcaa aaagaaggat    2700
gaagagaagt ccagcagcaa gcccagcaac aacgccaagg accagtgcag acaggtgcag    2760
aacgaggctg aggacgccaa gtttagacag cccggtagaa gcctggcctc tgtggccaga    2820
atgagcaccg atgagtgcag cgaattccgg aactatatcc ggaacaacga gctgatctgt    2880
ccgcgagaga atgaccctgt gcatggcgcc gatggaaagt ctacaccaa caagtgttat    2940
atgtgcagag ccgtctttct gacagaggcc ctggaaagag ccaagctgca agagaagcct    3000
tctcacgtgc gggcctctca agaaggacac agccctgata gcttcagcag cctggacagc    3060
gagatgtgca aggactacag agtgctgccc cggatcggct atctgtgccc caaggatctg    3120
aagcctgtgt gtggcgacga cggccagaca tacaacaatc cctgcatgct gtgtcacgag    3180
aacctgatcc ggcagaccaa cacacacatc cggtccaccg gcaagtgcga agagtctagc    3240
acacctggaa caaccgccgc ctctatgcct cctagcgacg aatga                    3285

SEQ ID NO: 3               moltype = DNA   length = 2751
FEATURE                    Location/Qualifiers
source                     1..2751
                           mol_type = unassigned DNA
                           organism = Homo sapiens
SEQUENCE: 3
atgaagatag ccacagtgtc agtgcttctg cccttggctc tttgcctcat acaagatgct      60
gccagtaaga atgaagatca ggaaatgtgc catgaatttc aggcatttat gaaaaatgga     120
aaactgttct gtcccagga taagaaattt tttcaaagtc ttgatggaat aatgttcatc     180
aataaatgtg ccacgtgcaa aatgatactg aaaaagaag caaaatcaca gaagagggcc     240
aggcatttag caagagctcc caaggctact gccccaacag agctgaattg tgatgatttt     300
aaaaaaggaa aagagatgg ggattttatc tgtcctgatt attatgaagc tgtttgtggc     360
acagatggga aaacatatga caacagatgt gcactgtgtg ctgagaatgc gaaaaccgga     420
tcccaaattg gtgtaaaaag tgaagggaa tgtaagagca gtaatccaga gcaggatgta     480
tgcagtgctt tcggcccctt tgttagagat ggaagacttg gatcacaag ggaaaatgat     540
cctgttcttg gtcctgatgg gaagacgcat ggcaataagt gtgcaatgtg tgctgagctg     600
tttttaaaag aagctgaagga tgccaagcga gggtgaaa ctagaattcg acgaaatgct     660
gaaaaggatt tttgcaagga atatgaaaaa caagtggcag ttttgtaca                720
cgggagagtg atccagtccg tggccctgac ggcaggatgc atgcaacaa atgtgccctg     780
tgtgctgaaa ttttcaagca gcgttttca gaggaaaaca gtaaacaga tcaaatttg     840
ggaaaagctg aagaaaaaac taagttaaa agagaaattg tgaaactctg cagtcaatat     900
caaaatcagg caaagaatgg aatacttttc tgtaccagag aaaatgaccc tattcgtggt     960
ccagatggga aatgcatgg caacttgtgt tccatgtgtc aagcctactt ccaagcagaa    1020
```

```
aatgaagaaa agaaaaaggc tgaagcacga gctagaaaca aaagagaatc tggaaaagca  1080
acctcatatg cagagctttg cagtgaatat cgaaagcttg tgaggaacgg aaaacttgct  1140
tgcaccagag agaacgatcc tatccagggc ccagatggga aagtgcatgg caacacctgc  1200
tccatgtgtg aggtcttctt ccaagcagaa gaagaagaaa agaaaaagaa ggaaggtaaa  1260
tcaagaaaca aaagacaatc taagagtaca gcttcctttg aggagttgtg tagtgaatac  1320
cgcaaatcca ggaaaaacgg acggcttttt tgcaccagag agaatgaccc catccaggyc  1380
ccagatggaa aaatgcatgg caacacctgc tccatgtgtg aggccttctt caacaagaa  1440
gaaagagcaa gagcaaaggc taaagagaaa gctgcaaagg aaatctgcag tgaatttcgg  1500
gaccaagtga ggaatggaac acttatatgc accagggagc ataatcctgt ccgtgggcca  1560
gatgcaaaa tgcatggaaa caagtgtgcc atgtgtgcca gtgtgttcaa acttgaagaa  1620
gaagagaaga aaaatgataa agaagaaaaa gggaaagtcg aggctgaaaa agttaagaga  1680
gaagcagttc aggagctgtg cagtgaatat cgtcattatg tgaggaatgg acgactcccc  1740
tgtaccagag agatgatcc tattgagggt ctagatggga aaatccacgg caacacctgc  1800
tccatgtgtg aagccttctt ccagcaagaa gcaaaagaaa aagaaaagac tgaacccaga  1860
gcaaaagtca aagagaagc tgaaaaggag acatgcgatg aatttcggag actttttgcaa  1920
aatgaaaac ttttctgcac aagagaaaat gatcctgtgc gtggcccaga tggcaagacc  1980
catggcaaca agtgtgccat gtgtaaggca gtcttccaga agaaaatgca ggaaagaaag  2040
aggaaagaag aggaagatca gagaaatgct gcaggacgatg gttccagtgg tggtggagga  2100
ggaaacactc aggacgaatg tgctgagtat cgggaacaaa tgaaaaatgg aagactcagc  2160
tgtactcggg agagtgatcc tgtacgtgat gctgatggca aatcgtacaa caatcagtgt  2220
accatgtgta aagcaaaatt ggaaagagaa gcagagagaa aaaatgagta ttctcgctcc  2280
agatcaaatg ggactggatc agaatcaggg aaggatacat gtgatgagtt tagaagccaa  2340
atgaaaaatg gaaactcat ctgcactcga gaaagtgacc ctgtccgggg tccagatggc  2400
aagacacatg gcaataagtg tactatgtgt aaggaaaaac tggaaaggga agcagctgaa  2460
aaaaaaaaga aagaggatga agacaggagc aatacaggag aaaggagcaa tacaggagaa  2520
aggagcaatg acaaagagga tctgtgtcgt gaatttcgaa gcatgcagag aaatggaaag  2580
cttatctgca ccagagaaaa taaccctgtt cgaggcccat atggcaagat gcacatcaat  2640
aaatgtgcta tgtgtcagag catctttgat cgagaagcta atgaaagaaa aagaaagat  2700
gaagagaaat caagtagcaa gccctcaaat aatgcaaagg ttatttatta a           2751

SEQ ID NO: 4           moltype = DNA   length = 2751
FEATURE                Location/Qualifiers
misc_feature           1..2751
                       note = Synthetic Construct
source                 1..2751
                       mol_type = other DNA
                       organism = synthetic construct
SEQUENCE: 4
atgaagatcg ccaccgtgtc tgtgctgctg cctctggctc tgtgcctgat tcaggatgcc   60
gccagcaaga acgaggacca agagatgtgc cacgagttcc aggcctttat gaagaacggc   120
aagctgttct gccctcaaga caagaagttc ttccagagcc tggacggcat catgttcatc   180
aacaagtgcg ccacatgcaa gatgatcctg aaaaagagg ccaagagcca aagcgggcc     240
agacacctg ctagagcccc taaagccacc gctcctaccg agtcgaactg cgacgacttc    300
aagaaaggcg agcgcgacgg cgacttcatc tgccccgatt attacgaggc cgtgtgcggc   360
accgatggca agacctacga taacagatgc gccccgtgcg ccgagaatgc caagacagga   420
tctcagatcg gcgtgaagtc tgagggcgag tgcaagagca gcaaccccga gcaggatgtg   480
tgcagcgcct tcagacccctt cgtcagagat ggcagactgg gctgcaacga agaaaacgat   540
cctgtgctgg gccctgacgg caagacacac ggaaacaagt gtgctatgtg tgccgagctg   600
ttcctgaaag aggccgaaaa cgccaagaga gagggcgaga cacggatcag aagaaacgcc   660
gagaaggact tctgcaaaga atacgagaag caagtgcgga acgacgcct gttctgtacc   720
cgggaaaagcg atccagtcag aggccccgat ggaagaatgc acggcaacaa atgcgcactg   780
tgtgctgaga tcttcaagca gcggttcagc gaggaaaaca gcaagaccga ccagaacctg   840
ggcaaagccg aagaaaagac caaagtgaag cgcgagatcg tgaagctgtg cagccagtac   900
cagaaccagg ccaagaatgg catcctgttc tgcacgcgcg agaacgaccc catcagagga   960
cccggcaa agatgcatgg aaactcttgc agcatgtgcg aggcctactt ccaggccgaa   1020
aacgaagaga agaagaaggc cgaagccagg ccagaaacac agagaaaaag cggcaaggcc   1080
accagctacg ccgaactgtg tagcgagtac agaaagctcg tgcggaatgg caagctggcc   1140
tgcactaggg aaaatgaccc tattcaggga ccagacggca agtgcacgg aatacctgt    1200
tccatgtgcg aggtgttctt tcaggccgag gaagagaaa aaagaagaa agagggcaag   1260
tcccggaaca agcggcagg caagagcgcc gccagcttcg aggaactgtg ctccgagtac   1320
cggaagtcca gaaagaatgg ccggcttttt tgcacgagag agaatgatcc catccagggc   1380
cctgatggca aaatgcatgg caatacttgc tctatgtgcg aggcattttt ccagcaagag   1440
gaacgggcca gagccaaggc caaagagag gccgccaaag agatctgcag cgagtttagg   1500
gaccaagtcc gcaacggcac cctgatctgc accagggaac acaaccctgt cagagggcca   1560
gacgggaaa tgcacgggaa caagtgtgcc atgtgcgcct ccgtgttcaa gctgaagaa   1620
gaagaaaaga aaacgacaa agaagaaag gaaagtcg aagccgagaa agtgaagagg   1680
gaagccgtgc aagaactctg ttctgagtac cggcactacg tccggaacgg cagactgcct  1740
tgtactcgg aaaacgaccc aatcgaagga ctggacggga agatcatgg caacacctgt   1800
agtatgtgcg aggcattctt tcaacaagaa gccaaagaaa aagagcgggc cgagcctgca  1860
gccaaagtca aagagaagc tgagaaagag acatgcgacg agttccggcg gctgctgcag  1920
aatgaaaac tcttctgtac acgtgaaaat gatcccgtgc ggggaccaga tggaaagacc  1980
catgggaaca atgcgctat gtgcaaggcc gtgttccaaa agagaatga ggaacgcaag   2040
cggaagagag aagaagatca gcggaacgcc gctggccacg atctagtgg cggaggtggt  2100
ggaaataccc aggacgagtg tgccgaatac cgggaacaaa tgaaaaatgg aaggctagcc   2160
tgcacgcgg aatctgaccc cgttagagat gccgacggca agtcctacaa caaccagtgc   2220
accatgtgta aagccaagct cgagcgcgag gccgagcgga gaatgagta cagcagaagc   2280
cggtctaacg gcaccggctc tgagtctggc aaggatacct gtgacgagtt cagatcccag  2340
atgaagaacg gaaactcat ctgcacaaga gaatcagacc cagtccgggg acctgacggg  2400
aaaactcatg gcaacaagtg cacaatgtgc aaagagaaac tggaacgcga ggctgccgag  2460
```

```
aagaaaaaga aagaggacga ggatcggagc aacaccggcg agagatctaa taccggcgag   2520
cggagcaatg acaaagagga cctctgccgg gaattccggt ccatgcagag aaacggaaag   2580
ctgatatgta cgcgcgagaa caatcccgtt cggggcccct atgggaagat gcacattaac   2640
aaatgtgcaa tgtgccagag catcttcgac agagaggcca acgaacgcaa aaagaaggat   2700
gaagagaagt ccagcagcaa gcccagcaac aacgctaaag tgatctactg a            2751
```

| SEQ ID NO: 5 | moltype = DNA   length = 3195 |
|---|---|
| FEATURE | Location/Qualifiers |
| source | 1..3195 |
| | mol_type = unassigned DNA |
| | organism = Rattus norvegicus |

SEQUENCE: 5
```
atgaagatag ccacagtgtc agtgcttctg cccttggctc tttgcctcat acaagatgct     60
gccagtaaga atgaagatca ggaaatgtgc catgaatttc aggcatttat gaaaaatgga    120
aaactgttct gtccccagga taagaaattt tttcaaagtc ttgatggaat aatgttcatc    180
aataaatgtg ccacgtgcaa aatgatactg aaaaagaag caaaatcaca gaagagggcc    240
aggcatttag caagagctcc caaggctact gccccaacag agctgaattg tgatgatttt    300
aaaaaaggag aaagagatgg ggattttatc tgtcctgatt attatgaagc tgtttgtggc    360
acagatggga aacatatga caacagatgt gcactgtgtg ctgagaatgc gaaaaccggg    420
tcccaaattg gtgtaaaaag tgaaggggaa tgtaagagca gtaatccaga gcaggatgta    480
tgcagtgctt ttcggccctt tgttagagat ggaagacttg gatgcacaag ggaaaatgat    540
cctgttcttg gtcctgaatgg gaagacgcat ggcaataagt gtgcaatgtg tgctgagctg    600
tttttaaaag aagctgaaaa tgccaagcga gagggtgaaa ctagaattcg acgaaatgct    660
gaaaaggatt tttgcaagga atatgaaaaa caagtgagaa atggaaggct ttttgtaca    720
cgggagagtg atccagtccg tggccctgac ggcaggatgc atggcaacaa atgtgccctg    780
tgtgctgaaa ttttcaagca gcgttttca gaggaaaaca gtaaaacaga tcaaaatttg    840
ggaaaagctg aagaaaaac taaagttaaa agagaaattg tgaaactctg cagtcaatat    900
caaaatcagg caaagaatgg aatacttttc tgtaccagag aaaatgaccc tattcgtggt    960
ccagatggga aaatgcatgg caacttgtgt tccatgtgtc aagcctactt ccaagcagaa   1020
aatgaagaaa agaaaaaggc tgaagcacga gctagaaaca gaaaagaatc tggaaaagca   1080
acctcatatg cagagctttg cagtgaatat cgaaagcttg tgaggaacgg aaaacttgct   1140
tgcaccagag agaacgatcc tatccagggc ccagatggga agtgcatggc aacacctgc   1200
tccatgtgtg aggtcttctt ccaagcagaa gaagaagaa agaaaagaa ggaaggtaaa   1260
tcaagaaaca aaagacaatc taagagtaca gcttccttg aggagttgtg tagtgaatac   1320
cgcaaatcca ggaaaaacgg acggcttttt tgcaccagag agaatgaccc catccagggc   1380
ccagatggaa aaatgcatgg caacacctgc tccatgtgtg aggccttctt tcaacaagaa   1440
gaaagagcaa gagcaaaggc taaaagaaa gctgcaaagg aaatctgcag tgaatttcgg   1500
gaccaagtga ggaatggaac acttatatgc accagggagc ataatcctgt ccgtggccca   1560
gatgccaaaa tgcatggaaa caagtgtgcc atgtgtgcca gtgttcaa acttgaagaa   1620
gaagagaaga aaaatgataa agaagaaaaa gggaaagtcg aggctgaaaa agttaagaga   1680
gaagcagttc aggagctgtg cagtgaatat cgtcattatg tgaggaatgg acgactcccc   1740
tgtaccagag agaatgatcc tattgagggt ctagatggga aaatccacgg caacacctgc   1800
tccatgtgtg aagccttctt ccagcaagaa gcaaaagaaa aagaaagctg tgaacccaga   1860
gcaaaagtca aaagagaagc tgaaaaggag acatgcgatg aatttcggag acttttgcaa   1920
aatgaaaac ttttctgcac aagagaaaat gatcctgtgc gtggcccaga tggcaagacc   1980
catgcaaca agtgtgccat gtgtaaggca gtcttccaga agaaaatga ggaaagaag   2040
aggaaagaag aggaagatca gagaaatgct gcaggacatg gttccagtgg tggtggagga   2100
ggaaacactc aggacgaatg tgctgagtat cgggaacaaa tgaaaaatgg aagactcagc   2160
tgtactcggg agagtgatcc tgtacgtgat gctgatggca aatcgtacaa caatcagtgt   2220
accatgtgta aagcaaaatt ggaaagaaa gcagagaga aaaatgagta ttctcgctcc   2280
agatcaaatg ggactggatc agaatcaggg aaggatacat gtgatgagtt tagaagcaa   2340
atgaaaaatg gaaactcat ctgcactcga gaaagtgacc ctgtccgggg tccagatggc   2400
aagacacatg gcaataagtg tactatgtgt aaggaaaaac tggaaaggga agcagctgaa   2460
aaaaaaaaga aagaggatga agacaggagc aatacaggag aaaggagcaa tacaggaaa   2520
aggagcaatg acaaagagga tctgtgtcgt gaatttcgaa gcatgcagag aaatggaaag   2580
cttatctgca ccagagaaaa taaccctgtt cgaggcccat atggcaagat gcacatcaat   2640
aaatgtgcta tgtgtcagag catctttgat cgagaagcta atgaaagaaa aagaaagat   2700
gaagagaaat caagtagcaa gccctcaaat aatgcaaagg atgagtgcag tgaatttcga   2760
aactatataa ggaacaatga actcatctgc cctagagaga atgacccagt gcacggtgct   2820
gatggaaagt tctatacaaa caagtgctac atgtgcagag ctgtctttct aacagaagct   2880
ttggaaaggg caaagcttca agaaaagcca tcccatgtta gagcttctca agaggaagac   2940
agcccagact ctttcagttc tctggattct gagatgtgca agactaccg agtattgccc   3000
aggataggtt atctttgtcc aaaggattta agcctgtct gtggtgacga tggccaaacc   3060
tacaacaatc cttgcatgct ctgtcatgaa aacctgatac gccaaacaaa tacacactc   3120
cgcagtacag ggaagtgtga gggagcagc accccaggaa ccaccgcagc cagcatgccc   3180
ccgtctgacg aatga                                                    3195
```

| SEQ ID NO: 6 | moltype = DNA   length = 3195 |
|---|---|
| FEATURE | Location/Qualifiers |
| misc_feature | 1..3195 |
| | note = Synthetic Construct |
| source | 1..3195 |
| | mol_type = other DNA |
| | organism = synthetic construct |

SEQUENCE: 6
```
atgaagatcg ccaccgtgtc tgtgctgctg cctctggctc tgtgcctgat tcaggatgcc     60
gccagcaaga acgaggacca agagatgtgc acgcagttcc aggcctttat gaagaacggc    120
aagctgtttc gccctcaaga caagaagttc ttccagagcc tggacggcat catgttcatc    180
aacaagtgcg ccacatgcaa gatgatcctg gaaaagagg ccaagagcca agcgcgggcc    240
```

-continued

```
agacaccttg ctagagcccc taaagccacc gctcctaccg agctgaactg cgacgacttc    300
aagaaaggcg agcgcgacgg cgacttcatc tgccccgatt attacgaggc cgtgtgcggc    360
accgatggca agacctacga taacagatgc gccctgtgcg ccgagaatgc caagacagga    420
tctcagatcg gcgtgaagtc tgagggcgag tgcaagagca gcaaccccga gcaggatgtg    480
tgcagcgcct tcagacccct cgtcagagat ggcagactgg gctgcaccag agaaaacgat    540
cctgtgctgg gccctgacgg caagacacac ggaaacaagt gtgctatgtg tgccgagctg    600
ttcctgaaag aggccgaaaa cgccaagaga gagggcgaga cacggatcag aagaaacgcc    660
gagaaggact tctgcaaaga atacgagaag caagtgcgga acggacgcct gttctgtacc    720
cgggaaagcg atccagtcag aggccccgat ggaagaatgc acggcaacaa atgcgcactg    780
tgtgctgaga tcttcaagca gcggttcagc gaggaaaaca gcaagaccga ccagaacctg    840
ggcaaagccg aagaaaagac caaagtgaag cgcgagatcg tgaagctgtg cagccagtac    900
cagaaccagg ccaagaatgg catcctgttc tgcacgcgcg agaacgaccc catcagagga    960
cccgacggaa agatgcatgg aaacctgtgc agcatgtgcc aggcctactt ccaggccgag   1020
aacgaagaga agaaagaggc cgaagccagg gccagaaaca agagagaaag cggcaaggcc   1080
accagctacg ccgaactgtg tagcgagtac agaaagctcg tgcggaatgg caagctggcc   1140
tgcactaggg aaaatgaccc tattcaggga ccagacggca aggtgcacgg aatacctgt    1200
tccatgtgcg aggtgttctt tcaggccgag aagaggaaa aaaagaagaa agagggcaag   1260
tcccggaaca agcggcagag caagagcacc gccagcttcg aggaactgtg ctccgagtac   1320
cggaagtcca gaaagaatgg ccggcttttc tgcacgagag agaatgatcc catccagggg   1380
cctgatggca aatgcatgg caatacttgc tctatgtgcg aggcatttt ccagcaagag    1440
gaacgggcca gagccaaggc caaaagagag gccgccaaag agatctgcag cgagtttagg   1500
gaccaagtcc gcaacggcac cctgatctgc accagggaac acaaccctgt cagagggcca   1560
gacgggaaaa tgcacgggaa caagtgtgcc atgtgcgcct ccgtgttcaa gctgaagaa    1620
gaagaaaaga aaaacgacaa agaagagaag ggaaagtcg aagccgagaa agtgaagagg    1680
gaagccgtgc aagaactctg ttctgagtac cggcactacg tccggaacgg cagactgcct   1740
tgtactcggg aaaacgaccc aatcgaagga ctggacggga agatccatgg caacacctgt   1800
agtatgtgcg aggcattctt tcaacaagaa gccaaagaaa aagagcgggc cgagcctcgg   1860
gccaaagtca aagaagaagc tgagaaagag acatgcgacg agttccggcg gctgctgcag   1920
aatggaaaac tcttctgtac acgtgaaaat gatcccgtgc ggggaccaga tggaaagacc   1980
catggaaaca aatgcgctat gtgcaaggcc gtgttccaaa aagagaatga ggaacgcaag   2040
cggaaagagg aagaagatca gcggaacgcc gctggccacg gatctagtgg cggaggtggt   2100
ggaaatacc aggacgagtg tgccgaatac cgggaacaga tgaagaatgg aaggctgagc   2160
tgcacacggg aatctgaccc cgttagagat gccgacggca gtcctacaa caaccagtgc   2220
accatgtgta aagccaagct cgagcgcgag gccgacggga agatgagta cagcagaagc   2280
cggtctaacg gcaccggctc tgagtctggc aaggatacct gtgacgagtt cagatcccag   2340
atgaagaacg gaaactcat ctgcacaaga gaatcagacc cagtccgggg acctgacggg    2400
aaaactcatg caacaagtg cacaatgtgc aagagaaac tggaacgcga ggctgccgag    2460
aagaaaaaga aagaggacga ggatcggagc aacaccggcg agagatctaa taccggcgag   2520
cggagcaatg acaaaggga cctgccggg gaattccgt ccatgcagag aaacggaaag     2580
ctgatatgta cgcgcgagaa caatcccgtt cggggcccctt atgggaagat gcacattaac   2640
aaatgtgcaa tgtgccagag catcttcgac agagaggcca cgaacgcaa aagaaggat    2700
gaagagaagt ccagcagcaa gcccagcaac aacgccaagg acgaatgcag cgaattccgg   2760
aactatatcc ggaacaacga gctgatctgt ccgcgagaga atgaccctgt gcatggccgt   2820
gatgaaagt tctacaccaa caagtgttat atgtgcagag ccgtctttct gacagaggcc    2880
ctggaaaagag ccaagctgca agagaagcct tctcacgtgc gggcctctca agaagaggac  2940
agccctgata gcttcagcag cctggacagc gagatgtgca aggactacag agtgctgccc   3000
cggatcggct atctgtgccc caaggatctg agcctgtgg ccgcagaca                 3060
tacaacaatc cctgcatgct gtgtcacgag aacctgatcc ggcagaccaa cacacacatc   3120
cggtccaccg gcaagtgcga agagtctagc acacctggaa caaccgccgc ctctatgcct   3180
cctagcgacg aatga                                                     3195
```

SEQ ID NO: 7        moltype = AA   length = 1094
FEATURE             Location/Qualifiers
source              1..1094
                    mol_type = protein
                    organism = Homo sapiens
SEQUENCE: 7
MKIATVSVLL PLALCLIQDA ASKNEDQEMC HEFQAFMKNG KLFCPQDKKF FQSLDGIMFI    60
NKCATCKMIL EKEAKSQKRA RHLARAPKAT APTELNCDDF KKGERDGDFI CPDYYEAVCG   120
TDGKTYDNRC ALCAENAKTG SQIGVKSEGE CKSSNPEQDV CSAFRPVFRD GRLGCTREND   180
PVLGPDGKTH GNKCAMCAEL FLKEAENAKR EGETRIRRNA EKDFCKEYEK QVRNGRLFCT   240
RESDPVRGPD GRMHGNKCAL CAEIFKQRFS EENSKTDQNL GKAEEKTKVK REIVKLCSQY   300
QNQAKNGILF CTRENDPIRG PDGKMHGNLC SMCQAYFQAE NEEKKKAEAR ARNKRESGKA   360
TSYAELCSEY RKLVRNGKLA CTRENDPIQG PDGKVHGNTC SMCEVFFQAE EEEKKKKEGK   420
SRNKRQSKST ASFEELCSEY RKSRKNGRLF CTRENDPIQG PDGKMHGNTC MCEAFFQQE    480
ERARAKAKRE AAKEICSEFR DQVRNGTLIC TREHNPVRGP DGKMHGNKCA MCASVFKLEE   540
EEKKNDKEEK GKVEAEKVKR EAVQELCSEY RHYVRNGRLP CTRENDPIEG LDGKIHGNTC   600
SMCEAFFQQE AKEKERAEPR AKVKREAEKE TCDEFRRLLQ NGKLFCTREN DPVRGPDGKT   660
HGNKCAMCKA VFQKENEEERR RKEEEDQRNA AGHGSSGGGG GNTQDECAEY REQMKNGRLS   720
CTRESDPVRD ADGKSYNNQC TMCKAKLERE AERKNEYSRS RSNGTGSESG KDTCDEFRSQ   780
MKNGKLICTR ESDPVRGPDG KTHGNKCTMC KEKLEREAAE KKKKEDEDRS NTGERSNTGE   840
RSNDKEDLCR EFRSMQRNGK LICTRENNPV RGPYGKMHIN KCAMCQSIFD REANERKKKD   900
EEKSSSKPSN NAKDQCRQVQ NEAEDAKFRQ PGRSLASVAR MSTDECSEFR NYIRNNELIC   960
PRENDPVHGA DGKFYTNKCY MCRAVFLTEA LERAKLQEKP SHVRASQEED SPDSFSSLDS  1020
EMCKDYRVLP RIGYLCPKDL KPVCGDDGQT YNNPCMLCHE NLIRQTNTHI RSTGKCEESS  1080
TPGTTAASMP PSDE                                                   1094

SEQ ID NO: 8        moltype = AA   length = 916
FEATURE             Location/Qualifiers

```
source                  1..916
                        mol_type = protein
                        organism = Homo sapiens
SEQUENCE: 8
MKIATVSVLL PLALCLIQDA ASKNEDQEMC HEFQAFMKNG KLFCPQDKKF FQSLDGIMFI    60
NKCATCKMIL EKEAKSQKRA RHLARAPKAT APTELNCDDF KKGERDGDFI CPDYYEAVCG   120
TDGKTYDNRC ALCAENAKTG SQIGVKSEGE CKSSNPEQDV CSAFRPFVRD GRLGCTREND   180
PVLGPDGKTH GNKCAMCAEL FLKEAENAKR EGETRIRRNA EKDFCKEYEK QVRNGRLFCT   240
RESDPVRGPD GRMHGNKCAL CAEIFKQRFS EENSKTDQNL GKAEEEKTKVK REIVKLCSQY   300
QNQAKNGILF CTRENDPIRG PDGKMHGNLC SMCQAYFQAE NEEKKKAEAR ARNKRESGKA   360
TSYAELCSEY RKLVRNGKLA CTRENDPIQG PDGKVHGNTC SMCEVFFQAE EEEKKKKEGK   420
SRNKRQSKST ASFEELCSEY RKSRKNGRLF CTRENDPIQG PDGKMHGNTC SMCEAFFQQE   480
ERARAKAKRE AAKEICSEFR DQVRNGTLIC TREHNPVRGP DGKMHGNKCA MCASVFKLEE   540
EEKKNDKEEK GKVEAEKVKR EAVQELCSEY RHYVRNGRLP CTRENDPIEG LDGKIHGNTC   600
SMCEAFFQQE AKEKERAEPR AKVKREAEKE TCDEFRRLLQ NGKLFCTREN DPVRGPDGKT   660
HGNKCAMCKA VFQKENEERK RKEEEDQRNA AGHGSSGGGG GNTQDECAEY REQMKNGRLS   720
CTRESDPVRD ADGKSYNNQC TMCKAKLERE AERKNEYSRS RSNGTGSESG KDTCDEFRSQ   780
MKNGKLICTR ESDPVRGPDG KTHGNKCTMC KEKLEREAAE KKKKEDEDRS NTGERSNTGE   840
RSNDKEDLCR EFRSMQRNGK LICTRENNPV RGPYGKMHIN KCAMCQSIFD REANERKKKD   900
EEKSSSKPSN NAKVIY                                                  916

SEQ ID NO: 9             moltype = AA   length = 1064
FEATURE                  Location/Qualifiers
source                   1..1064
                         mol_type = protein
                         organism = Homo sapiens
SEQUENCE: 9
MKIATVSVLL PLALCLIQDA ASKNEDQEMC HEFQAFMKNG KLFCPQDKKF FQSLDGIMFI    60
NKCATCKMIL EKEAKSQKRA RHLARAPKAT APTELNCDDF KKGERDGDFI CPDYYEAVCG   120
TDGKTYDNRC ALCAENAKTG SQIGVKSEGE CKSSNPEQDV CSAFRPFVRD GRLGCTREND   180
PVLGPDGKTH GNKCAMCAEL FLKEAENAKR EGETRIRRNA EKDFCKEYEK QVRNGRLFCT   240
RESDPVRGPD GRMHGNKCAL CAEIFKQRFS EENSKTDQNL GKAEEEKTKVK REIVKLCSQY   300
QNQAKNGILF CTRENDPIRG PDGKMHGNLC SMCQAYFQAE NEEKKKAEAR ARNKRESGKA   360
TSYAELCSEY RKLVRNGKLA CTRENDPIQG PDGKVHGNTC SMCEVFFQAE EEEKKKKEGK   420
SRNKRQSKST ASFEELCSEY RKSRKNGRLF CTRENDPIQG PDGKMHGNTC SMCEAFFQQE   480
ERARAKAKRE AAKEICSEFR DQVRNGTLIC TREHNPVRGP DGKMHGNKCA MCASVFKLEE   540
EEKKNDKEEK GKVEAEKVKR EAVQELCSEY RHYVRNGRLP CTRENDPIEG LDGKIHGNTC   600
SMCEAFFQQE AKEKERAEPR AKVKREAEKE TCDEFRRLLQ NGKLFCTREN DPVRGPDGKT   660
HGNKCAMCKA VFQKENEERK RKEEEDQRNA AGHGSSGGGG GNTQDECAEY REQMKNGRLS   720
CTRESDPVRD ADGKSYNNQC TMCKAKLERE AERKNEYSRS RSNGTGSESG KDTCDEFRSQ   780
MKNGKLICTR ESDPVRGPDG KTHGNKCTMC KEKLEREAAE KKKKEDEDRS NTGERSNTGE   840
RSNDKEDLCR EFRSMQRNGK LICTRENNPV RGPYGKMHIN KCAMCQSIFD REANERKKKD   900
EEKSSSKPSN NAKDECSEFR NYIRNNELIC PRENDPVHGA DGKFYTNKCY MCRAVFLTEA   960
LERAKLQEKP SHVRASQEED SPDSFSSLDS EMCKDYRVLP RIGYLCPKDL KPVCGDDGQT  1020
YNNPCMLCHE NLIRQTNTHI RSTGKCEESS TPGTTAASMP PSDE                  1064

SEQ ID NO: 10            moltype = AA   length = 39
FEATURE                  Location/Qualifiers
REGION                   1..39
                         note = Synthetic Construct
source                   1..39
                         mol_type = protein
                         organism = synthetic construct
SEQUENCE: 10
EMCHEFQAFM KNGKLFCPQD KKFFQSLDGI MFINKCATC                           39

SEQ ID NO: 11            moltype = AA   length = 63
FEATURE                  Location/Qualifiers
REGION                   1..63
                         note = Synthetic Construct
source                   1..63
                         mol_type = protein
                         organism = synthetic construct
SEQUENCE: 11
APTELNCDDF KKGERDGDFI CPDYYEAVCG TDGKTYDNRC ALCAENAKTG SQIGVKSEGE    60
CKS                                                                  63

SEQ ID NO: 12            moltype = AA   length = 62
FEATURE                  Location/Qualifiers
REGION                   1..62
                         note = Synthetic Construct
source                   1..62
                         mol_type = protein
                         organism = synthetic construct
SEQUENCE: 12
NPEQDVCSAF RPFVRDGRLG CTRENDPVLG PDGKTHGNKC AMCAELFLKE AENAKREGET    60
RI                                                                   62

SEQ ID NO: 13            moltype = AA   length = 67
```

```
FEATURE                 Location/Qualifiers
REGION                  1..67
                        note = Synthetic Construct
source                  1..67
                        mol_type = protein
                        organism = synthetic construct
SEQUENCE: 13
NAEKDFCKEY EKQVRNGRLF CTRESDPVRG PDGRMHGNKC ALCAEIFKQR FSEENSKTDQ   60
NLGKAEE                                                            67

SEQ ID NO: 14           moltype = AA  length = 62
FEATURE                 Location/Qualifiers
REGION                  1..62
                        note = Synthetic Construct
source                  1..62
                        mol_type = protein
                        organism = synthetic construct
SEQUENCE: 14
REIVKLCSQY QNQAKNGILF CTRENDPIRG PDGKMHGNLC SMCQAYFQAE NEEKKKAEAR   60
AR                                                                 62

SEQ ID NO: 15           moltype = AA  length = 63
FEATURE                 Location/Qualifiers
REGION                  1..63
                        note = Synthetic Construct
source                  1..63
                        mol_type = protein
                        organism = synthetic construct
SEQUENCE: 15
TSYAELCSEY RKLVRNGKLA CTRENDPIQG PDGKVHGNTC SMCEVFFQAE EEEKKKKEGK   60
SRN                                                                63

SEQ ID NO: 16           moltype = AA  length = 59
FEATURE                 Location/Qualifiers
REGION                  1..59
                        note = Synthetic Construct
source                  1..59
                        mol_type = protein
                        organism = synthetic construct
SEQUENCE: 16
ASFEELCSEY RKSRKNGRLF CTRENDPIQG PDGKMHGNTC SMCEAFFQQE ERARAKAKR    59

SEQ ID NO: 17           moltype = AA  length = 62
FEATURE                 Location/Qualifiers
REGION                  1..62
                        note = Synthetic Construct
source                  1..62
                        mol_type = protein
                        organism = synthetic construct
SEQUENCE: 17
EAAKEICSEF RDQVRNGTLI CTREHNPVRG PDGKMHGNKC AMCASVFKLE EEEKKNDKEE   60
KG                                                                 62

SEQ ID NO: 18           moltype = AA  length = 62
FEATURE                 Location/Qualifiers
REGION                  1..62
                        note = Synthetic Construct
source                  1..62
                        mol_type = protein
                        organism = synthetic construct
SEQUENCE: 18
EAVQELCSEY RHYVRNGRLP CTRENDPIEG LDGKIHGNTC SMCEAFFQQE AKEKERAEPR   60
AK                                                                 62

SEQ ID NO: 19           moltype = AA  length = 63
FEATURE                 Location/Qualifiers
REGION                  1..63
                        note = Synthetic Construct
source                  1..63
                        mol_type = protein
                        organism = synthetic construct
SEQUENCE: 19
EAEKETCDEF RRLLQNGKLF CTRENDPVRG PDGKTHGNKC AMCKAVFQKE NEERKRKEEE   60
DQR                                                                63

SEQ ID NO: 20           moltype = AA  length = 57
FEATURE                 Location/Qualifiers
REGION                  1..57
                        note = Synthetic Construct
```

```
source                          1..57
                                mol_type = protein
                                organism = synthetic construct
SEQUENCE: 20
GNTQDECAEY REQMKNGRLS CTRESDPVRD ADGKSYNNQC TMCKAKLERE AERKNEY        57

SEQ ID NO: 21              moltype = AA  length = 63
FEATURE                    Location/Qualifiers
REGION                     1..63
                           note = Synthetic Construct
source                     1..63
                           mol_type = protein
                           organism = synthetic construct
SEQUENCE: 21
ESGKDTCDEF RSQMKNGKLI CTRESDPVRG PDGKTHGNKC TMCKEKLERE AAEKKKKEDE     60
DRS                                                                   63

SEQ ID NO: 22              moltype = AA  length = 63
FEATURE                    Location/Qualifiers
REGION                     1..63
                           note = Synthetic Construct
source                     1..63
                           mol_type = protein
                           organism = synthetic construct
SEQUENCE: 22
NDKEDLCREF RSMQRNGKLI CTRENNPVRG PYGKMHINKC AMCQSIFDRE ANERKKKDEE     60
KSS                                                                   63

SEQ ID NO: 23              moltype = AA  length = 92
FEATURE                    Location/Qualifiers
REGION                     1..92
                           note = Synthetic Construct
source                     1..92
                           mol_type = protein
                           organism = synthetic construct
SEQUENCE: 23
NNAKDQCRQV QNEAEDAKFR QPGRSLASVA RMSTDECSEF RNYIRNNELI CPRENDPVHG     60
ADGKFYTNKC YMCRAVFLTE ALERAKLQEK PS                                   92

SEQ ID NO: 24              moltype = AA  length = 62
FEATURE                    Location/Qualifiers
REGION                     1..62
                           note = Synthetic Construct
source                     1..62
                           mol_type = protein
                           organism = synthetic construct
SEQUENCE: 24
NNAKDECSEF RNYIRNNELI CPRENDPVHG ADGKFYTNKC YMCRAVFLTE ALERAKLQEK     60
PS                                                                    62

SEQ ID NO: 25              moltype = AA  length = 62
FEATURE                    Location/Qualifiers
REGION                     1..62
                           note = Synthetic Construct
source                     1..62
                           mol_type = protein
                           organism = synthetic construct
SEQUENCE: 25
SLDSEMCKDY RVLPRIGYLC PKDLKPVCGD DGQTYNNPCM LCHENLIRQT NTHIRSTGKC     60
EE                                                                    62

SEQ ID NO: 26              moltype = DNA  length = 3195
FEATURE                    Location/Qualifiers
misc_feature               1..3195
                           note = Synthetic Construct
source                     1..3195
                           mol_type = other DNA
                           organism = synthetic construct
SEQUENCE: 26
atgaagatcg ccaccgtgtc tgtgctgctg cctctggctc tgtgcctgat tcaggatgcc     60
gccagcaaga acgaggacca agagatgtgc cacgagttcc aggcctttat gaagaacggc    120
aagctgttct gccctcaaga caagaagttc ttccagagcc tggacggcat catgttcatc    180
aacaagtgcg ccacatgcaa gatgatcctg gaaaagagg ccaagagcca gaagcgggcc    240
agacaccttg ctagagcccc taaagccacc gctcctaccg agctgaactg cgacgacttc    300
aagaaaggcg agcgcgacgg cgacttcatc tgccccgatt attacgaggc cgtgtgcggc    360
accgatggca agacctacga taacagatgc gccctgtgcg ccgagaatgc caagacagga    420
tctcagatcg gcgtgaagtc tgagggcgag tgcaagagca gcaacccgga gcaggatgtg    480
tgcagcgcct tcagaccctt cgtcagagat ggcagactgg gctgcaccag agaaaacgat    540
cctgtgctgg gccctgacgg caagacacac ggaaacaagt gtgctatgtg tgccgagctg    600
```

```
ttcctgaaag aggccgaaaa cgccaagaga gagggcgaga cacggatcag aagaaacgcc  660
gagaaggact tctgcaaaga atacgagaag caagtgcgga acggacgcct gttctgtacc  720
cgggaaagcg atccagtcag aggccccgat ggaagaatgc acggcaacaa atgcgcactg  780
tgtgctgaga tcttcaagca gcggttcagc gaggaaaaca gcaagaccga ccagaacctg  840
ggcaaagccg aagaaaagac caaagtgaag cgcgagatcg tgaagctgtg cagccagtac  900
cagaaccagg ccaagaatgg catcctgttc tgcacacgcg agaacgaccc catcagagga  960
cccgacggaa agatgcatgg aaacctgtgc agcatgtgcc aggcctactt ccaggccgag 1020
aacgaagaga agaagaaggc cgaagccagg gccagaaaca agagagaaag cggcaaggcc 1080
accagctacg ccgaactgtg tagcgagtac agaaagctcg tgcggaatgg caagctggcc 1140
tgcactaggg aaaatgaccc tattcaggga ccagacggca aggtgcacgg gaatacctgt 1200
tccatgtgcg aggtgttctt tcaggccgag gaagaggaaa aaaagaagaa agagggcaag 1260
tcccggaaca agcggcagag caagagcacc gccagcttcg aggaactgtg ctccgagtac 1320
cggaagtcca gaaagaatgg ccggcttttc tgcacgagag agaatgatcc catccagggg 1380
cctgatggca aaatgcatgg caatacttgc tctatgtgcg agcattttt ccagcaagag 1440
gaacgggcca gagccaaggc caaaagagag gccgccaaag agatctgcag cgagtttagg 1500
gaccaagtcc gcaacggcac cctgatctgc accagggaac acaaccctgt cagagggcca 1560
gacgggaaaa tgcacgggaa caagtgtgcc atgtgcgcct ccgtgttcaa gctggaagaa 1620
gaagaaaaca aaacgacaa agaagagaag ggaaaagtcg aagccgagaa agtgaagagg 1680
gaagccgtgc aagaactctg ttctgagtac cggcactacg tccggaacgg cagactgcct 1740
tgtactcggg aaaacgaccc aatcgaagga ctggacggga agatccatgg caacacctgt 1800
agtatgtgcg aggcattctt tcaacaagaa gccaaagaaa aagagcgggc cgagcctcgg 1860
gccaaagtca aaagagaagc tgagaaagag acatgcgagg agttccggcg gctgctgcag 1920
aatggaaaac tcttctgtac acgtgaaaat gatcccgtgc ggggaccaga tggaaagacc 1980
catgggaaca aatgcgctat gtgcaaggcc gtgttccaaa aagagaatga ggaacgcaag 2040
cggaaagagg aagaagatca gcggaacgcc gctggccacg gatctagtgg cggaggtggt 2100
ggaaataccc aggacgagtg tgccgaatac cgggaacaga tgaagaatgg aaggctgagc 2160
tgcacacggg aatctgaccc cgttagagat gccgacggca agtcctacaa caaccagtgc 2220
accatgtgta aagccaagct cgagcgcgag gccgagcgga agaatgagta cagcagaagc 2280
cggtctaacg gcaccggctc tgagtctggc aaggatacct gtgacgagtt cagatcccag 2340
atgaagaacg ggaaactcat ctgcacaaga gaatcagacc cagtccgggg acctgacggg 2400
aaaactcatg gcaacaagtg cacaatgtgc aaagagaaac tggaacgcga ggctgccgag 2460
aagaaaaaga aagaggacga ggatcggagc aacaccggcg agagatctaa taccggcgag 2520
cggagcaatg acaaagagga cctctgccgg gaatttcgga gcatgcagag aaacggaaag 2580
ctcatatgta cgcgcgagaa caatcccgtt cggggcccctt atgggaagat gcacattaac 2640
aaatgtgcaa tgtgccagag catcttcgac agagagcca gcaacgcaa aaagaaggat 2700
gaagagaagt ccagcagcaa gcccagcaac aacgccaagg acgaatgctc tgagttccgc 2760
aattacatcc ggaacaacga gctgatctgt ccgcgagaga acgatccagt tcatggcgcc 2820
gatgggaagt tctacaccaa caagtgttat atgtgcagag ccgtcttct gacagaggcc 2880
ctggaaagag ccaagctgca agagaagcct tctcacgtgc gggcctctca agaagaggac 2940
agccctgata gcttcagcag cctggacagc gagatgtgca aggactacag agtgctgccc 3000
cggatcggct atctgtgccc caaggatctg aagcctgtgt gtggcgacga cggccagaca 3060
tacaacaatc cctgcatgct gtgtcacgag aacctgatcc ggcagaccaa cacacacatc 3120
cggtccaccg gcaagtgcga agagtctagc acacctggaa caaccgccgc ctctatgcct 3180
cctagcgacg aatga                                                  3195
```